US010734102B2

(12) United States Patent
Yakami et al.

(10) Patent No.: US 10,734,102 B2
(45) Date of Patent: Aug. 4, 2020

(54) APPARATUS, METHOD, SYSTEM, AND PROGRAM FOR CREATING AND DISPLAYING MEDICAL REPORTS

(71) Applicant: CANON KABUSHIKI KAISHA, Tokyo (JP)

(72) Inventors: Masahiro Yakami, Kyoto (JP); Yutaka Emoto, Kyoto (JP); Keisuke Teranishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 861 days.

(21) Appl. No.: 15/221,022

(22) Filed: Jul. 27, 2016

(65) Prior Publication Data
US 2017/0032105 A1 Feb. 2, 2017

(30) Foreign Application Priority Data

Jul. 31, 2015 (JP) ................................. 2015-152089
Sep. 18, 2015 (JP) ................................. 2015-185268
Sep. 25, 2015 (JP) ................................. 2015-188193

(51) Int. Cl.
*G16H 15/00* (2018.01)
*G16H 50/20* (2018.01)

(52) U.S. Cl.
CPC ............. *G16H 15/00* (2018.01); *G16H 50/20* (2018.01)

(58) Field of Classification Search
CPC ............................... G16H 15/00; G16H 50/20
See application file for complete search history.

(56) References Cited

U.S. PATENT DOCUMENTS

| 8,233,750 B2 | 7/2012 | Minakuchi et al. | |
|---|---|---|---|
| 2007/0143150 A1* | 6/2007 | Sasai | G06Q 50/24 705/3 |
| 2012/0176408 A1* | 7/2012 | Moriya | A61B 6/465 345/629 |
| 2014/0149942 A1* | 5/2014 | Wood-Salomon | G16H 80/00 715/840 |

FOREIGN PATENT DOCUMENTS

| CN | 1680963 A | 10/2005 |
|---|---|---|
| CN | 1873676 A | 12/2006 |
| CN | 1969775 A | 5/2007 |
| CN | 101123911 A | 2/2008 |
| CN | 101158994 A | 4/2008 |
| CN | 102473199 A | 5/2012 |
| CN | 101742051 B | 1/2014 |
| JP | 2007-140862 A | 6/2007 |

* cited by examiner

*Primary Examiner* — Robert A Sorey
*Assistant Examiner* — Kristine K Rapillo
(74) *Attorney, Agent, or Firm* — Canon U.S.A., Inc. IP Division

(57) ABSTRACT

A medical report creation apparatus and method includes creating a medical report including a plurality of sets of information that is the object of diagnosis and association information indicating associations among a plurality of items included in each of the plurality of sets of information, specifying one item out of a plurality of items included in each of a plurality of sets of information included in a previously created medical report, identifying, based on association information by which the specified one item is associated, at least one item of the plurality of items included in the previously created medical report in response to specifying the one item, and displaying the at least one identified item for editing the medical report.

17 Claims, 48 Drawing Sheets

FIG. 4A

| ITEM ID | REPORT ID | TYPE | CONTENT | DEGREE OF CERTAINTY | COMMISSIONING TAG |
|---|---|---|---|---|---|
| 1 | 1 | SITE |  | | |
| 2 | 1 | FINDINGS | LEFT KIDNEY HAS BEEN ENUCLEATED, LOCALLY RECURRING TUMOR MASS NOT INDICATED. | HIGH | |
| 3 | 1 | DIAGNOSIS | POSTOPERATIVE COURSE OF CANCER OF LEFT KIDNEY OBVIOUS RECURRENCE NOT INDICATED. | MEDIUM | CANCER OF LEFT KIDNEY, CONFIRMATION OF POSTOPERATIVE COURSE |
| 4 | 1 | SITE |  | | |
| 5 | 1 | FINDINGS | SOFT TISSUE TUMOR MASS OBSERVED AT L1 CENTRUM, ACCOMPANIED BY OSTEOLYSIS. MO MARKED CHANGE FROM PREVIOUS TIME. | HIGH | |
| 6 | 1 | DIAGNOSIS | NO TENDENCY FOR METASTASIS TO LUMBUS TO INCREASE. | HIGH | CANCER OF LEFT KIDNEY, CONFIRMATION OF POSTOPERATIVE COURSE |
| 7 | 2 | SITE |  | | |
| 8 | 2 | FINDINGS | LOCALLY RECURRING TUMOR MASS NOT INDICATED, THE SAME AS PREVIOUS INSPECTION. | | |
| 9 | 2 | DIAGNOSIS | SAME AS PREVIOUS INSPECTION. OBVIOUS RECURRENCE NOT INDICATED. | | |
| ⋮ | ⋮ | ⋮ | ⋮ | | |

FIG. 4B

| ASSOCIATION ID | REPORT ITEM ID1 | REPORT ITEM ID2 | TYPE |
| --- | --- | --- | --- |
| 1 | 1 | 2 | CORRESPONDENCE ASSOCIATION |
| 2 | 2 | 3 | CAUSAL ASSOCIATION |
| 3 | 4 | 5 | CORRESPONDENCE ASSOCIATION |
| 4 | 5 | 6 | CAUSAL ASSOCIATION |
| 5 | 3 | 6 | CAUSAL ASSOCIATION |
| 6 | 7 | 8 | CORRESPONDENCE ASSOCIATION |
| 7 | 8 | 9 | CAUSAL ASSOCIATION |
| 8 | 10 | 11 | ADVERSARIAL ASSOCIATION |
| ⋮ | ⋮ | ⋮ | ⋮ |

FIG. 4C

| ASSOCIATION ID1 | ASSOCIATION ID2 |
| --- | --- |
| 1 | 6 |
| 2 | 7 |
| 10 | 17 |
| ⋮ | ⋮ |

FIG. 6A

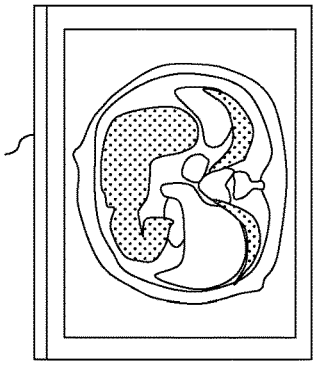

| PATIENT INFORMATION | |
|---|---|
| ID | AA123456789 |
| NAME | TARO SHIMOMA |
| SEX | MALE |
| AGE | 28 YEARS |
| DATE OF BIRTH | 6/23/1986 |

| ORDER INFORMATION | |
|---|---|
| DATE OF EXAMINATION | 8/23/2009 |
| SITE OF EXAMINATION | CHEST, ABDOMEN |
| MODALITY | CT WITHOUT CONTRAST ENHANCEMENT |
| COMMISSIONING DEPARTMENT | GASTROENTEROLOGICAL SURGERY |
| COMMISSIONING PHYSICIAN | JIRO KOSUGI |
| CONTENT OF REQUEST | LEFT KIDNEY / CONFIRMATION OF POSTOPERATIVE COURSE |

| SITE | FINDINGS | DIAGNOSIS | TREATMENT |
|---|---|---|---|
| | LEFT KIDNEY HAS BEEN ENUCLEATED, LOCALLY RECURRING TUMOR MASS NOT INDICATED. | CONFIRMATION OF POSTOPERATIVE COURSE → OBVIOUS RECURRENCE NOT INDICATED | |
| | SOFT TISSUE TUMOR MASS OBSERVED AT L1 CENTRUM, ACCOMPANIED BY OSTEOLYSIS. NO MARKED CHANGE FROM PREVIOUS TIME. | NO TENDENCY FOR METASTASIS TO LUMBUS TO INCREASE | |
| GALL BLADDER | SMALL HIGH-ABSORPTION AREA OBSERVED WITHIN GALL BLADDER. EXPANSION OF GALL BLADDER IS STRONG, AND WALL THICKENING IS MANIFESTED. | CONFIRMATION OF POSTOPERATIVE COURSE → GALLSTONE CHOLECYSTITIS IS SUSPECTED. | CONFIRMATION OF CLINICAL CONDITIONS, AND ADMINISTRATION OF TREATMENT AS NECESSARY IS DESIRED. |

Impression
LEFT KIDNEY HAS BEEN ENUCLEATED, LOCALLY RECURRING TUMOR MASS NOT INDICATED. NO TENDENCY FOR METASTASIS TO LUMBUS TO INCREASE. CHOLECYSTITIS IS SUSPECTED. CONFIRMATION OF CLINICAL CONDITIONS, AND ADMINISTRATION OF TREATMENT AS NECESSARY IS DESIRED.

[BASIC INPUT] [DETAILED INPUT] [LAYOUT] [TIME-SEQUENCE DISPLAY] [PAST REPORTS] [SAVE REPORT]

FIG. 18A
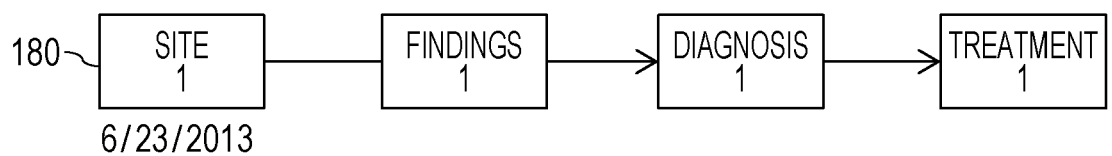
FIG. 18B
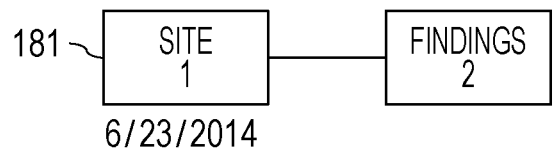
FIG. 18C1
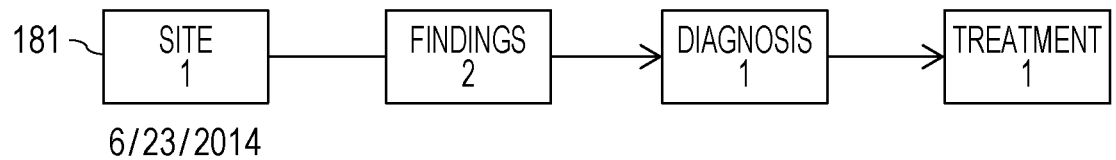
FIG. 18C2
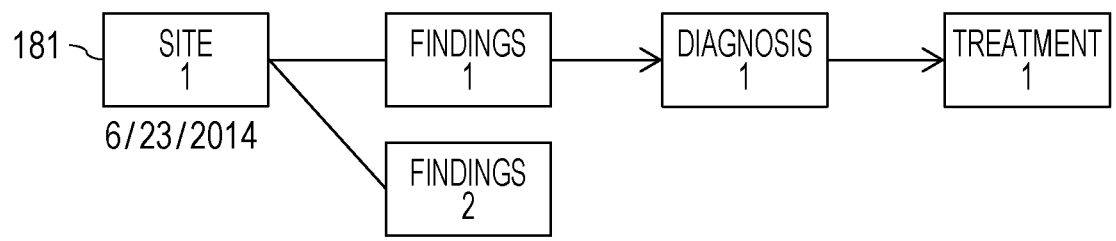

FIG. 28A

| REQUESTING ID | CONTENT OF REQUEST |
|---|---|
| 1 | CANCER OF LEFT KIDNEY, CONFIRMATION OF POSTOPERATIVE COURSE |
| 2 | SEARCH FOR METASTASIS |
| ⋮ | ⋮ |

| ITEM ID | REPORT ID | TYPE | CONTENT | REQUESTING ID |
|---|---|---|---|---|
| 1 | 1 | SITE |  | – |
| 2 | 1 | FINDINGS | LEFT KIDNEY HAS BEEN ENUCLEATED, LOCALLY RECURRING TUMOR MASS NOT INDICATED. | – |
| 3 | 1 | DIAGNOSIS | POSTOPERATIVE COURSE OF CANCER OF LEFT KIDNEY OBVIOUS RECURRENCE NOT INDICATED. | 1 |
| 4 | 1 | SITE |  | – |
| 5 | 1 | FINDINGS | SOFT TISSUE TUMOR MASS OBSERVED AT L1 CENTRUM, ACCOMPANIED BY OSTEOLYSIS. MO MARKED CHANGE FROM PREVIOUS TIME. | – |
| 6 | 1 | DIAGNOSIS | NO TENDENCY FOR METASTASIS TO LUMBUS TO INCREASE. | 1 |
| ⋮ | ⋮ | ⋮ | ⋮ | ⋮ |

FIG. 31

| IMAGE DIAGNOSIS REPORT |
|---|

| PATIENT INFORMATION | EXAMINATION INFORMATION | ORDER INFORMATION |
|---|---|---|
| PATIENT ID:<br>AA123456789<br>TARO SHIMOMARU<br>AGED 79 YEARS MALE | CT OF CHEST AND ABDOMEN<br>NO CONTRAST ENHANCEMENT<br>DATE OF EXAMINATION:<br>AUGUST 23, 2009 (SUNDAY) | CANCER OF LEFT KIDNEY<br>CONFIRMATION OF<br>POSTOPERATIVE COURSE |

《Findings》 DATE OF RADIOGRAM INTERPRETATION: AUGUST 25, 2009
REPLY TO COMMISSION PHYSICIAN PERFORMING RADIOGRAM DIAGNOSIS: GORO KAWASAKI CANCER OF LEFT KIDNEY
CONFIRMATION OF POSTOPERATIVE COURSE   IN COMPARISON WITH JULY 8, 2009

<PRIMARY TUMOR>
LEFT KIDNEY HAS BEEN ENUCLEATED,
LOCALLY RECURRING TUMOR
MASS NOT INDICATED.

POSTOPERATIVE COURSE
OF CANCER OF LEFT KIDNEY
OBVIOUS RECURRENCE
NOT INDICATED

<METASTATIS>
MULTIPLE NODES, BOTH LARGE IN
SMALL, OBSERVED IN BOTH LUNGS.
MO MARKED CHANGE
FROM PREVIOUS TIME.

NO TENDENCY FOR MULTIPLE
PULMONARY METASTASIS
TO INCREASE.

<METASTATIS>
SOFT TISSUE TUMOR MASS
OBSERVED AT L1 CENTRUM,
ACCOMPANIED BY OSTEOLYSIS.
MO MARKED CHANGE FROM PREVIOUS TIME.

NO TENDENCY FOR METASTASIS
TO LUMBUS TO INCREASE.

NO EXPANDING LESION INDICATED IN LIVER.
NO ABNORMALITIES OBSERVED IN
PANCREAS, SPLEEN, OR ADRENAL GLAND.
NO ENLARGEMENT OBSERVED
IN ABDOMINAL LYMPH NODES.
NO FLUID OBSERVED IN ABDOMEN.

OTHER CLINICALLY CRITICAL LESIONS

SMALL HIGH-ABSORPTION AREA
OBSERVED WITHIN GALL BLADDER.
EXPANSION OF GALL BLADDER IS STRONG,
AND WALL THICKENING IS MANIFESTED.

GALLSTONE
CHOLECYSTITIS IS SUSPECTED.

OTHER NON-PROBLEMATIC LESIONS

CIRCULAR LOW-ABSORPTION
REGION OBSERVED AT UPPER
EXTREMITY OF RIGHT KIDNEY.

KIDNEY CYST

《Impression》

LEFT KIDNEY CANCER HAS BEEN EXCISED, LOCALLY RECURRENCE NOT INDICATED.
THERE IS NO INCREASE IN METASTASIS TO LUNGS AND SPINE; IF BEING TREATED,
APPEARS TO BE UNDER CONTROL.
CHOLECYSTITIS IS SUSPECTED, SO CONFIRMATION OF CLINICAL CONDITIONS,
AND ADMINISTRATION OF TREATMENT AS NECESSARY IS DESIRED.

FIG. 32

| PATIENT INFORMATION | |
|---|---|
| ID | AA123456789 |
| NAME | TARO SHIMOMARU |
| SEX | MALE |
| AGE | 79 YEARS |
| DATE OF BIRTH | 3/4/1930 |

| ORDER INFORMATION | |
|---|---|
| DATE OF EXAMINATION | 8/23/2009 |
| SITE OF EXAMINATION | CHEST, ABDOMEN |
| MODALITY | CT WITHOUT CONTRAST ENHANCEMENT |
| COMMISSIONING DEPARTMENT | GASTROENTEROLOGICAL SURGERY |
| COMMISSIONING PHYSICIAN | JIRO KOSUGI |
| | LEFT KIDNEY |
| CONTENT OF REQUEST | CONFIRMATION OF POSTOPERATIVE COURSE |

PAST (7/8/2009)

Findings: ⋮

Impression: ⋮

KEY IMAGE

CURRENT (8/23/2009)

Findings: ⋮
LEFT KIDNEY HAS BEEN ENUCLEATED, LOCALLY RECURRING TUMOR MASS NOT INDICATED. OBVIOUS RECURRENCE NOT INDICATED.
SOFT TISSUE TUMOR MASS OBSERVED AT L1 CENTRUM, ACCOMPANIED BY OSTEOLYSIS.
NO MARKED CHANGE FROM PREVIOUS TIME. *NO TENDENCY FOR METASTASIS TO LUMBUS TO INCREASE.*
⋮

Impression: ⋮
LEFT KIDNEY CANCER HAS BEEN EXCISED, LOCALLY RECURRENCE NOT INDICATED. THERE IS NO INCREASE IN METASTASIS TO LUNGS AND SPINE; IF BEING TREATED, APPEARS TO BE UNDER CONTROL.
⋮

KEY IMAGE

MOUSE CURSOR

HIGHLIGHT FRAMES

FIG. 33

| | 06/23/2013 11:52:00 | 09/12/2013 15:32:00 | 12/25/2013 12:30:00 |
|---|---|---|---|
| TUMOROUS LESION AT PERIPHERY OF POSTERIOR SEGMENT OF RIGHT LUNG S2 | [TUMOROUS LESION AT PERIPHERY OF POSTERIOR SEGMENT OF RIGHT LUNG S2] | [TUMOROUS LESION AT PERIPHERY OF POSTERIOR SEGMENT OF RIGHT LUNG S2] | [TUMOROUS LESION AT PERIPHERY OF POSTERIOR SEGMENT OF RIGHT LUNG S2] |
| LESION/EVENT | TUMOROUS LESION | TUMOROUS LESION | TUMOROUS LESION |
| SITE | PERIPHERY OF POSTERIOR SEGMENT OF RIGHT LUNG S2 | PERIPHERY OF POSTERIOR SEGMENT OF RIGHT LUNG S2 | PERIPHERY OF POSTERIOR SEGMENT OF RIGHT LUNG S2 |
| SIZE | AROUND 18 mm | AROUND 21 mm | AROUND 23 mm |
| DENSITY | PARTIAL CALCIFICATION | PARTIAL CALCIFICATION | PARTIAL CALCIFICATION |
| SHAPE | LOBULATED | LOBULATED | LOBULATED |
| SURROUNDINGS | CONTRACTING | CONTRACTING | CONTRACTING |
| REPRESENTATIVE IMAGE | IMAGE  IMAGE | IMAGE  IMAGE | IMAGE  IMAGE |

FIG. 34

| VOCABULARY (SET) 1 | VOCABULARY (SET) 2 | TYPE OF ASSOCIATION | PROBABILITY (%) |
|---|---|---|---|
| CANCER, PRIMARY | METASTASIS | CAUSATIVE ASSOCIATION | 50.0 |
| CANCER, LARGE INTESTINE | CANCER, LUNGS | ADVERSARIAL ASSOCIATION | 50.0 |
| CARDIOGENIC, PLEURAL EFFUSION | BLOOD SAMPLING, CARDIAC FUNCTIONS | CAUSATIVE ASSOCIATION | 68.4 |
| CANCER, STOMACH, PRIMARY | METASTASIS, LIVER | CAUSATIVE ASSOCIATION | 78.9 |
| ⋮ | ⋮ | ⋮ | ⋮ |

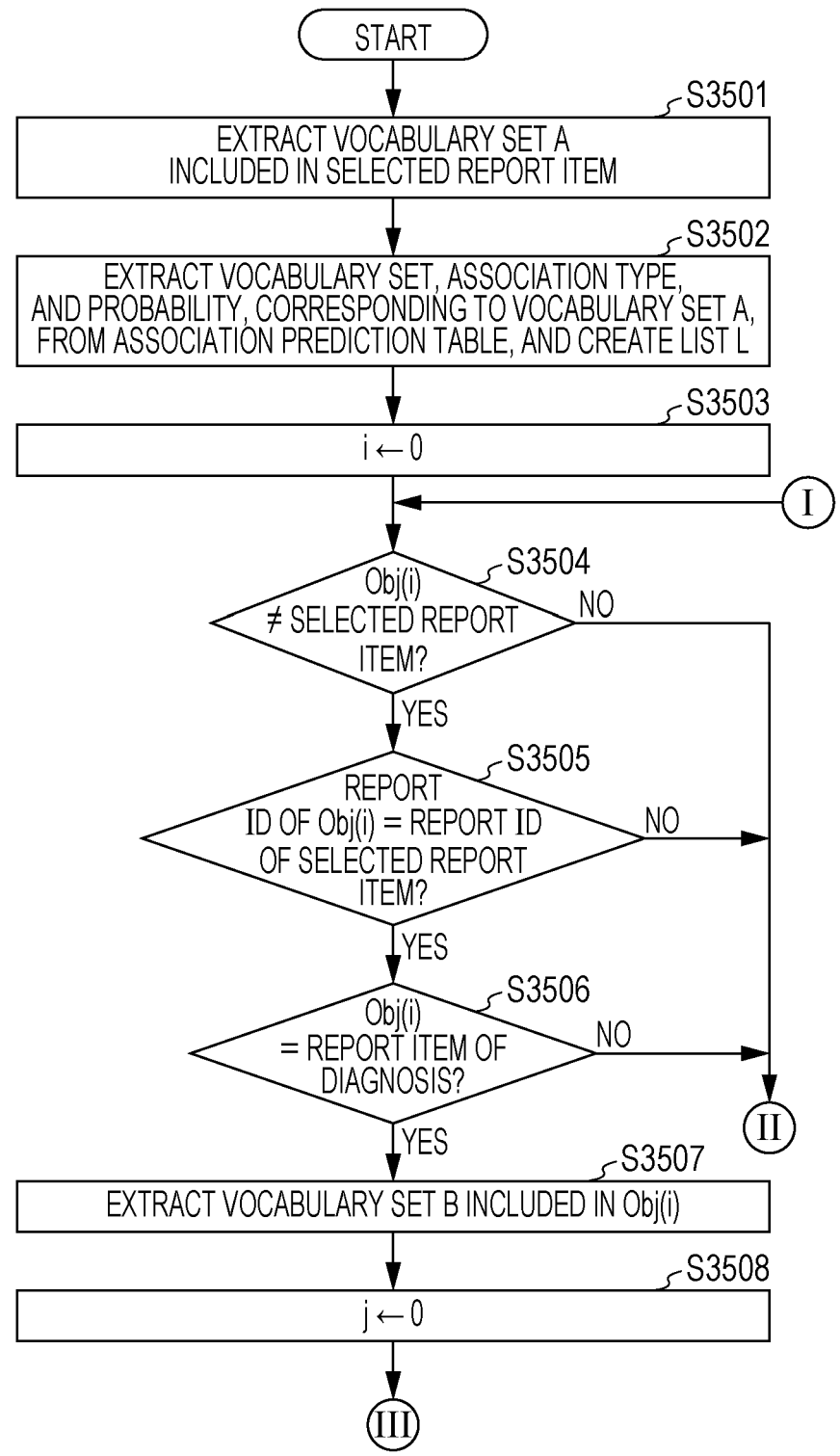

FIG. 41B

| SITE | FINDINGS | DIAGNOSIS | TREATMENT |
|---|---|---|---|
| ... ... | MULTIPLE ENLARGEMENTS FOUND AT RIGHT RENAL LYMPH NODES. SIZES ARE 15 TO 20 mm, CONSIDERED TO BE A SIGNIFICANT SIZE. | LYMPHADENOMA IS SUSPECTED. | |

PATIENT INFORMATION ......
ORDER INFORMATION ......

| SITE | FINDINGS | DIAGNOSIS | TREATMENT |
|---|---|---|---|
| ... ... | MULTIPLE ENLARGEMENTS FOUND AT RIGHT RENAL LYMPH NODES. SIZES ARE ** TO ** mm, CONSIDERED TO BE A SIGNIFICANT. | ********* IS SUSPECTED. | |

PATIENT INFORMATION ......
ORDER INFORMATION ......

| SITE | FINDINGS | DIAGNOSIS | TREATMENT |
|---|---|---|---|
| 4201 | MALIGNANT LESION AROUND 25 mm OBSERVED AT UPPER LOBE OF LEFT LUNG. IRREGULAR IN SHAPE AND APPEARING LOBULAR. INVASION TO BRONCHUS, ARTERIES, AND VEINS OBSERVED. INTERIOR INDICATES SOFT TISSUE DENSITY, WITHOUT CLEAR CALCIFICATION. 4205 | LUNG CANCER CANNOT BE RULED OUT. | 4207 |
| 4202 | | MULTIPLE PULMONARY METASTASIS SUSPECTED | |
| 4203 | TUMOROUS LESION AROUND 20 mm OBSERVED AT PERIPHERY OF POSTERIOR SEGMENT OF RIGHT LUNG S2. LOBULAR AND ACCOMPANIED BY CONTRACTION OF SURROUNDINGS. PARTIAL CALCIFICATION. | POSSIBILITY OF CANCER OF LARGE INTESTINE SHOULD BE CONSIDERED. | 4208 |
| 4204 | NO SIGNIFICANT ENLARGEMENT OF LYMPH NODES OBSERVED. | MULTIPLE PULMONARY METASTASIS SUSPECTED 4206 | |

FIG. 42B

| SITE | FINDINGS | DIAGNOSIS | TREATMENT |
|---|---|---|---|
| | MALIGNANT LESION AROUND 25 mm OBSERVED AT UPPER LOBE OF LEFT LUNG. IRREGULAR IN SHAPE AND APPEARING LOBULAR. INVASION TO BRONCHUS, ARTERIES, AND VEINS OBSERVED. INTERIOR INDICATES SOFT TISSUE DENSITY, WITHOUT CLEAR CALCIFICATION. | LUNG CANCER CANNOT BE RULED OUT. | 4209 4210 |
| | | MULTIPLE PULMONARY METASTASIS SUSPECTED | |
| | TUMOROUS LESION AROUND 20 mm OBSERVED AT PERIPHERY OF POSTERIOR SEGMENT OF RIGHT LUNG S2. LOBULAR AND ACCOMPANIED BY CONTRACTION OF SURROUNDINGS. PARTIAL CALCIFICATION. | POSSIBILITY OF CANCER OF LARGE INTESTINE SHOULD BE CONSIDERED. | |
| | NO SIGNIFICANT ENLARGEMENT OF LYMPH NODES OBSERVED. | MULTIPLE PULMONARY METASTASIS SUSPECTED | |

| SITE | FINDINGS | DIAGNOSIS | TREATMENT |
|---|---|---|---|
| 4201 | MALIGNANT LESION AROUND 25 mm OBSERVED AT UPPER LOBE OF LEFT LUNG, IRREGULAR IN SHAPE AND APPEARING LOBULAR. INVASION TO BRONCHUS, ARTERIES, AND VEINS OBSERVED. INTERIOR INDICATES SOFT TISSUE DENSITY, WITHOUT CLEAR CALCIFICATION. | LUNG CANCER CANNOT BE RULED OUT. | 4207 |
| 4202 | | MULTIPLE PULMONARY METASTASIS SUSPECTED | |
| 4203 | TUMOROUS LESION AROUND 20 mm OBSERVED AT PERIPHERY OF POSTERIOR SEGMENT OF RIGHT LUNG S2. LOBULAR AND ACCOMPANIED BY CONTRACTION OF SURROUNDINGS. PARTIAL CALCIFICATION. | POSSIBILITY OF CANCER OF LARGE INTESTINE SHOULD BE CONSIDERED. | 4208 |
| 4204 | NO SIGNIFICANT ENLARGEMENT OF LYMPH NODES OBSERVED. | MULTIPLE PULMONARY METASTASIS SUSPECTED 4206 | |

| SITE | FINDINGS | DIAGNOSIS | TREATMENT |
|---|---|---|---|
| | MALIGNANT LESION AROUND 25 mm OBSERVED AT UPPER LOBE OF LEFT LUNG, IRREGULAR IN SHAPE AND APPEARING LOBULAR. INVASION TO BRONCHUS, ARTERIES, AND VEINS OBSERVED. INTERIOR INDICATES SOFT TISSUE DENSITY, WITHOUT CLEAR CALCIFICATION. | LUNG CANCER CANNOT BE RULED OUT. 4401 4402 | 4209 |
| | | MULTIPLE PULMONARY METASTASIS SUSPECTED | |
| | TUMOROUS LESION AROUND 20 mm OBSERVED AT PERIPHERY OF POSTERIOR SEGMENT OF RIGHT LUNG S2. LOBULAR AND ACCOMPANIED BY CONTRACTION OF SURROUNDINGS. PARTIAL CALCIFICATION. | POSSIBILITY OF CANCER OF LARGE INTESTINE SHOULD BE CONSIDERED. 4301 | |
| | NO SIGNIFICANT ENLARGEMENT OF LYMPH NODES OBSERVED. | MULTIPLE PULMONARY METASTASIS SUSPECTED | |

APPARATUS, METHOD, SYSTEM, AND PROGRAM FOR CREATING AND DISPLAYING MEDICAL REPORTS

BACKGROUND

Field

Aspects of the present invention generally relate to an apparatus, method, system, and program for recording diagnoses.

Description of the Related Art

In the medical field, there are cases where treatment is performed using medical reports that include names of diseases identified based on medical images, treatment strategies, etc. The increase in medical images used for treatment has led to an increase in the amount of work to create such medical reports.

Japanese Patent Laid-Open No. 2007-140862 describes, with regard to all existing reports that have been databased, creating network information based on the number of times of associated word combinations, displaying a partial structure from the network information based on extraction conditions specified by the user, and enabling the user to select words from the partial structure that is displayed, thereby supporting creation of medical reports.

There are cases where parts of medical reports created in the past are duplicated and used when creating a new medical report. If there is a description logically associated with a description to be duplicated, there are cases where this is duplicated at the same time, so users have had to confirm the entire content of medical reports created in the past.

SUMMARY OF THE INVENTION

According to some embodiments of the present invention, an information processing apparatus includes a creating unit configured to create a medical report including a plurality of sets of information that is the object of diagnosis and association information indicating associations among a plurality of items included in each of the plurality of sets of information, a specification unit configured to specify one item out of a plurality of items included in each of a plurality of sets of information included in a previously created medical report stored in a storage unit, an identifying unit configured to identify, based on association information by which the specified one item is associated, at least one item of the plurality of items included in the previously created medical report, in response to specification by the specification unit, and a display control unit configured to display the at least one identified item on a screen for editing the medical report.

Further features of aspects of the present invention will become apparent from the following description of exemplary embodiments with reference to the attached drawings.

BRIEF DESCRIPTION OF THE DRAWINGS

FIGS. 4A through 4C are diagrams illustrating examples of database formats for items and associated information making up a medical report.

FIGS. 18A through 18C2 are first diagrams for describing processing relating to duplication according to an eighth embodiment.

FIGS. 28A and 28B are diagrams illustrating examples of database formats for items and associated information making up a medical report according to the twelfth embodiment.

FIG. 31 is a diagram illustrating an example of layout screen.

FIG. 32 is an example of highlighted display in an unstructured radiogram interpretation report.

FIG. 33 is a diagram illustrating an example of a time-series information window screen.

FIG. 34 is a diagram illustrating an example of an association prediction table.

FIGS. 35A and 35B are diagrams illustrating an example of a flowchart showing procedures of processing at the time of the user creating or selecting a report item for diagnosis.

FIGS. 41A and 41B are diagrams illustrating an example of processing according to the fourth embodiment.

FIGS. 42A and 42B are diagrams illustrating an example of processing according to a third embodiment.

FIGS. 43A and 43B are diagrams illustrating an example of processing according to the third embodiment.

FIGS. 44A and 44B are diagrams illustrating an example of processing according to the third embodiment.

DESCRIPTION OF THE EMBODIMENTS

An apparatus according to embodiments of the present invention will be described below. First, the configuration of the apparatus common to the embodiments and the concept of medical reports created by the apparatus according to the embodiments of the present invention will be described by way of example in FIGS. 1 through 6B and 30A through 33.

In a first embodiment, all items directly or indirectly associated with items specified in medical reports created in the past are identified, and can be used in a newly created medical report. An example is provided in FIGS. 8, 11, 36, 37, and 38.

In a second embodiment, association information among items can be acquired from the type of item specified. An example is provided in FIG. 7.

In a third embodiment, if there are items with a mutually exclusive association, a recommendation frame corresponding thereto can be displayed. An example is provided in FIGS. 34, 35, and 42A through 44B.

In a fourth embodiment, at the time of duplicating and using contents described in a medical report created in the past, the duplicated contents and display form can be optimized for the duplicate at the point of the series of processing relating to duplication having been completed. An example is provided in FIGS. 12, 13, 40, 41A, and 41B.

In a fifth embodiment, part of items correlated with an item specified by a specification unit can be identified and duplicated. Also, upon identifying and duplicating the part, parts not duplicated can be easily duplicated later, and individually duplicated items can be associated. An example is provided in FIGS. 9, 10A, 10B, 14, 15, and 39.

In a sixth embodiment, a range of duplication can be identified according to the type of specified items.

In a seventh embodiment, a range of duplication from a medical record created in the past can be identified in accordance with the object for which creation of a medical report has been ordered. An example is provided in FIGS. 16A through 17B.

In an eighth embodiment, a range of duplicating from a report created in the case can be identified in accordance with the state of description of a newly created medical report or content regarding which description is assumed. An example is provided in FIGS. 18A through 20.

In a ninth embodiment, evaluation values, based on association information, are imparted for each of the report items, and a range of duplication can be identified in accordance with the evaluation values. An example is provided in FIGS. 21 and 22.

In a tenth embodiment, evaluation values, based on association information, are imparted for each of the report items, and a range of duplication can be identified in accordance with the evaluation values. An example is provided in FIGS. 23 through 25.

In an eleventh embodiment, techniques for identifying a range of duplication can be switched over. An example is provided in FIG. 26.

Figure 29:
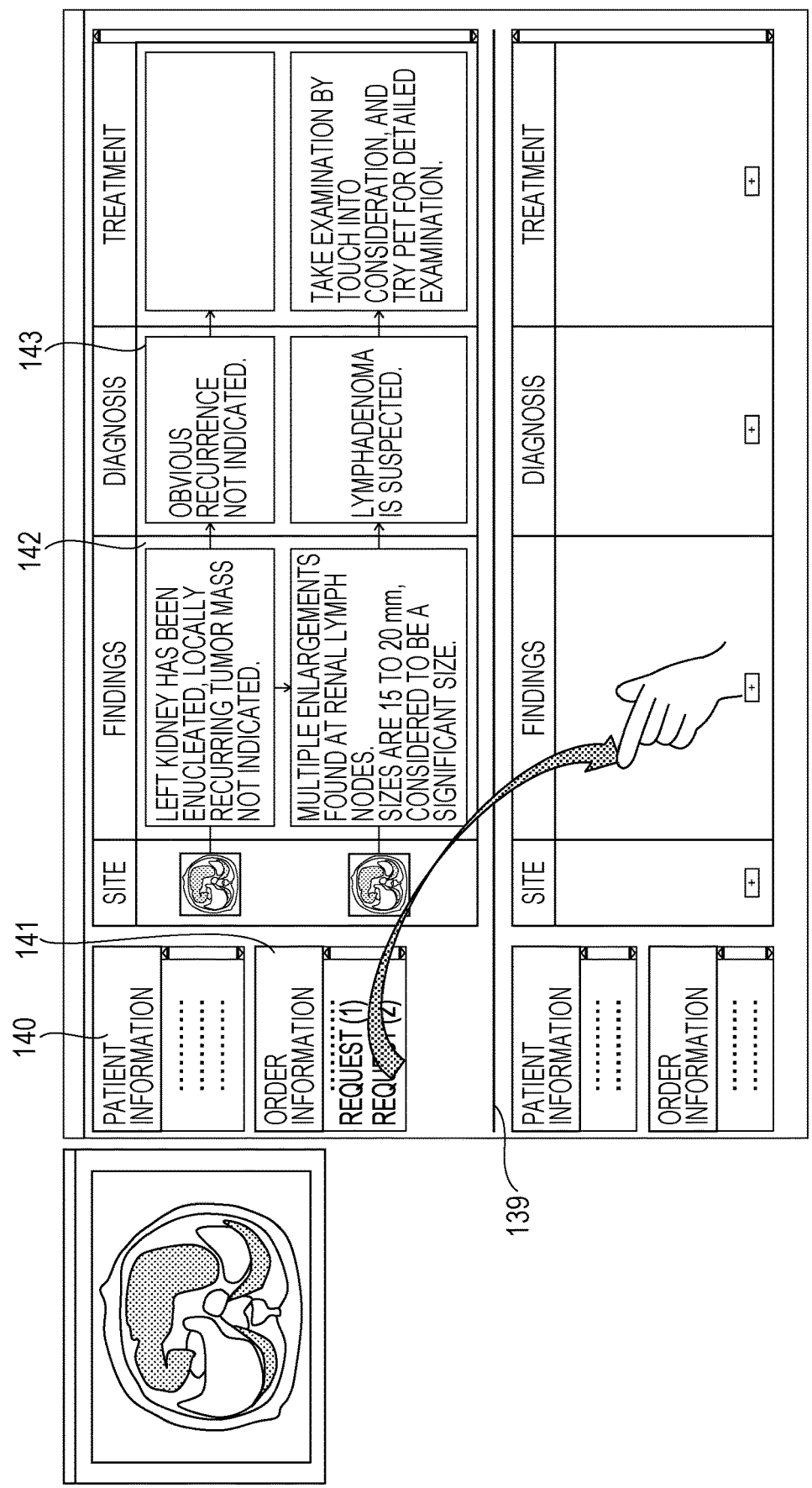
FIG. 29 is a diagram illustrating an example of a conceptual diagram of ordering object selection processing in the twelfth embodiment.

In a twelfth embodiment, the object of order for creation of a medical report created in the past can be duplicated in a newly created medical report, thereby identifying items corresponding to the object of order for creation of the medical report created in the past, and duplicating in the newly created medical report. An example is provided in FIGS. 27 through 29.

The above-described embodiments will now be described in detail. In the medical field, treatment is performed using images acquired by various types of imaging apparatuses and various types of examinations. Image data acquired by imaging apparatuses will be referred to as "medical images". Images obtained by image data subjected to imaging processing or the like to obtain images suitable for diagnosis are also included in medical images. Examples of such imaging apparatuses include, but are not limited to, computed tomography (CT), magnetic resonance imaging (MRI), digital radiography (DR) where radiographic apparatuses take two-dimensional radiograms, etc.

An example of image data acquired by a CT apparatus will be described as an example. The CT apparatus acquires one-dimensional distribution of relative X-ray absorption coefficient values, called CT values, as image data. Thereafter, the image data is subjected to processing called image reconstruction, thereby obtaining three-dimensional images. These three-dimensional images are further subjected to maximum intensity projection (MIP) to create MIP images, or used to acquire two-dimensional images of desired slices.

These image data, three dimensional images, and various types of images acquired from the three dimensional images, are all included in "medical images".

Diagnosis using medical images is called "radiogram interpretation". Radiogram interpretation is performed by a physician who specializes in diagnostic imaging observing medical images. When a primary physician of the object of diagnosis issues an order instructing imaging of medical images and radiogram interpretation, a technician takes appropriate medical images, and provides these medical images for radiogram interpretation. Information and advice obtained based on the acquired medical images and information regarding the object of diagnosis are communicated from the specializing physician to the primary physician.

Note that in the following description, the physician ordering radiogram interpretation will be referred to as an "ordering physician", while the physician who specializes in diagnostic imaging will be referred to as a "radiogram interpretation physician". In many cases, an ordering physician is a clinician, especially a primary physician. Radiogram interpretation reports are managed as electronic data. Radiogram interpretation reports can be described and managed within electronic medical records. In a separate example, radiogram interpretation reports are recorded on a medium such as paper, and thus managed.

A radiogram interpretation report includes information called "findings", where a physician has observed the acquired medical image of the patient and described discovered events and phenomena, and "diagnosis", where suspected diseases or the like are described based on the content of the findings. There are cases where information describing advice to the ordering physician, such as treatment strategy, etc., is included.

Moreover, medical images are attached to a radiogram interpretation report. Medical images can be substituted by thumbnail images of the medical images, information for referencing the medical images, etc. The findings and diagnoses, and association therebetween, are often described in natural language or described in different ways depending on the physician creating the report. Accordingly, there have been cases where the ordering physician required time to comprehend the content of the radiogram interpretation report.

In recent years, there a technique has been proposed where radiogram interpretation reports are created in a structured manner, expressing the association among multiple items included in the information regarding medical images such as findings and diagnoses, which is information regarding diagnosis described in radiogram interpretation reports. Each of the items includes the content that the radiogram interpretation physician has input. Accordingly, for example, the association between multiple findings and diagnoses described in radiogram interpretation reports can be clearly expressed. Structuring radiogram interpretation reports reduces the work load on the radiogram interpretation physician creating the reports, and also makes the content easier for the ordering physician to comprehend.

A radiogram interpretation physician creates association information associating the input items as necessary when describing in a radiogram interpretation report, and creates a structured radiogram interpretation report. Such structured radiogram interpretation reports can be created by a radiogram interpretation report creating support system according to exemplary embodiments of the present invention.

First Embodiment

Figure 1:
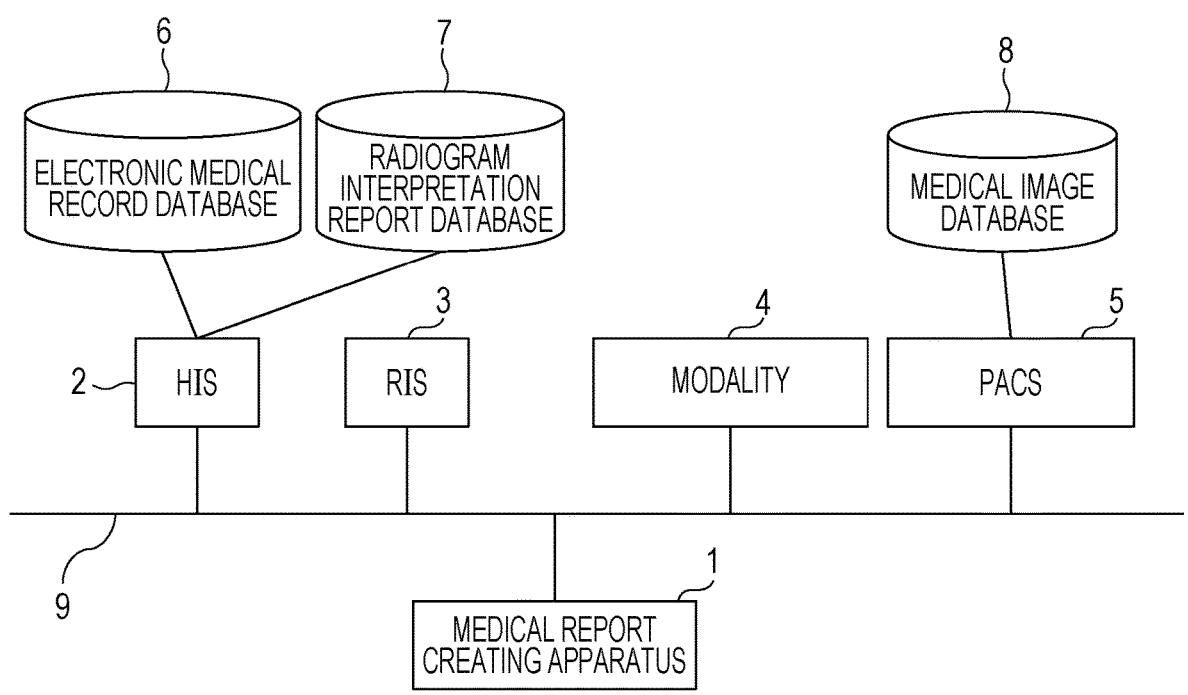
FIG. 1 is a diagram illustrating an example of the configuration of a medical report creating apparatus.

FIG. 1 is a configuration diagram of a medical report creating apparatus. The medical report creating apparatus 1 is an apparatus for a radiogram interpretation physician to view images for radiogram interpretation and to create radiogram interpretation reports. The medical report creating apparatus 1 is connected with an in-hospital system by an in-hospital local area network 9. Examples of other information systems connected to the in-hospital system include a hospital information system (HIS) 2, a radiology information system (RIS) 3, a modality 4, and a picture archiving and communication system (PACS) 5.

The HIS 2 is a comprehensive system including a medical office accounting system, treatment registration system, treatment information system, etc. The HIS 2 includes an electronic medical record database 6 and a radiogram interpretation report database 7. The electronic medical record database 6 stores an electronic medical record recording medical history of patients.

The RIS 3 is a system for making reservations for examinations and treatment by radiology equipment, management of examination results, inventory control of materials, etc. There are cases where the radiogram interpretation report database 7 is managed by the RIS 3. Examples of the modality 4 include, but are not limited to, CT apparatuses, MRI apparatuses, ultrasound diagnosis apparatuses, positron-emission tomography (PET) apparatuses, DR apparatuses, etc. The PACS 5 is a system for electronically saving, searching, and performing communication of medical images acquired by the modality 4. The PACS 5 includes a medical image database 8 as a destination to save medical images.

Figure 2:
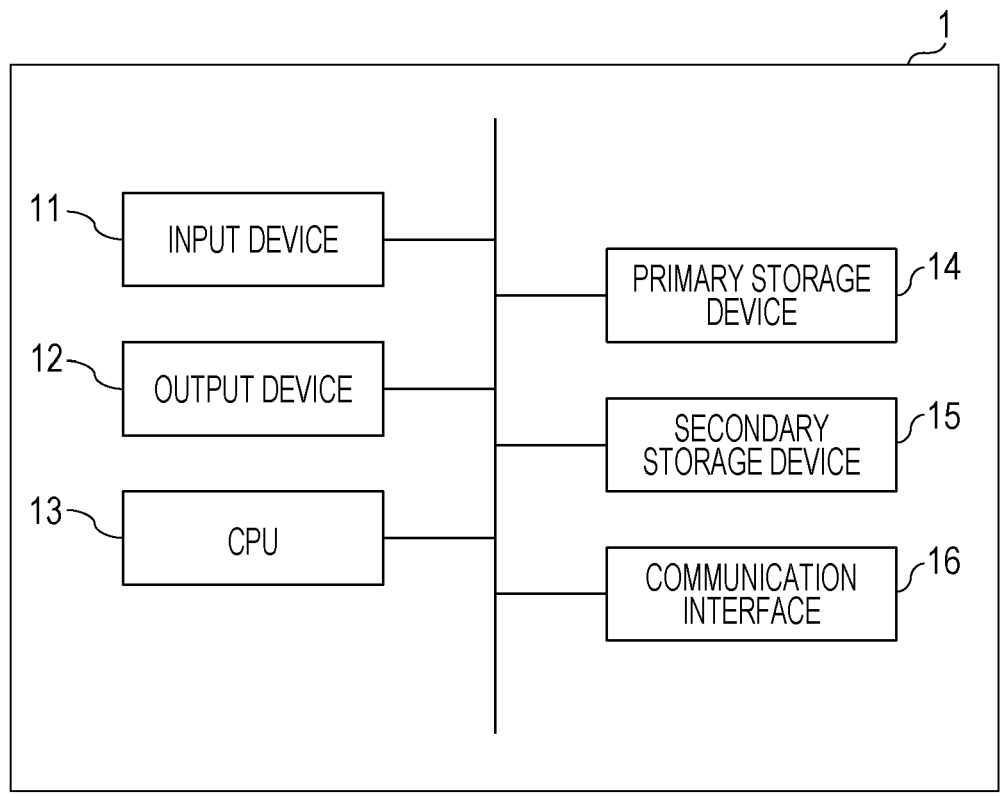
FIG. 2 is a diagram illustrating an example of the configuration of a medical report creating apparatus.

FIG. 2 illustrates a specific configuration diagram of the medical report creating apparatus 1. An input device 11 is, for example, a mouse, digitizer, keyboard, etc., and is used to input user instructions to the medical report creating apparatus. An output device 12 is, for example, a light-emitting diode (LED) panel, liquid crystal panel, etc., to display the state of apparatus, processing contents, and so forth.

A central processing unit (CPU) 13 reads programs saved in a secondary storage device 15 to a primary storage device 14. The CPU 13 further executes the programs that have been read in, and performs calculation(s), thereby centrally controlling the apparatus, and also controlling display of a user interface (UI). The primary storage device 14 is primarily memory such as random access memory (RAM), etc. The secondary storage device 15 stores a medical report creating program for operating the medical report creating apparatus 1. Examples of the secondary storage device 15 include, but are not limited to, storage media such as hard disks, flash memory, etc.

Typically, the capacity of the primary storage device 14 is less than the capacity of the secondary storage device 15, with the secondary storage device 15 storing programs, data, etc., that the primary storage device 14 cannot contain. The secondary storage device 15 is also used for long term storage. A communication interface 16 is connected to the in-hospital local area network 9, and serves as a communication interface with various in-hospital systems, as well as the HIS 2, RIS 3, modality 4, and PACS 5.

Figure 3:
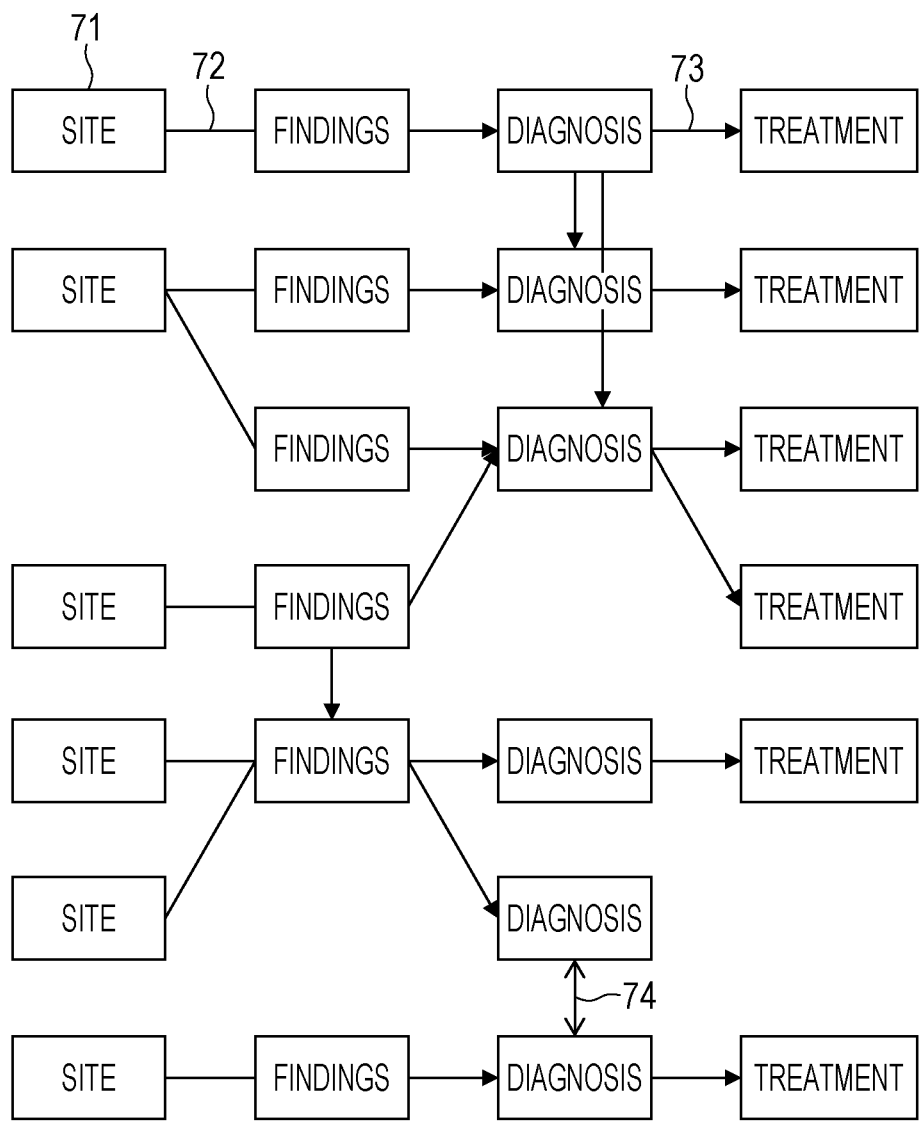
FIG. 3 is a diagram illustrating an example of a concept of a report created by a medical report creating apparatus.

FIG. 3 is a diagram illustrating an example of a concept of a report created by the medical report creating apparatus according to an exemplary embodiment of the present invention. A medical report includes multiple sets of information to be diagnosed, and association information indicating associations among multiple items included in each of the multiple sets of information. The multiple sets of information for diagnosis include, for example, four types of information: site, findings, diagnosis, and treatment.

Sentences and images enabling the site of the body to be identified are input to the report item included in the site information. One of the report items included in the site information is denoted by a frame 71 in FIG. 3. An image input to the site report item is, for example, a soft copy of the image to be diagnosed or address information to access an image for radiogram interpretation. A soft copy of the image for diagnosis can be a thumbnail image of this image. Parameters, etc., for image processing to be applied when viewing the image, examination information such as imaging region and apparatus information from when the image was acquired, can be input as well at this time.

A findings report item has sentences describing one or more lesions input thereto. A diagnosis report item has sentences describing one or more diseases input thereto. A treatment report item has sentences describing one or more treatments input thereto. Examples of association information include, but are not limited to, correspondence association, causal association, exclusive association, progress-related association indicating time-series association, etc., in accordance with association among report items.

In FIG. 3, correspondence associations are indicated by lines 72, causal associations are indicated by arrows 73, and an exclusive association is indicated by a double-headed arrow 74. A correspondence association refers to two report items being associated with each other. A causal association refers to two report items being associated by cause-and-effect. The direction of the arrow indicates the direction from the causative item to the result item. An exclusive association indicates that two reports are adversarial, denoting that the contents of the two report items cannot be established at the same time.

Report items in an exclusive association denote that the contents of neither of the reports items could be concluded to be unsuitable at the point of creating the report, but at least one is expected to be found unsuitable over the course of diagnosis and accordingly deleted. One report item can have association information with multiple other report items, i.e., the association among report items is many-to-many.

Figure 5:
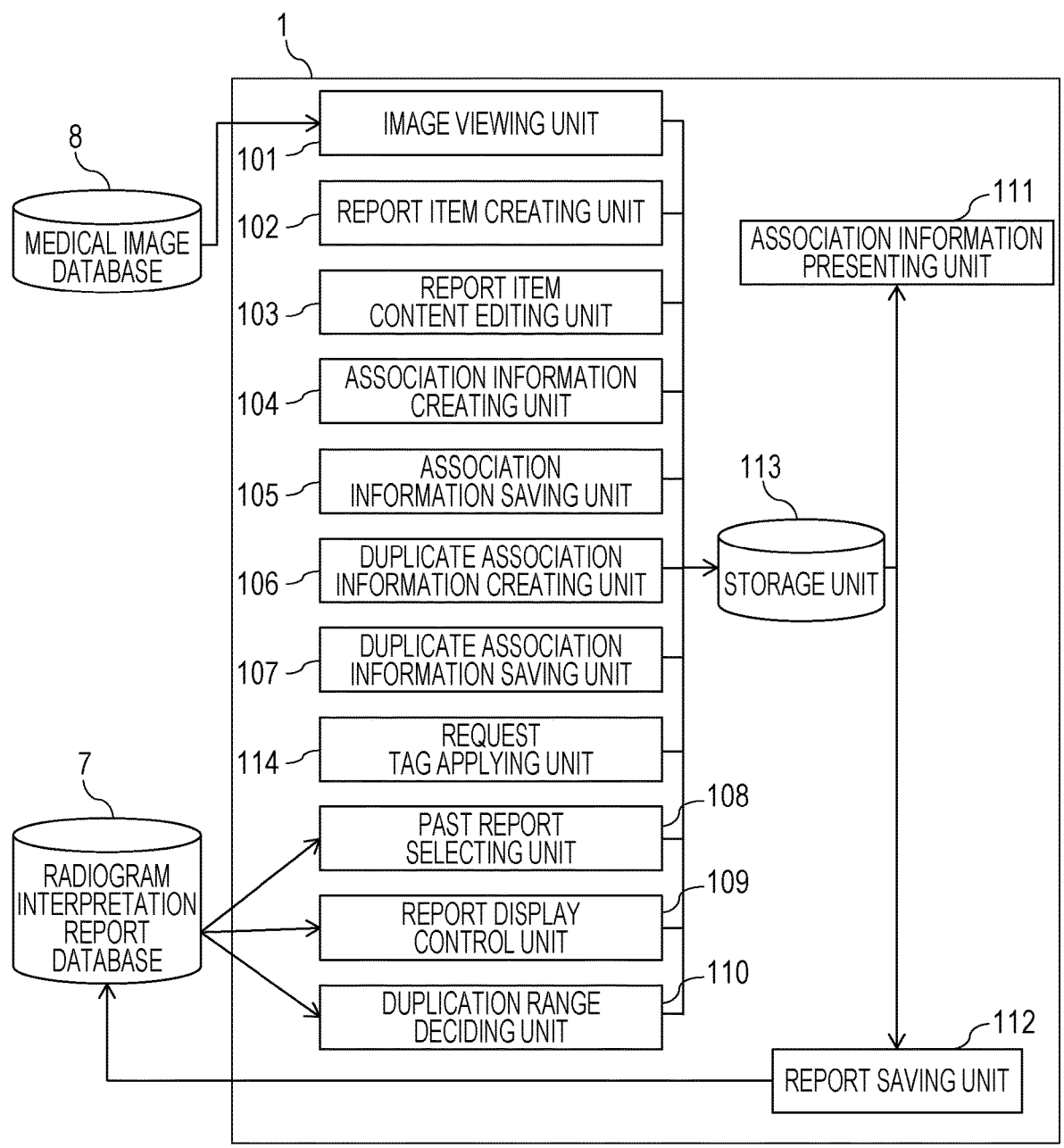
FIG. 5 is a diagram illustrating an example of functions of a medical report creating apparatus.
Figure 6:
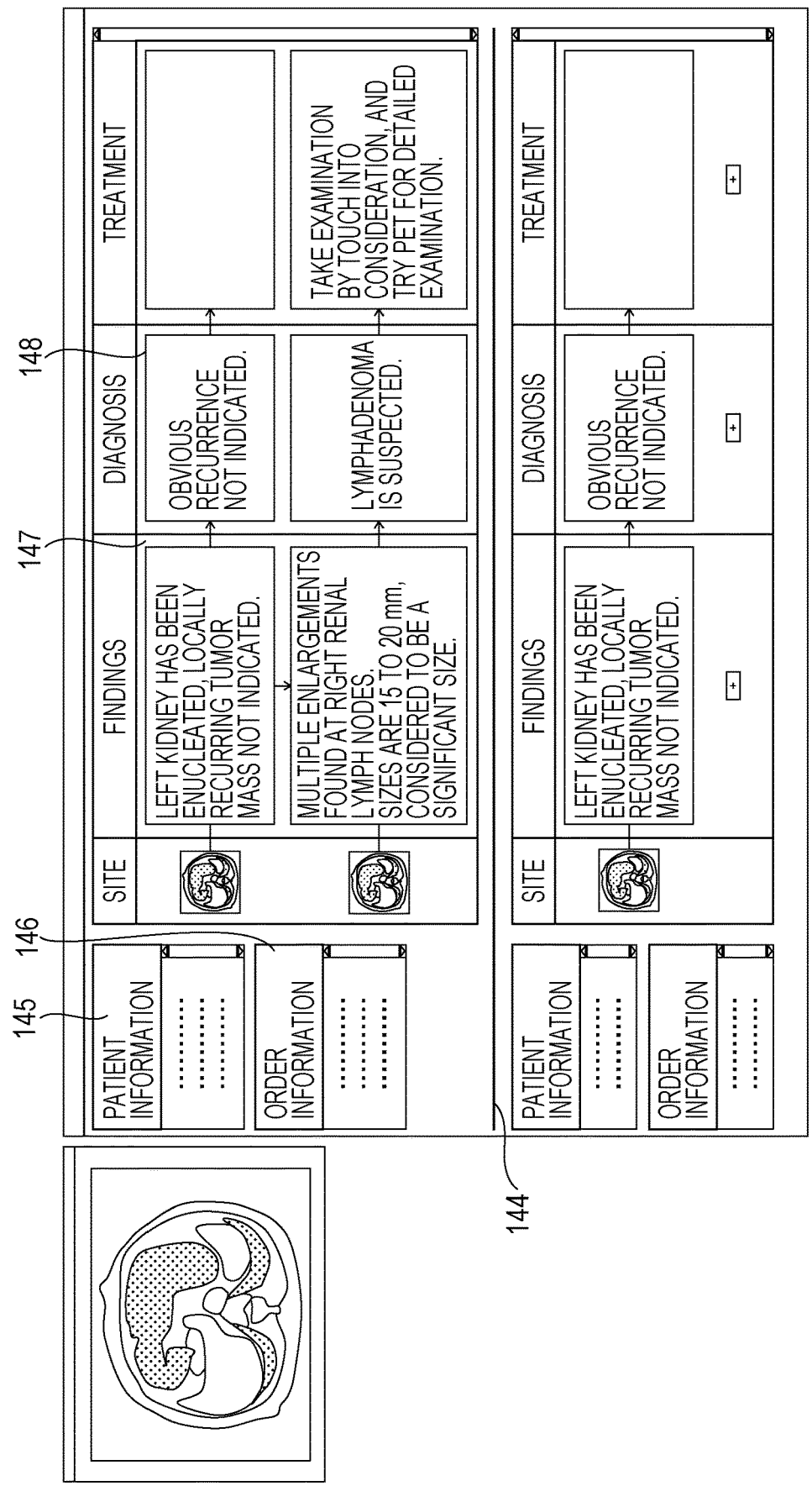
FIGS. 6A and 6B are diagrams illustrating an example of a graphical user interface (GUI) of a medical report creating apparatus.

FIG. 5 is a functional block diagram describing primary functions of the medical report creating apparatus 1. An image viewing unit 101 reads out images for radiogram interpretation from the medical image database 8 via the PACS 5, and displays the images on the output device 12. The image viewing unit 101 also executes various types of processing relating to image viewing, such as changing displayed images, image processing, etc., in response to operations via the input device 11 by the radiogram interpretation physician.

A report display control unit 109 displays an editing screen on the output device 12 to newly create a report or displays past reports on the output device 12 in accordance with operations by the radiogram interpretation physician. A report item creating unit 102 creates report items and provides item IDs uniquely identifying the report IDs. The report item creating unit 102 also automatically provides report IDs to uniquely identify a report to which a report item belongs, the type of information for diagnosis to which the report item belongs, and saves them in an item table 701 illustrated in FIG. 4A.

A report item content editing unit 103 edits the content of a report item in accordance with content input by the radiogram interpretation physician via the input device 11, and saves the edited results in the relevant location in the item table 701. An association information creating unit 104 creates association information among selected report items. The association information includes an association ID for uniquely identifying association information, the IDs of two report items associated by this association information, and the type of association. The association information creating unit 104 displays a screen for a user to select the type of association from among report items on the output device 12. The association information creating unit 104 acquires the type of association from among the report items that the user has input.

An association information saving unit 105 saves the association information created by the association information creating unit 104 in an association table 702 illustrated in FIG. 4B. In a case where the type of association is a causal association, the item ID of the report item indicating the cause is set to report item ID1, the item ID of the report item indicating the result is set to report item ID2, and saved. A request tag applying unit 114 applies a selected word or sentence representing the content of a request included in the order to a selected report item as a request tag, and saves the result in the item table 701. One report item can include multiple request tags. The contents of the request are communication items from the ordering physician requesting the radiogram interpretation physician to create the radiogram interpretation report. The contents of the order include, but are not limited to, the contents of the request, symptoms of the patient, names of diagnoses suspected by the ordering physician, etc.

An arrangement can be made where the ordering physician inputs the contents of the order divided into individual items beforehand. This enables the radiogram interpretation physician to select the input contents of requests as request tags for each report item. Alternatively, an arrangement can be made where a sentence expressing multiple contents of the order contained therein is manually or automatically divided into individual items. Applying such request tags enables corresponding report items to be shown for each of the contents of the request.

A past report selecting unit 108 displays a list of reports created in the past (hereinafter referred to as "past reports"), and selects reports to be used in a newly created report (hereinafter referred to as "current report"), in accordance with operations of the radiogram interpretation physician at the input device 11. The list of past reports is extracted based on values of report IDs in the item table 701. Based on information corresponding to the report IDs, a list of reports relating to all report IDs, a list of reports relating to the patient that is currently the object, a list of reports created in the past by a certain radiogram interpretation physician, etc., can also be displayed.

The report display control unit 109 displays the contents of past reports selected by a user. A duplication range deciding unit 110 decides, from the items (site, findings, diagnosis, treatment, association information, etc.) making up the reports displayed by the report display control unit 109, a range to be duplicated in the current report. The duplication range deciding unit 110 is a specification unit that, upon receipt of a user operation, specifies items included in past reports. The duplication range deciding unit 110 is also an identifying unit that, based on the specified items and association information, identifies items included in past reports. The duplication range deciding unit 110 also duplicates items identified in the current report.

The processing relating to duplication is carried out, based on information of the duplication range decided at the duplication range deciding unit 110, by the above-described report item creating unit 102, association information creating unit 104, association information saving unit 105, and a duplicate association information creating unit 106 and a duplicate association information saving unit 107. The duplicate association information creating unit 106 creates information indicating the association between original and duplicate information (hereinafter referred to as "duplicate association information") when duplicating items making up a past report are included in a newly created report. The duplicate association information saving unit 107 saves the duplicate association information created by the duplicate association information creating unit 106 in a duplicate association table 703 illustrated in FIG. 4C. The association ID1 and association ID2 are association IDs in the association table 702, and are saved so that association ID1 is the association ID of the original and association ID2 is the association ID of the duplicate.

An association information presenting unit 111 displays the association of the report items on the output device 12 following the contents of the association table 702 and duplicate association table 703. A report saving unit 112 saves the contents of the item table 701, association table 702, and duplicate association table 703, as report data in the radiogram interpretation report database 7 read in via the HIS 2. The format of report data is not limited to any specific format as long as information equivalent to that in the item table 701, association table 702, and duplicate association table 703 are included. For example, the information can be converted into a report data format defined by eXtensible Markup Language (XML), etc.

A storage unit 113 temporarily stores the item table 701, association table 702, and duplicate association table 703. The report item ID, report ID, and association ID are assigned to be sequential when saved in the item table 701 and association table 702.

FIGS. 6A and 6B are diagrams illustrating the overview of a GUI of the medical report creating apparatus 1. FIG. 6A illustrates an example of a report input screen. An image that is the object of diagnosis, for radiogram interpretation, is displayed in a medical image viewing screen 131. The radiogram interpretation physician performs operation input on the contents displayed in the medical image viewing screen 131 to realize the functions of the image viewing unit 101. A patient information display area 132 displays patient information that is the subject of the image to be diagnosed. Examples of patient information include, but are not limited to, a patient ID uniquely identifying the patient, patient's name, patient's age, patient's clinical history, etc.

An order information display area 133 displays information of the ordering department, such as examinations previously ordered, contents of the order, etc., from the ordering physician. A report creating area 134 is divided into the areas of site, findings, diagnosis, and treatment, each including a report item input frame 135 for input of content of the report item included in each information, and an input frame addition button 136 to add an input frame.

A report item input frame 135 is correlated with one report item, and accepts operation input for editing the content thereof. The functions of the report item content editing unit 103 are realized through operations at the report item input frame 135. The functions of the report item creating unit 102 are realized by operation input of pressing the input frame addition button 136, thereby creating a new report item. At the same time, a report item input frame 135 is displayed corresponding to the created report item. An input frame addition button 136 is provided for each type of item, and a report item of the type corresponding to the pressed button is created.

Addition of an input frame can be performed by key operations at the input device 11. For example, a diagnosis report item can be created by a user pressing the TAB key while editing the content of a findings report item. In the same way, a user can, for example, create a separate findings report item by pressing the RETURN key twice in succession while editing the contents of the findings report item. The report item input frame 135 is selected at the input device 11. Multiple input frames can be selected at the same time.

At the time of drag-and-drop of a selected input frame to another input frame, the association information creating unit 104 determines that this is operation input instructing association between a report item corresponding to the drag source input frame and a report item corresponding to the drag destination input frame. The association information creating unit 104 displays in accordance with the operation input instructing association a dialogue box to select the type of association. The association information presenting unit 111 displays the association between the report items as a line connecting report item input frames 135 in the report creating area 134.

In a case where the type of association is a correspondence association, the input frames are displayed as being connected by a simple line. In a case where the type of association is a causal association, the input frames are displayed as being connected by an arrow, from the input frame of the report item that is the cause to the input frame of the report item that is the result. In a case where the type of association is an exclusive association, the input frames of the two or more mutually exclusive report items are displayed as being connected by a double-headed arrow.

Upon an image being dragged and dropped from the medical image viewing screen 131 to the report creating area 134, the functions of the report item creating unit 102 create a report item contained in the information of the site, and display the input frame of this report item. At the same time, a report item for findings having a correspondence association with the site report item that was created is created, and this input frame is displayed.

In addition, in a case of drag-and-drop of an image from the medical image viewing screen 131 to an already-existing report item input frame 135, a soft copy of the image is registered as the content of the report item at the drop target. In a case of drag-and-drop of a request tag from the order information display area 133 to a report item input frame 135, the functions of the request tag applying unit 114 are executed, and the request tag of the drag source is applied to the report item at the drop target. In the following embodiments, the request tags are displayed above each of the report item input frames 135 so that the contents of the request tags applied to each report item can be comprehended.

An impressions input area 139 displays a summary of the report in the form of text. The text is input at the input device 11 by the radiogram interpretation physician. The content of the impressions input area 139 can be automatically created based on the content of the report creating area 134 and inserted here as text. For example, the contents of diagnosis and treatment report items can be automatically input as text.

At this time, when a cursor passes over a portion of the impressions input area 139, the report item corresponding to the content described at the cursor position can be displayed highlighted. A highlighted display includes, for example, changing the color of the input frame or the width of the lines of the input frame of the report item so as to be different from other items, causing the input frame of the report item to blink, etc.

Upon a past report button 137 being pressed, the processing of the past report selecting unit 108 is executed, and a list of past reports is displayed. The radiogram interpretation physician selects a report from the list of the reports at the input device 11, whereby the past report selected by the processing of the report display control unit 109 is displayed. The screen in FIG. 6B is an example of a result of screen transition due to performance of processing by the report display control unit 109.

Below a boundary line 144 in FIG. 6B the content in FIG. 6A before the screen transition is displayed, displaying the patient information display area 132, order information display area 133, report creating area 134, report item input frame 135, and input frame addition button 136, relating to the report currently being created. The radiogram interpretation physician can perform the same input operations as in the screen in FIG. 6A in the region below the boundary line 144. Although an example is illustrated in FIG. 6B where the objects such as buttons and input frames denoted by reference numerals 138 through 144 are not displayed, from the perspective of screen efficiency, these can be display as appropriate by a predetermined key operation.

The contents of the past report are displayed by the report display control unit 109 in the region above the boundary line 144. A patient information display area (past report) 145 shows information of the patient that is the object in the past radiogram interpretation report that has been selected. The patient information display area (past report) 145 is information described in the patient information display area 132 of the past report.

An order information display area (past report) 146 displays information of the ordering department, such as examinations that were ordered and the contents of the order made by the ordering physician when the past report was created. The order information display area (past report) 146 is information described in the order information display area 133 of the past report. A past report items and association information display area 147 is a region displaying report items making up the past report and associations among the report items.

Input in past report item input frames 148 are contents of report items making up the past report. A past report item input frame 148 is read-only, and the content(s) thereof cannot be edited by the report item content editing unit 103. In the same way as the report creating area 134, the past report items and association information display area 147 has a layout where the areas for site, findings, diagnosis, and treatment are divided and displayed. A desired range of the contents displayed in the past report items and association information display area 147 are duplicated and used by the radiogram interpretation physician in the newly created report.

Specific procedures of duplication processing will be described in detail in the description of the embodiments. The past report button 137 is a toggle button enabling a user to switch between the display of FIG. 6B and the display of FIG. 6A by operating the button.

Figure 30A:
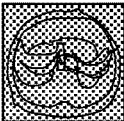
FIGS. 30A and 30B are diagrams illustrating examples of a basic input mode screen.
Figure 30B:
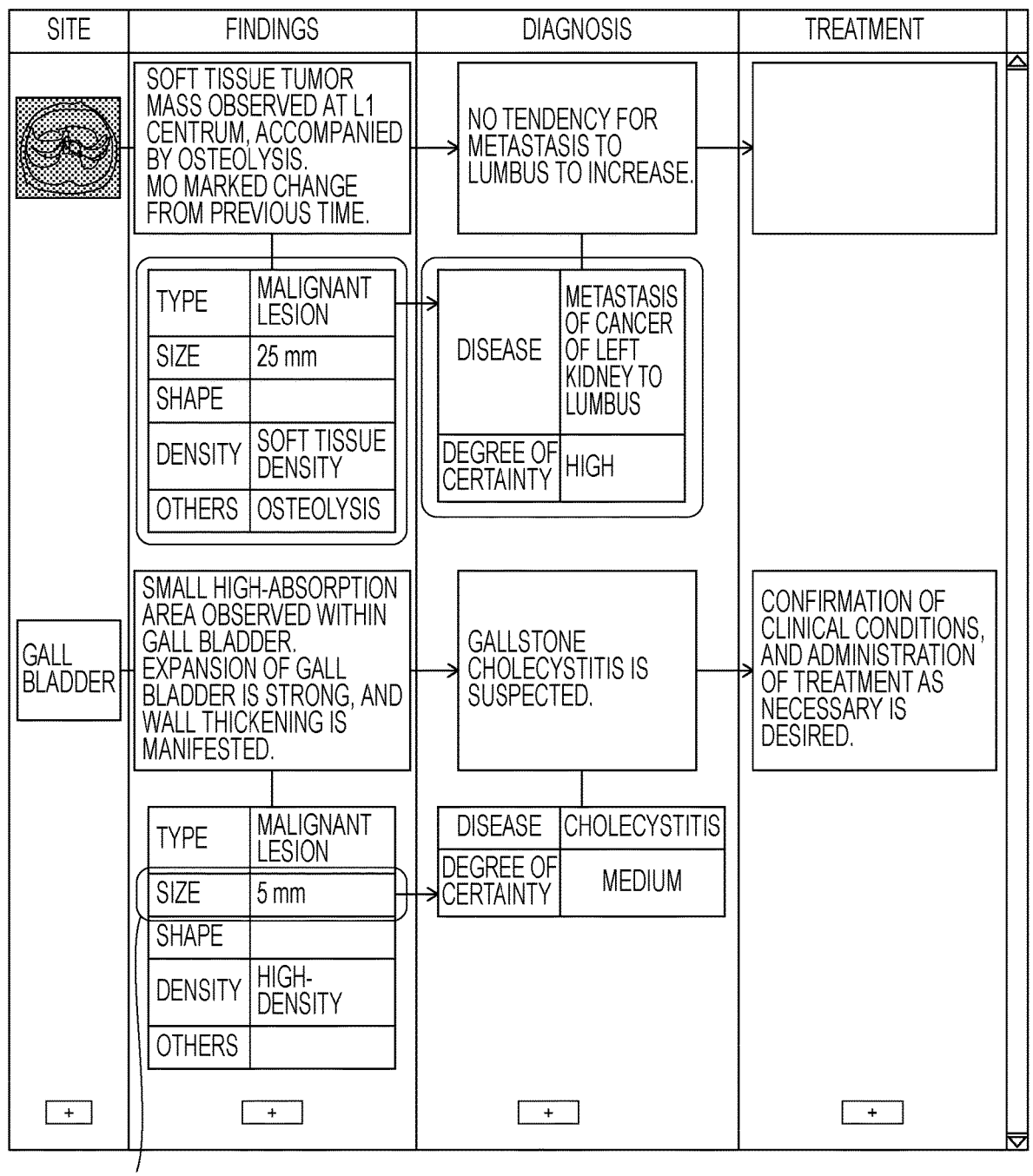

Upon a basic input screen display button 140 being pressed, the report display control unit 109 switches the display of the report creating area 134 to a basic input mode. FIG. 30A shows an example of a screen in the basic input mode. The contents of the findings, diagnosis, and treatment report items can be input in natural language in the basic input mode. When a detailed input screen display button 141 is pressed, the report display control unit 109 switches the display of the report creating area 134 to a detailed input mode. FIG. 30B shows an example of a screen in the detailed input mode. A display is made in the detailed input mode so that the contents of report items can be input as a correspondence table of values and attributes. A list can be displayed at this time for selection of information indicating attributes to enable association with other report items and attributes. This enables more detailed associations to be expressed.

An arrangement can also be made where, when switching from the basic input mode to the detailed input mode, attributes and values are automatically extracted from the natural language. Conversely, an arrangement can be made where, when switching from the detailed input mode to the basic input mode, natural language is automatically generated from the attributes and values in the correspondence table.

Upon a layout display button 142 being pressed, the report display control unit 109 creates a layout and displays the contents of the report creating area 134 and impressions input area 139. FIG. 31 shows an example of a layout screen. Items that have request tags applied, i.e., report items created as responses to the requests, are laid out in higher order. Labels, based on the contents of the item table 701 and association table 702 indicating the association among items are created and displayed.

For example, in a case where a description is made in the diagnosis of cancer, and there is also a causal association with another diagnosis, prediction is made that this is primary cancer or metastatic cancer and labels are displayed for each. In a case where there are combinations of multiple primary and metastatic cancers, such as in a case of double cancer, each combination can be distinguished by label name or color. The layout method can be changed by the ordering physician viewing the report, the device used for viewing, etc. For example, as illustrated in FIG. 32, display can be made in the form of an unstructured radiogram interpretation report format. In doing so, items associated with a selected item can be displayed highlighted to facilitate comprehension thereof.

For mobile terminals, for example, the report items can be displayed being sequentially switched. The basic input screen display button 140, detailed input screen display button 141, and layout display button 142 operate exclusively as radio buttons, and operations are performed with the screen being switched. An arrangement can be made where multiple buttons can be pressed at the same time to display multiple screens at the same time.

When a time-series display button 143 is pressed, the report display control unit 109 displays a time-series information window. The time-series information window displays the contents of the report items selected in the report creating area 134 in order of examination date. The contents displayed in the time-series information window are switched according to whether in basic input mode or detailed input mode. FIG. 33 illustrates an example of the screen of the time-series information window in the detailed input mode.

An image representing the site can be displayed regardless of the report item selected in the report creating area 134. Association information among report items with different examination dates is applied at the same time of duplication of report items performed in the screen in FIG. 6B. That is, association information indicating the time-series association is automatically applied to report items of the past report at the original and the report items at the duplicate in the current report. An arrangement can also be made where the user manually applies time-series association in a state where the past report and current report are displayed. The functions of the report saving unit 112 are executed in accordance with the operation input of pressing a report saving button 138.

Thus, the medical report creating apparatus 1 structures the report so that, for example, the associations among site, findings, diagnosis, and treatment are indicated by the report items being connected by lines and arrows. This enables the flow of logic indicating the connection of site, diagnosis, and treatment to be expressed in an easy to understand manner.

Next, processing of using the medical report creating apparatus 1 according to the first embodiment to duplicate the contents of a past report in a current report will be described in detail with reference to FIGS. 8, 11, 36, and 37.

Figure 8:
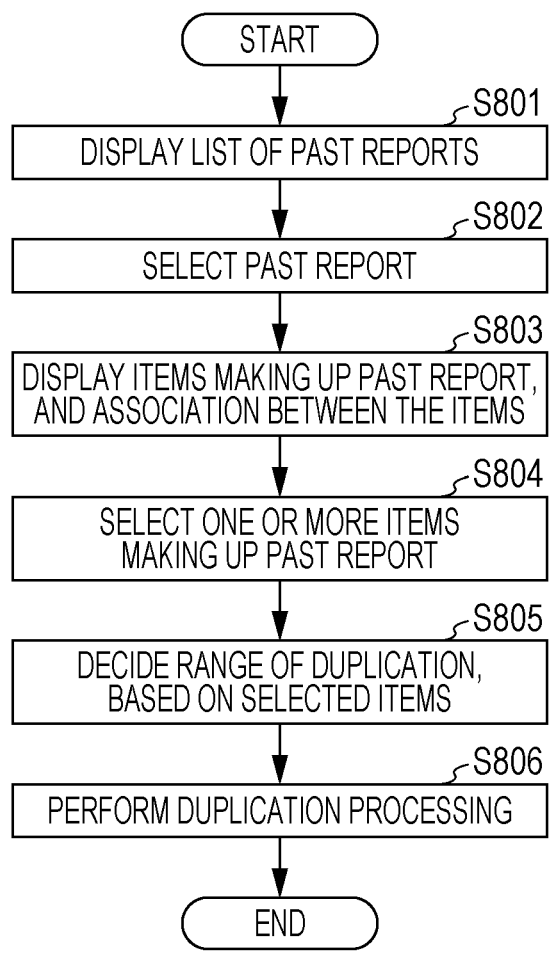
FIG. 8 is a diagram illustrating an example of procedures for processing to duplicate items and association information making up a past report.

FIG. 8 is a flowchart illustrating processing to duplicate and use, in a current report, report items and association information making up a past report. S801 and S802 are executed by the past report selecting unit 108. In S801, a list of past reports is displayed. The medical report creating apparatus 1 connects to the HIS 2 via the communication interface 16, and acquires a list of radiogram interpretation reports described in the past that are, for example, accumulated in the radiogram interpretation report database 7. Reports are acquired and displayed by specifying conditions to acquire just reports relating to a patient who is the object of the current radiogram interpretation, for example, using a database querying language such as Structured Query Language (SQL), etc.

In S802, a report ID identifying a past report selected by a user performing selection of reports at the input device 11 is transmitted to the report display control unit 109. An arrangement can be made where the past report selecting unit 108 estimates suitable past reports in accordance with the information in the current report, and performs the processing of S801 and S802 automatically. In S803, the report display control unit 109 displays, based on the report ID transmitted from the S802, the report items making up the past report and the association information among the report items. Specifically, records where the report IDs match the report IDs that have been transmitted are extracted from the item table 701, and the contents of the report items in this past report are displayed at the output device 12. At the same time, association information regarding association of the report items in the past report are extracted from the association table 702, and the relevant past report and the association information among the report items are displayed by the association information presenting unit 111.

In S804, the duplication range deciding unit 110 accepts selection of report items via input at the input device 11, and acquires report item IDs identifying the selected report items. In S805, the duplication range deciding unit 110 identifies, based on the obtained report item ID, the report items and association information to be duplicated in the current report. In S806, the items identified in S805 are displayed in the editing screen for the current report by the duplication range deciding unit 110, and duplicated in the current report by the report item creating unit 102, association information creating unit 104, association information saving unit 105, duplicate association information creating unit 106, and duplicate association information saving unit 107.

Figure 36:
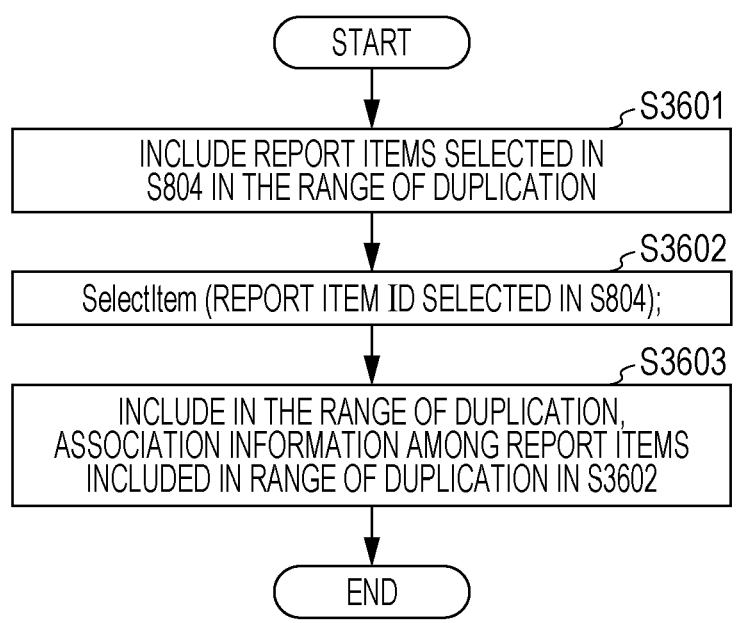
FIG. 36 is a flowchart illustrating an example of processing at a duplication range deciding unit according to a first embodiment.

FIG. 36 is a flowchart exemplifying processing to identify items to be included in the duplication range in the first embodiment. In S3601, the duplication range deciding unit 110 identifies report items specified in S804 as items that are to be at least included in the duplication range. That is, the report items selected in S804 are included in the duplication range. In S3602, the duplication range deciding unit 110 executes a function SelectItem, described in more detail below with respect to FIG. 37, using a report ID of a report item included in the duplication range in S3601 as an argument.

Figure 37:
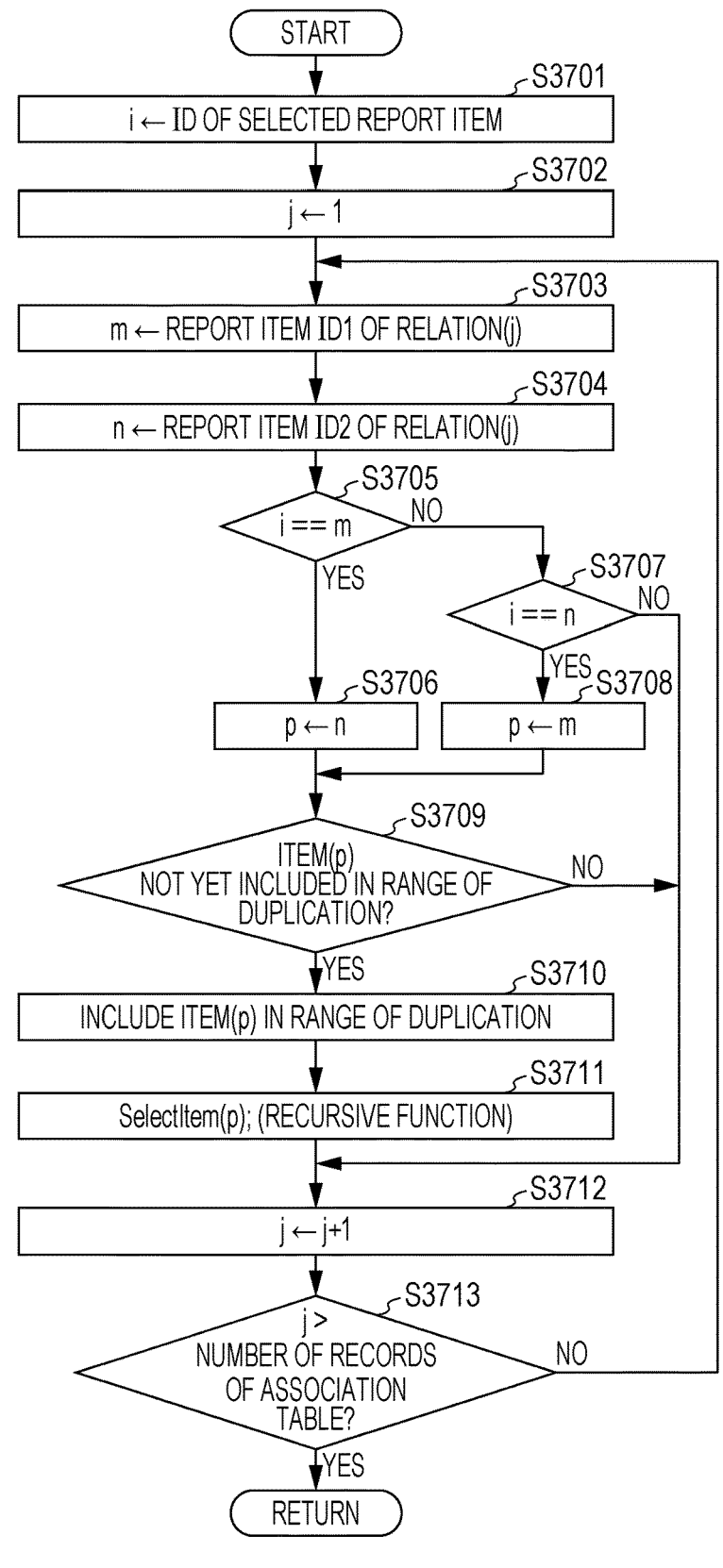
FIG. 37 is a diagram illustrating an example of processing at the duplication range deciding unit.

Turning to FIG. 37, the function SelectItem identifies an item associated with a certain item, and further identifies an item associated with the identified item. Accordingly, all items directly and indirectly associated with a certain item can be identified. The processing in the function SelectItem will be described next.

A report item of which the report ID is x can be referenced by function ITEM(x). Also, association information of which the association ID is x can be referenced by function RELATION(x). In S3701, the value of the report ID, that is the argument of the function SelectItem, is substituted into the variable i. In S3702, 1 is substituted into the variable j. In S3703, the report item ID1 of the association information obtained by RELATION(j) is substituted into the variable m. In S3704, the report item ID2 of the association information obtained by RELATION(j) is substituted into the variable n. In S3705, the value of variable i and variable m are compared.

If the values are the same, the flow advances to S3706, and if they are not, to S3707. In S3706, the value of variable n is substituted into the variable p, and the flow advances to S3709. In S3707, the values of variable i and variable n are compared. If these values are the same, the flow advances to S3708, and if they are not, to S3712.

In S3708, the value of variable m is substituted into variable p, and the flow advances to S3709. In S3709, determination is made whether ITEM(p) is not already included in the duplication range. In a case where the result of the determination is true, the flow advances to S3710. In a case where the result of the determination is false, the flow advances to S3712. In a case where the value of p is empty (null), the result of the determination is deemed to be false, and the flow advances to S3712.

In S3710, ITEM(m) is included in the duplication range, and the flow advances to S3711. In S3711, the function SelectItem is executed with the p that is the value of the report item ID as an argument. That is, the function SelectItem is recursively called up. In S3712, variable j is incremented. Determination is made in S3713 whether the value of variable j exceeds the number of records in the association table. In a case where the result of the determination is false, the flow returns to S3703, and the above processing repeats. In a case where the result of the determination in S3713 is true, the function SelectItem ends.

The processing of the function SelectItem exemplified in FIG. 37 involves performing the processing of S3703 through S3711 on all association information saved in the association table 702 in FIG. 4B. In another example, the processing of the function SelectItem is performed with the object of the processing in S3703 through S3711 narrowed down. That is, the association information in the association table 702 is narrowed down to the association information belonging to past reports where the report item ID1 and report item ID2 have both been selected in S804, and just the narrowed down association information is subjected to the processing in S3703 through S3711. This can improve processing speed.

In the processing of the function SelectItem exemplified in FIG. 37, the report item IDs specified as arguments of the function identify association information included in the association table 702 in the form of report item ID1 and report item ID2. An example of different processing for identifying such association information is processing using a graph structure. In S803 illustrated in FIG. 8, a graph structure among report items making up the past report are stored in the primary storage device 14, based on the items making up the past report and the item IDs and association IDs acquired at the time of displaying the association among the items. Then, based on this graph structure, report items directly or indirectly associated with the report item specified in S804 are identified. Specifically, a "report item" class expressing report items is defined by the program that operates the medical report creating apparatus 1. The class as identified here is according to the concept thereof in general object-oriented programming. The defined "report item" class has an array storing instances of the "report item" class as member variables thereof. That, in S803 the duplication range deciding unit 110 creates instances of the "report item" class corresponding to each report item to be displayed.

Instances of report items directly associated with report items corresponding to each instance are stored in the array that each instance has. Accordingly, an instance group is created beforehand as a graph structure, so when a report item is specified in S804, an array of an instance corresponding thereto can be referenced, and directly-associated report items can be efficiently identified. Recursively referencing instances stored in array corresponding to directly-associated report items enables report items indirectly associated with report items to be efficiently identified in S804.

Returning to FIG. 36, in S3603 the association information among report items identified as a duplication range in S3601 and S3602 is included in the duplication range. Specifically, association information of report items where both report item ID1 and report item ID2 have been identified in the duplication range is extracted from all records in the association table 702 and set as an object of duplication. In a case where the number of report items included in the duplication range is one, association information where the report item ID1 is the report item ID of the original, the report item ID2 is empty (null) and the type is empty (null), is set as association information to be duplicated. If there is no association information in the association table 702 where the report item ID1 is the report item ID of the original, the report item ID2 is empty (null) and the type is empty (null), a unique association ID is newly created and set as the object of duplication.

Figure 38:
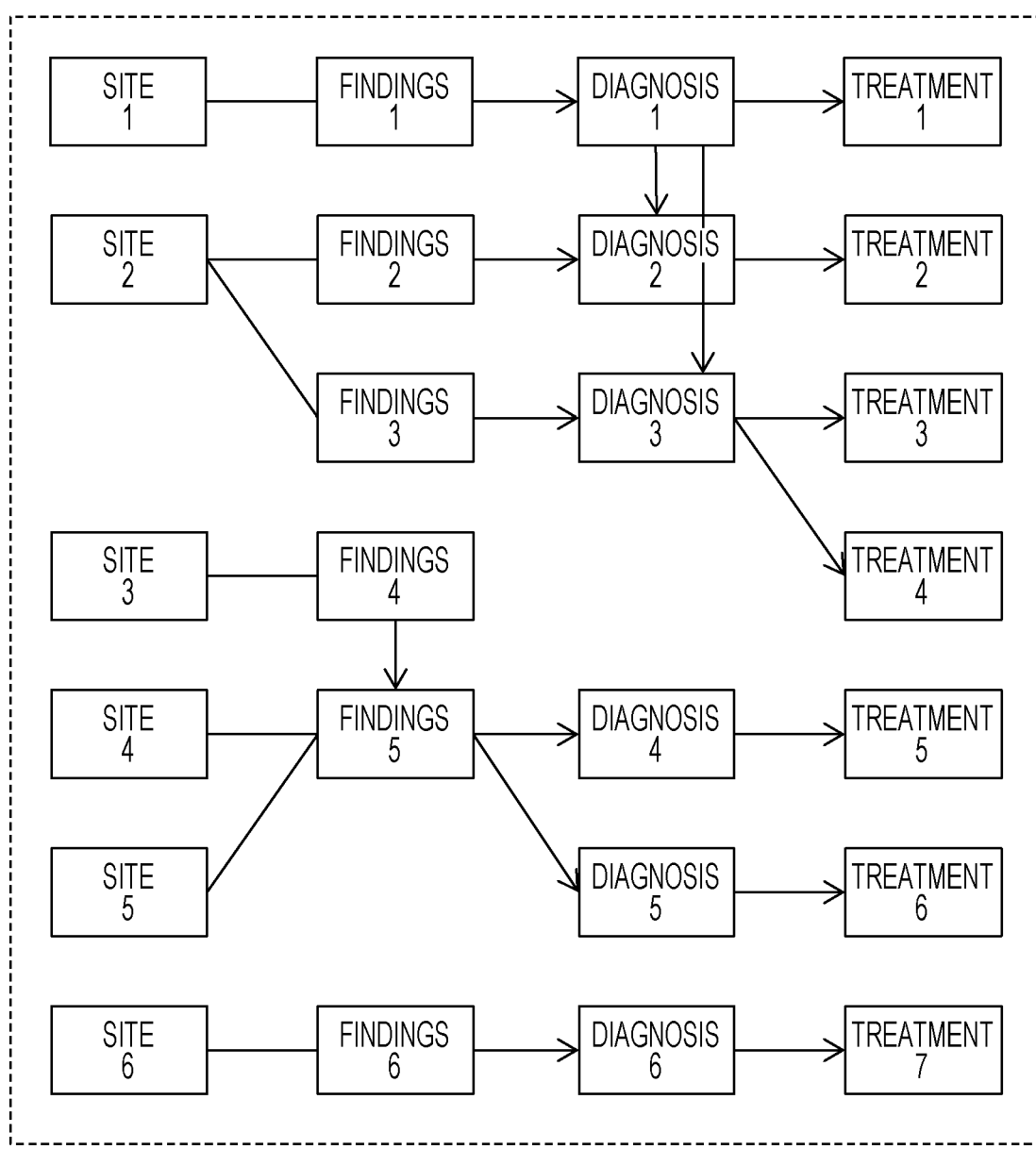
FIG. 38 is a diagram illustrating an example of processing relating to duplication according to the first embodiment.

A concept of items identified as the duplication range by the duplication range deciding unit 110 of the medical report creating apparatus 1 according to the first embodiment will be described with respect to FIG. 38. For example, in a case where an item findings 5 shown in FIG. 38 has been specified in S804 in FIG. 8, the duplication range will be site 3, findings 4, findings 5, site 4, site 5, diagnosis 4, treatment 5, diagnosis 5, and treatment 6, and the eight sets of association information that are the association information among these. In a case where item findings 5 and site 6 shown in FIG. 38 have both been specified at the same time in S804 in FIG. 8, the duplication range will be site 3, findings 4, findings 5, site 4, site 5, diagnosis 4, treatment 5, diagnosis 5, and treatment 6, in accordance with the findings 5 having been first specified as a report item, and the eight sets of association information that are the association information among these are included in the duplication range.

In accordance with site 6 having been specified, site 6, findings 6, diagnosis 6, and treatment 7, and the three sets of association information that are the association information among these are included in the duplication range. Upon the duplication range being identified by the duplication range deciding unit 110, the report display control unit 109 displays the identified items in the editing screen for the current report. That is, the report display control unit 109 functions as a display control unit.

Whether to duplicate the items identified by the duplication range deciding unit 110 as the duplication range in the current report is determined in accordance with user operation input. For example, in a case where a user selects one item included in a past report, the report display control unit 109 displays a screen on the output device 12 for the user to instruct whether to duplicate.

If the user instructs duplication, the duplication range deciding unit 110 accepts the user operation input and specifies the selected item, and the duplication range is identified by the above-described processing. Operation input to instruct duplication can be performed by key operation.

The items identified as the duplication range are displayed in the editing screen of the current report by the report display control unit 109. The report display control unit 109 further displays an icon for the user to instruct duplication of the items displayed in the editing screen of the current report near a location near the items. Duplication is confirmed by the user performing an operation input as to the icon to instruct duplication.

With respect to a form of displaying the items identified as the duplication range in the editing screen of the current report, the items are displayed in a manner distinguished from the other report items previously created in the current report. For example, by the transparency or color of the input frame of the items identified as the duplication range. The items identified as the duplication range can be displayed at a position coordinated with display of a pointer of a mouse, which is an example of the input device 11. For example, one item of a past report is dragged to the editing screen of the current report. Upon receiving the drag operation input, the duplication range deciding unit 110 identifies the duplication range by the above-described processing.

The report display control unit 109 displays the items dragged to the editing screen of the current report and the items identified by the duplication range deciding unit 110 near the mouse pointer. Dropping these at the editing screen of the current report is deemed to be an instruction confirming duplication, so the report items are duplicated at or near the position where there has been the drop operation input. Display can be performed where these examples have been combined.

Figure 11:
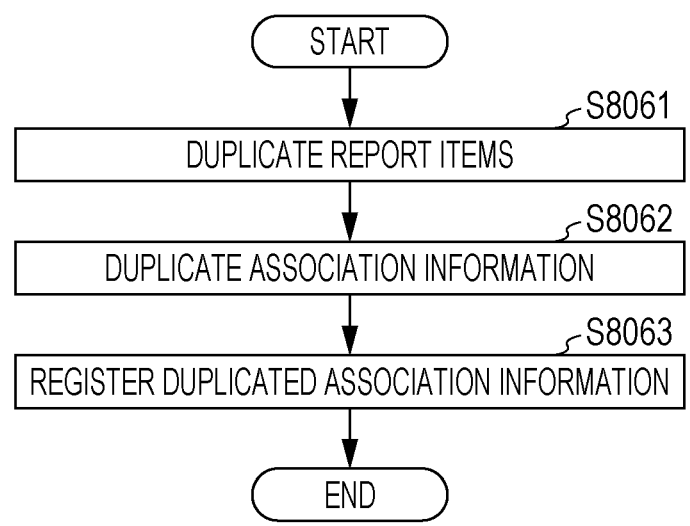
FIG. 11 is a diagram illustrating an example of detailed processing for procedures to duplicate a duplication range that has been decided upon in a report being newly created.

The processing in S806 in FIG. 8 regarding processing of duplicating items identified as the duplication range in the current report will be described in detail with reference to FIG. 11. FIG. 11 is a diagram exemplifying a flowchart of duplication processing. In S8061, the report item creating unit 102 duplicates all report items identified as the duplication range in S805 in the current report. When duplicating, the report item creating unit 102 creates items in the current report to register the contents to be duplicated. The created items are the same as the items identified in S805 with regard to the type and contents of the items, but unique numbers are newly assigned by the item table 701 for the item IDs, and the report ID is an ID corresponding to the current report.

In S8062, the association information creating unit 104 duplicates association information regarding all associations of the items identified in S805, and the association information saving unit 105 saves the duplicated association information in the association table 702. The association IDs of the duplicated association information are newly assigned unique numbers in the association table 702, and the report item ID1 and report item ID2 are duplicated in S8061 and assigned new report item IDs.

In S8063, the duplicate association information creating unit 106 creates, based on the association ID in the original and the corresponding association ID in the duplicate, duplication information for each record in the association table 702 that has been duplicated, which is then saved in the duplicate association table 703 by the duplicate association information saving unit 107. The contents duplicated in this way are displayed in the editing screen of the current report by the association information presenting unit 111, and the contents can be edited by the report item content editing unit 103.

Although the present embodiment has been described with regard to an arrangement where report items in findings, diagnosis, and treatment are created in the radiogram interpretation report, these can be acquired from other systems. For example, items saved in electronic medical records can be acquired and associated. At this time, the symptoms and clinical history of a patient, living environment of the patient, etc., can also be associated as items.

While the requesting contents included in the order information have been described as being applied as request tags in the present embodiment, association can be made by another method. For example, the requesting contents can be created as report items representing findings, diagnosis, treatment, etc., and associated in the same way as with other report items. An arrangement can be made where an ordering system in an HIS is used to associate radiogram interpretation reports with identification information for managing orders, such as associating order numbers with radiogram interpretation reports.

Although a description has been made in the present embodiment restricting the object of duplication to being information within the report creating area 134, other information can be used as the object of duplication. For example, information in the order information display area 133 can be used as report items. An arrangement can be made where drag-and-drop of items within the order information display area 133 to the order information display area (past report) 146 duplicates ordering information items in the past report as ordering information items in the current report.

Second Embodiment

A second embodiment will be described with reference to FIGS. 7 and 34, regarding a method of automatically deciding, based on user input operation, the type of association among report items at the association information creating unit 104.

Figure 7:
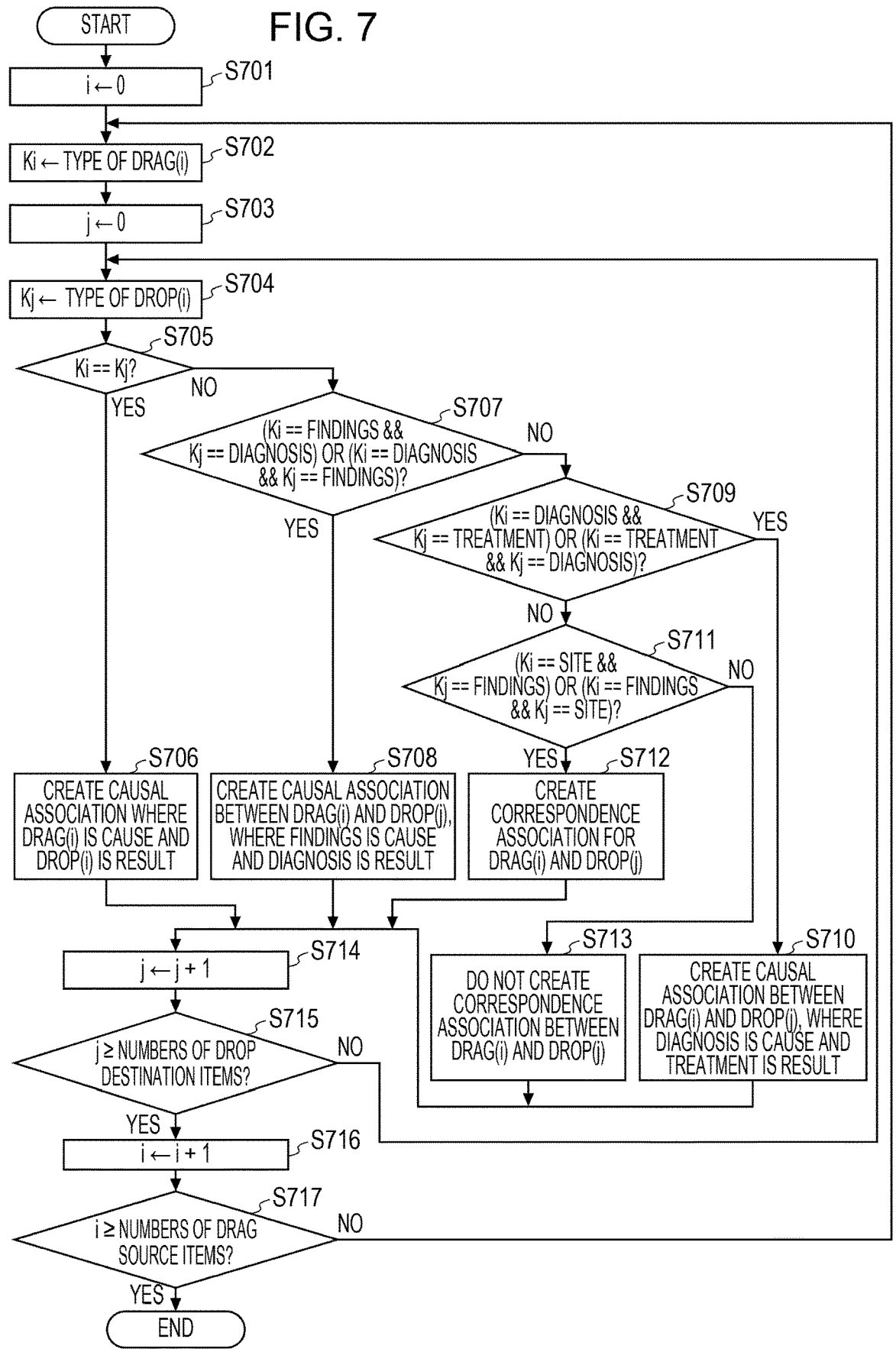
FIG. 7 is a diagram illustrating an example of procedures for processing to automatically determine the type of association between report items.

FIG. 7 is a flowchart illustrating procedures of processing for automatically deciding the type of association among report items at the association information creating unit 104. The flowchart in FIG. 7 only deals with automatically deciding correspondence associations and causal associations out of the types of associations. Adversarial associations are manually specified by a user, and time-series associations are specified in the above-described time-series information window. An example will be described here regarding drag-and-drop of an input frame as being an operation input instructing association among report items. Assumption will be made that multiple report items at the drag source and multiple report items at the drop target have been selected.

An n'th report item in a set of report items at the drag source can be referenced by a function DRAG(n). An n'th report item in a set of report items at the drop target can be referenced by a function DROP(n). The n'th in a certain set is the n'th of serial numbers given to multiple report items included in a state so that the report items are distinguishable.

In S701, 0 is substituted in to variable i. In S702, the type of report item obtained by DRAG(i) is substituted into variable Ki. In S703, 0 is substituted into variable j. In S704, the type of report item obtained by DROP(j) is substituted into variable Kj. In S705, the type Ki of DRAG(i) is compared with the type Kj of DROP(j). In a case where the type of the items is the same, the flow advances to S706. If different, the flow advances to S707. In S706, the association between DRAG(i) and DROP(j) is decided that DRAG(i) is the cause, and DROP(j) is the result. In S707, determination is made regarding whether one of the type Ki of DRAG(i) and the type Kj of DROP(j) is findings and the other diagnosis. In a case where one is findings and the other diagnosis, the flow advances to S708. Otherwise, the flow advances to S709.

The association of DRAG(i) and DROP(j) is decided in S708. The association is a causal association, in which the one of DRAG(i) and DROP(j) of which the type of item is findings is the cause, and the one of which the type of the item is diagnosis is the result. In S709, determination is made regarding whether one of the type Ki of DRAG(i) and the type Kj of DROP(j) is diagnosis and the other treatment. In a case where one is diagnosis and the other treatment, the flow advances to S710. Otherwise, the flow advances to S711.

The association of DRAG(i) and DROP(j) is decided in S710. The association is a causal association, in which the one of DRAG(i) and DROP(j) of which the type of item is diagnosis is the cause, and the one of which the type of the item is treatment is the result. In S711, determination is made regarding whether one of the type Ki of DRAG(i) and the type Kj of DROP(j) is site and the other findings. In a case where one is site and the other findings, the flow advances to S712. Otherwise, the flow advances to S713.

The association of DRAG(i) and DROP(j) is decided in S712 to be a correspondence association. In S713, judgment is made that there is no direct association between DRAG(i) and DROP(j), and no association information is created. In S714, variable j is incremented by 1. In S715, the variable j is compared with the number of report items at the drop target. In a case where the variable j is greater than or equal to the number of report items at the drop target, the flow advances to S716. Otherwise, the flow returns to S704.

The variable i is incremented by 1 in S716. In S717, the variable i is compared with the number of report items at the drag source. In a case where the variable i is greater than or equal to the number of report items at the drag source, the processing ends. Otherwise, the flow returns to S702.

According to the above-described example, association information indicating an adversarial association can be newly created by user operation input. Also, association information indicating correspondence associations or causal associations automatically created by the flow exemplified in FIG. 7 can also be corrected into association information indicating adversarial associations by user operation input. In another example, creation of adversarial associations can also be automated. For example, in a case where the types of both Ki and Kj are diagnosis in S706, the contents described in the report items obtained by DRAG(i) and DROP(j) are analyzed using known morphological analysis, medical dictionaries, etc. Whether there is an adversarial association is determined based on having compared the results of the analysis with an association prediction table 3401, as exemplified in FIG. 34, that has been provided beforehand.

In a case of determining an adversarial association, association information indicating an adversarial association is created between DRAG(i) and DROP(j). The details of processing of deciding whether there is an adversarial association among report items using the association prediction table illustrated in FIG. 34 will be described in the third embodiment. Thus, the type of associations among report items can be automatically selected by the medical report creating apparatus according to the second embodiment. This reduces operation steps of the radiogram interpretation physician creating a structured report.

Third Embodiment

A third embodiment will be described regarding a method of suggesting input of necessary report items to a user with reference to FIGS. 34, 35, and 42A through 44B.

In the medical report creating apparatus 1 according to the third embodiment, the association information creating unit 104 predicts association between a report item created or selected by a user and another report item already input when the user has created or selected a report item. In a case where the results of the prediction show that there are diagnoses in an adversarial association, the report item creating unit 102 creates a report item for inputting a recommendation, thereby prompting the user to input a recommendation.

An adversarial association is multiple hypotheses of contradicting findings or diagnoses. If there are contradicting hypotheses, these hypotheses are tentatively listed as candidates, and that to be finalized as a diagnosis is decided in later verification work. Accordingly, there are cases where treatment is described in a radiogram interpretation report to finalize the diagnosed name of the disease. In a case where multiple hypotheses each present different diagnosis names in the present embodiment, an item for recommended treatment to finalize the diagnosed name of the disease is displayed in the current report. Assumption will be made that the association prediction table 3401 exemplarily illustrated in FIG. 34 has been prepared beforehand in the medical report creating apparatus according to the third embodiment.

The association prediction table 3401 has saved therein two combinations of two types of words (hereinafter referred to as "word set"), types of associations between the words, and the probability of association in a correlated manner. In a case where the type of association is a causal association, a word set 1 has been saved as the cause and a word set 2 as the result. The contents of the association prediction table 3401 can be updated based on the contents of the item table 701 and association table 702 of the past report.

Figure 35B:
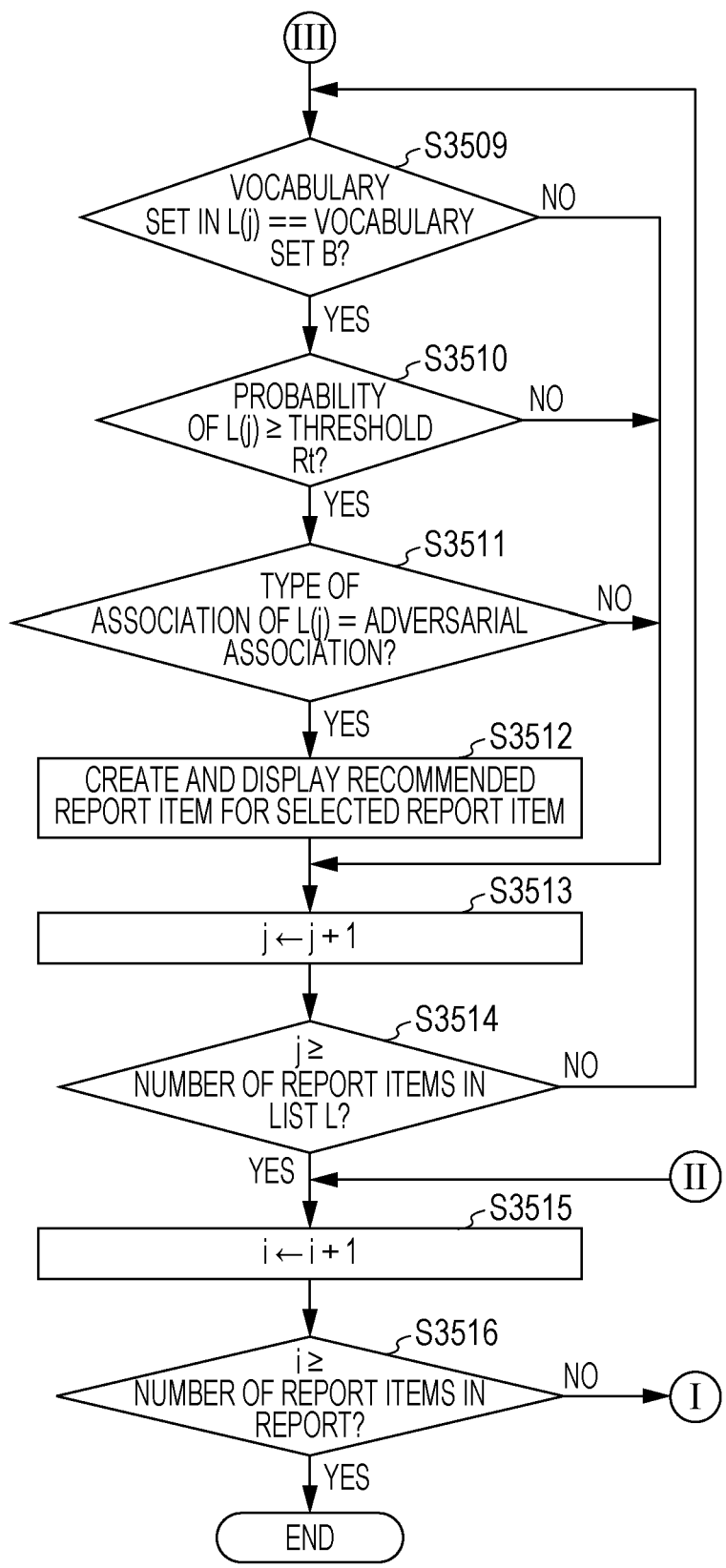

FIGS. 35A and 35B are a flowchart exemplarily illustrating procedures for processing when a user has created or selected a report item. The described content of the n'th report item in the item table 701 can be obtained by function Obj(n). In S3501, in a case where the content of the report item specified by the user performing operation input to select the report item is a sentence, the association information creating unit 104 analyzes the content thereof to extract words contained in the sentence, such as names of diagnosis, etc. The sentence is analyzed using known morphological analysis, medical dictionaries, etc. The combination of multiple words extracted here are handled as word set A.

In S3502, the association prediction table 3401 is referenced and a word set, type of association, and probability that corresponds to the word set A are extracted. There is a possibility that there are multiple sets of information corresponding to the word set A. The extracted group of information sets is made into a list, and handled as list L. The n'th element in the multiple elements contained in the list L can be accessed as L(n). In S3503, 0 is substituted into the variable i. In the following, all report items described in the item table 701 are referenced by the variable i, and items satisfying the following conditions are extracted.

In the processing of S3504 through S3506, report items of diagnoses other than the report item selected by the user in the report containing the selected report items are extracted. In S3504, determination is made regarding whether Obj(i) differs from the selected report item. If Obj(i) differs from the selected report item, the flow advances to S3505. Otherwise, the flow advances to S3515.

In S3505, determination is made regarding whether the report ID corresponding to Obj(i) differs from the report ID corresponding to the selected report item. The ID corresponding to each report item is identified from the report ID column in the item table 701. If the report ID corresponding to Obj(i) differs from the report ID corresponding to the selected report item, the flow advances to S3506. Otherwise, the flow advances to S3515.

In S3506, determination is made regarding whether Obj(i) is diagnosis. If Obj(i) is diagnosis, the flow advances to S3507. Otherwise, the flow advances to S3515. In a case where the content of Obj(i) is a sentence, in S3507, the content thereof is analyzed to extract words contained in the sentence, such as names of findings and names of diagnosis, etc. The combination of extracted multiple words are handled as word set B. In S3508, 0 is substituted into variable j. In the following, all report items described in the list L are referenced by the variable j, and determination is made regarding whether the following conditions are satisfied.

In the processing of S3509 through S3011, determination is made regarding whether there is that in the list L that is included in the word set B, and also is predicted to be in an adversarial association in light of a probability that the user permits. In S3509, determination is made regarding whether a word set in an element of L(j) and the word set B are the same. In a case where the word set in L(j) and the word set B are the same, the flow advances to S3510. Otherwise, the flow advances to S3513.

In S3510, the value of the probability of L(j) is compared with a threshold Rt. The value of the threshold Rt has been set beforehand. In a case where the probability of L(j) is not less than the threshold Rt, the flow advances to S3511. Otherwise, the flow advances to S3513.

In S3511, whether the association type of L(j) is adversarial association is checked. If the association type of L(j) is adversarial association, the flow advances to S3512. Otherwise, the flow advances to S3513. In S3512, an input frame for the recommended report item relating to the selected report item is automatically generated, and displayed highlighted so that the correlation with the report item for Obj(i) can be comprehended. The way in which this display is made can be changed depending on the probability value in the association prediction table 3401.

In addition, in S3512, the association information creating unit 104, association information saving unit 105, and association information presenting unit 111 can automatically create association information that the selected report item and Obj(i) are in an adversarial association, save this in the association table 702, and display the association information on the screen. In another example of S3512, a screen for the user to specify whether to create a recommended report item relating to the selected report item is displayed on a display unit. In a case where the user specifies creating a recommended report item by operation input, the recommended report item is created in the current report.

In S3513, variable j is incremented by 1. In S3514, the number of elements of j and list L is compared. If the variable j is greater than or equal to the number of elements in the list L, all words contained in the list L have been referenced, so the flow advances to S3515. Otherwise, the flow returns to S3509.

In S3515, variable i is incremented by 1. In S3516, variable i is compared with the number of report items contained in the item table 701. If variable i is greater than or equal to the number of report items, the processing ends. Otherwise, the flow returns to S3504.

FIGS. 42A through 44B are diagrams illustrating an example of display on the display unit for the processing illustrated in FIGS. 35A and 35B. In FIGS. 42A and 42B, images 4201, 4202, 4203, and 4204 are displayed as site items. A findings item 4205 is associated with image 4201 and image 4202. A findings item 4206 is associated with image 4203 and image 4204. A diagnosis item 4207 is associated with the findings item 4205. A diagnosis item 4208 is associated with the findings item 4206.

FIG. 42B is an example of display on the display unit in a case where a treatment item 4209 is created by the processing illustrated in FIGS. 35A and 35B. Diagnosis 4207 and diagnosis 4208 are in an exclusive association. A treatment item 4209 is created by the report item creating unit 102, and the report display control unit 109 displays a highlighted frame 4210 to display the item 4209 so as to be distinguishable from other items.

Figures 43A, 43B:
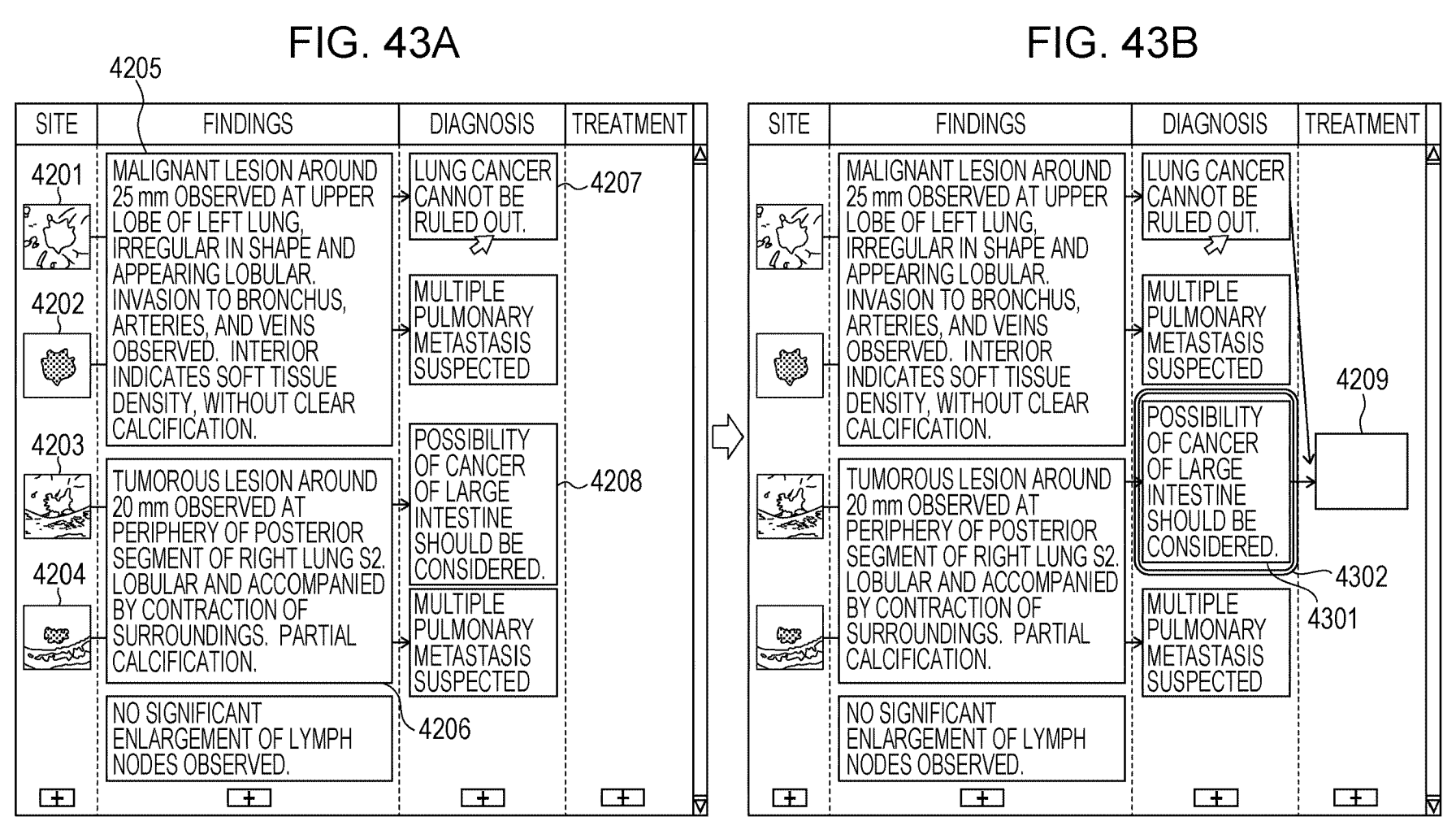

FIGS. 43A and 43B illustrate another example of display on the display unit in the processing illustrated in FIGS. 35A and 35B. In a case where one item in the adversarial association is selected by the input device 11, as in FIGS. 35A and 35B, the other item in the adversarial association can be displayed so as to be distinguishable from other items. A description will be provided with regard to a case where a user clicks on the diagnosis item 4207 using a mouse that is an example of the input device 11, or a case where a mouse pointer indicating the operating position of the mouse is displayed on the item 4207. The report display control unit 109 displays the diagnosis item 4208, which contains a description that is in an adversarial association with the diagnosis item 4207, with a highlight frame 4302 so as to be distinguishable from other items.

FIGS. 44A and 44B illustrate yet another example of display on the display unit in the processing illustrated in FIGS. 35A and 35B. The report display control unit 109 displays an arrow 4402 indicating the adversarial association between diagnosis item 4401 and item 4301 that are in the adversarial association. Accordingly, a user can readily comprehend items that are in an adversarial association. The methods exemplified in FIGS. 42A through 44B can be executed at the same time.

The duplication range deciding unit 110 functions as an identifying unit that identifies, out of multiple items in the radiogram interpretation report, at least two items included in diagnosis information regarding an object of diagnosis that are in an exclusive association. The report display control unit 109 functions as a treatment display unit that displays items that are associated with the items identified by the identifying unit and that are included in information indicating treatment in a screen for creating a radiogram interpretation report. From another perspective, the report display control unit 109 functions as a treatment display unit that displays a screen to prompt a user to specify whether to create an input frame for items that are associated with the items identified by the identifying unit and that are included in information indicating treatment.

Thus, in the medical report creating apparatus 1 according to the third embodiment, in a case where there is a diagnosis report item in an adversarial association with a selected diagnosis report item, an input frame for a recommended report item is automatically created and presented to s user. This can prevent overlooking filling in the recommendation. That is, in a case where there are multiple items for diagnosis regarding which verification will be conceivably necessary later on, the treatment items are displayed in the radiogram interpretation report creating screen, thereby providing support such that the radiogram interpretation physician creating the radiogram interpretation report can describe recommended treatment, and the ordering physician viewing the radiogram interpretation report can confirm the treatment.

Although aspects of predicting association described above have focused on diagnosis report items in FIGS. 35A and 35B, the same processing can be performed including findings report items relating to diagnosis. Accordingly, the association between items can be accurately predicted. Also, performing the same processing on all report items enables associations to be predicted among items and presented to a user.

Although aspects of association prediction described above have focused on report items within the report describing selected diagnosis report items in the description in FIGS. 35A and 35B, this can be expanded to report items belonging to other reports described in the past. For example, aspects of prediction of associations can be expanded to report items in past reports regarding the patient, regarding which the report including the selected diagnosis report item has been described. In this case, association between diagnoses described in the past and the content of the diagnosis currently described can be automatically detected, thereby proactively preventing erroneous description by the radiogram interpretation physician.

Although the type of association between diagnoses has been described as being predicted using the association prediction table 3401 with reference to FIGS. 35A and 35B, another method can be used. For example, the association between diagnoses may be predicted from the content of the findings and the way that the findings and the diagnosis are connected. For example, if a lesion is a node or tumor mass, there is a high probability of having a single diagnosis name. In a case where there are multiple diagnosis report items associated with a findings report item describing a node or tumor mass, the diagnoses can be judged to be in an adversarial association.

On the other hand, in a case where the findings are focal abnormalities, diffuse abnormalities, or generalized abnormalities, there is a possibility that there may be multiple diagnosis names, so multiple diagnosis report items can exist. In this case, the type of association between diagnoses is predicted using the method described in FIGS. 35A and 35B.

The above-described arrangement can be used to restrict association from findings to diagnosis. For example, if the findings describe a node or tumor mass, the associated diagnosis can be set to one.

Fourth Embodiment

In a fourth embodiment, when duplicating and using content described in a past report, the duplicated content and display format can be made to be in a state suitable for the duplicate, at the point that the series of processing relating to duplication has ended. For example, at the time of duplicating images including images from a past report in the current report, the images are substituted with images corresponding to the requesting content of the current report and displayed, instead of the images acquired when the past report was created. In another example, at the time of duplicating items including the size of a lesion from the past report, items including description of the size of the lesion are displayed enhanced, since there is a good chance that the size of the lesion will have changed at the point of creating the current report.

The medical report creating apparatus 1 according to the present embodiment supports efficiently confirming and correcting in the current report the described contents duplicated from the past report. Subject to confirmation and correction are, for example, examination images, measurement values regarding lesions, diagnosis names, volume of body organs, etc. Although several aspects will be described in detail, the following aspects of confirmation and correction are only examples, and the aspects of confirmation and correction are not limited to the following. A description will be provided with reference to FIGS. 12, 13, 40, 41A, and 41B.

An example will be described regarding a case where an item identified by the duplication range deciding unit 110 as being in the duplication range contains an image. The soft copy of the medical image displayed in the past report was acquired at the time that the past report was created, and the possibility that it is different from the image that should be displayed in the current report being edited is high. Accordingly, even if an image is included in an item identified as being in the duplication range, that image is not duplicated in the current report. A medical image corresponding to the medical image attached to the past report is attached to the current report, and the soft copy thereof is what is displayed.

The report item creating unit 102 acquires information of examinations, where the image in the past report identified as being in the duplication range was acquired. This is information regarding the acquired region the patient that is the subject of diagnosis, and the apparatus used for taking the image. The report item creating unit 102 acquires a corresponding medical image from the medical image database 8 based on this examination information. That is, the report item creating unit 102 functions as an image acquisition unit.

In a case where the image attached to the past report (hereinafter referred to as "past image") is a cross-sectional image of a three-dimensional image, attribute information such as the slice position, etc., can be acquired. In a case of duplicating an item including an image in the processing of S8061 in FIG. 11, an image of a imaging region corresponding to this image, that corresponds to the current report, is acquired. That is, an image that is of the same imaging region and acquired by the same imaging apparatus as the past image, and that is the object of observation in creation of the current report, is acquired. Duplication processing is then performed using a soft copy of the acquired image as a report item. Processing of substituting images will be described with reference to FIGS. 12 and 13.

Figure 12:
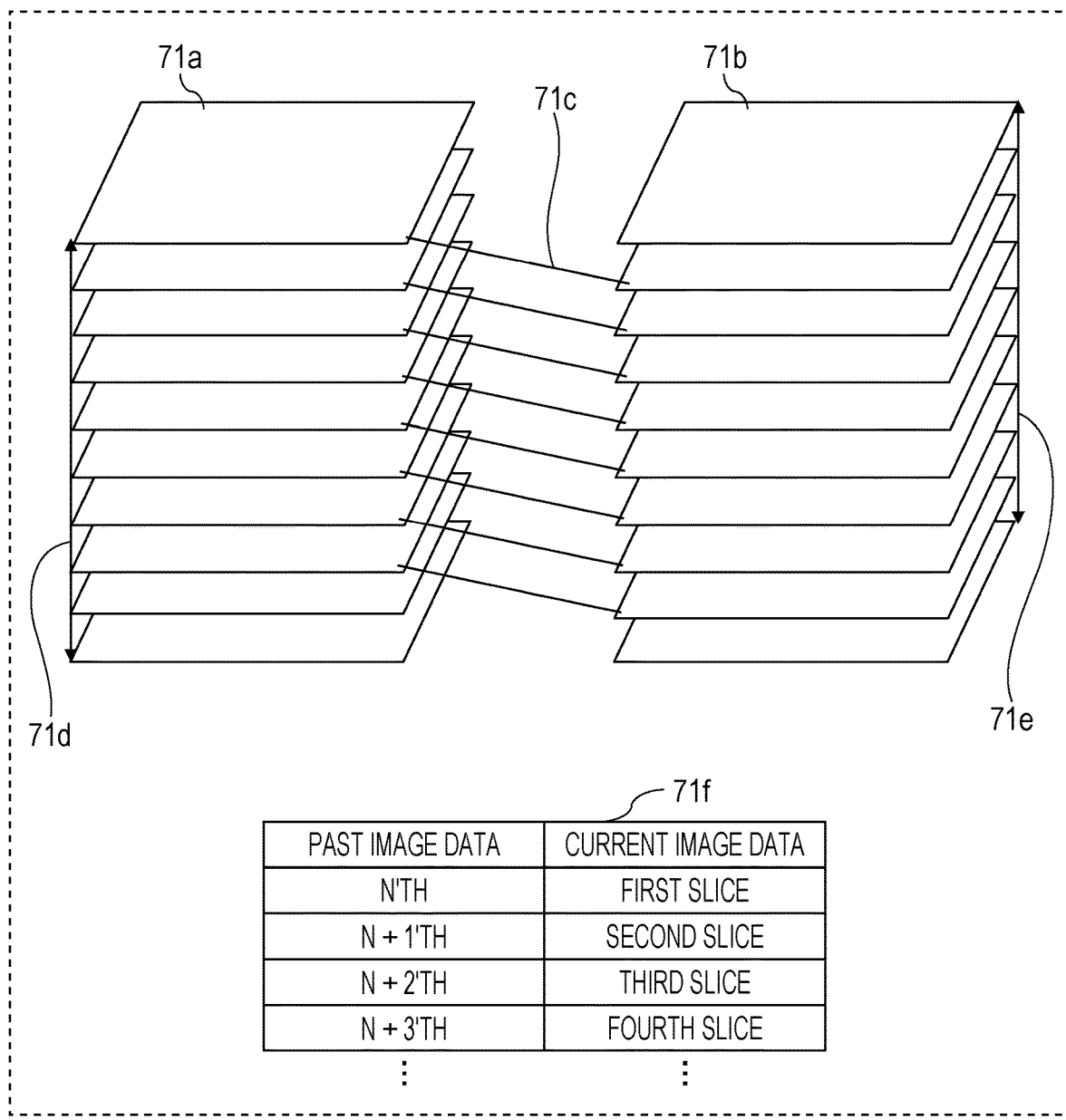
FIG. 12 is a diagram illustrating an example of a correspondence association between previously acquired images and currently acquired images.

In FIG. 12, reference symbol 71d denotes a group of slice data of medical images acquired with a single modality in a past examination. Reference symbol 71a denotes one slice image out of 71d. Reference symbol 71e denotes a group of slice data of medical images acquired with a single modality in the current examination. Reference symbol 71b denotes one slice image out of 71e. 71e and 71a are image groups of the same imaging region, and have been acquired by the same modality. Reference symbol 71c denotes conceptual lines of correspondence between the individual slice images 71a making up 71d and the individual slice images 71b making up 71e, the correspondence association thereof being as illustrated in table 71f. Table 71f illustrates that, for example, the current image 71b corresponding to the N+2'th past image 71a belonging to the past image data 71d is the third medical image in the current image data 71e.

Figure 13:
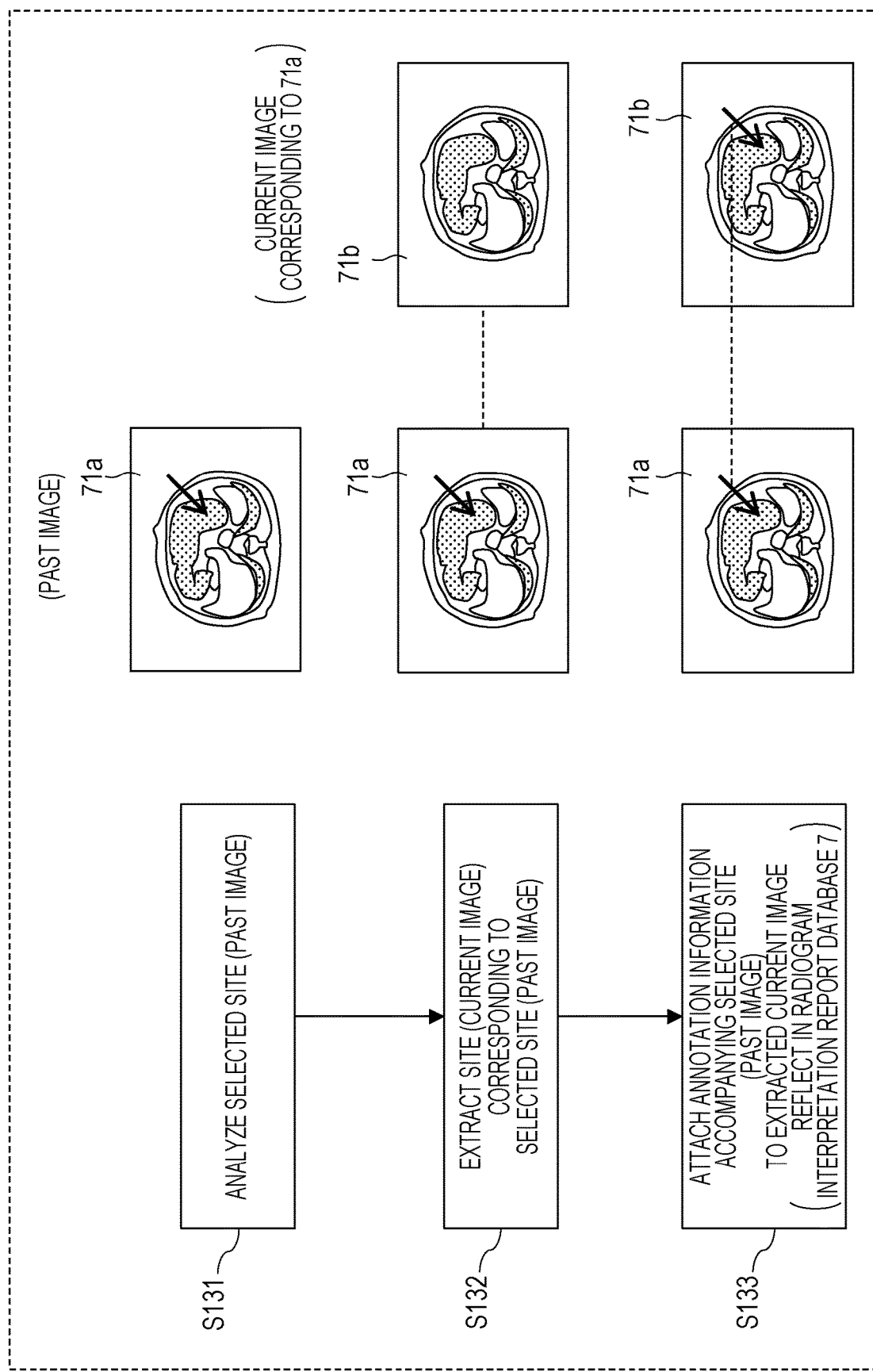
FIG. 13 is a diagram illustrating an example of procedures for processing to convert a past image into a corresponding current image when duplicating.

FIG. 13 is a flowchart illustrating a case where the content of the report item to be duplicated is a soft copy of a past image, and the duplicated content is replaced with a soft copy of a current image. In S131, the report item creating unit 102 acquires, from the medical image database 8 via the PACS 5, information relating to the past image data 71d to which the past image 71a serving as the basis for the past image to be duplicated belongs. For example, information of an examination at the time of having acquired the past image is obtained. The information of this examination includes, for example, the start position of imaging, end position of imaging, slice thickness, site being shot, and modality information. This information enables the imaging position of each slice in the past image to be estimated.

In S132, current image data 71e of the same imaging site by the same modality is identified from images acquired by examination that are newer than the past image, and information of the imaging position of each slice is found from the starting and ending position of imaging and slice thickness. Table 71f is created using this information along with the information acquired in S131, and a current image 71b having the same (or closest) imaging position to the medical image 71a that is the basis for the soft copy of the past image is extracted. The method of extracting the current image 71b is not limited to this approach, and image analysis, etc., can be used.

In S133, annotations attached to the past image and image processing parameters applied to the past image are applied to the current image that has been extracted. That is, in a case where annotation information indicating annotation is attached to the identified past image, annotation information is also attached to the current image and displayed. This reduces the steps of the radiogram interpretation physician creating the radiogram interpretation report having to attach annotations to the report item being displayed in the current report, having to change parameters, etc.

The report item creating unit 102 saves the soft copy of the current image 71b obtained by the processing through S133 in the item table 701 as content of the report item to be duplicated in the current report. In a case where no current image exists corresponding to the past image in S132, just a report item input frame is created, with the radiogram interpretation physician applying a suitable image manually. That is, the report display control unit 109 displays a region for displaying an image corresponding to the image in the past report in the current report creating screen, in a manner correlated with the item identified to be in the duplication range. An arrangement can be made where the report item creating unit 102 creates an item of a site associated with the duplicated item, and the user manually applies an image to the item of this site.

In S8062 in FIG. 11, the association information creating unit 104 duplicates all association information in the duplication range decided in S805, and the association information saving unit 105 saves this in the association table 702. When duplicating, the association IDs are newly allocated numbers so as to be unique in the association table 702. The report item ID1 and report item ID2 are replaced with item IDs newly assigned when duplicating each of the report items.

In S8063, the duplicate association information creating unit 106 creates duplication information based on the original association IDs and the corresponding association IDs of the duplicate, and the duplicate association information saving unit 107 saves these in the duplicate association table 703. The contents duplicated as described above are displayed in the current report by the association information presenting unit 111, and the report item content editing unit 103 can edit the contents.

With the medical report creating apparatus 1 according to the present embodiment, past images and current images can be easily compared. For example, double clicking on a current image with a mouse, which is an example of the input device 11, causes the image viewing unit 101 to display the current image and past image on the medical image viewing screen 131 side by side. That is, the past image identified by the identifying unit and the current image acquired by the image acquisition unit are displayed on the screen.

As another example of processing in a case where an image of a past report has been identified as being in the duplication range, an arrangement can be made where no current image is acquired, and just a report item input frame is created for displaying the image. That is, the radiogram interpretation physician can be prompted to manually attach all images to be displayed in the report. These settings can be changeable as appropriate by a user.

Next, a description will be provided regarding processing for duplicating in a case where information including attributes where change can occur are described in items for duplication at the time of duplicating from a past report into a current report.

Figure 40:
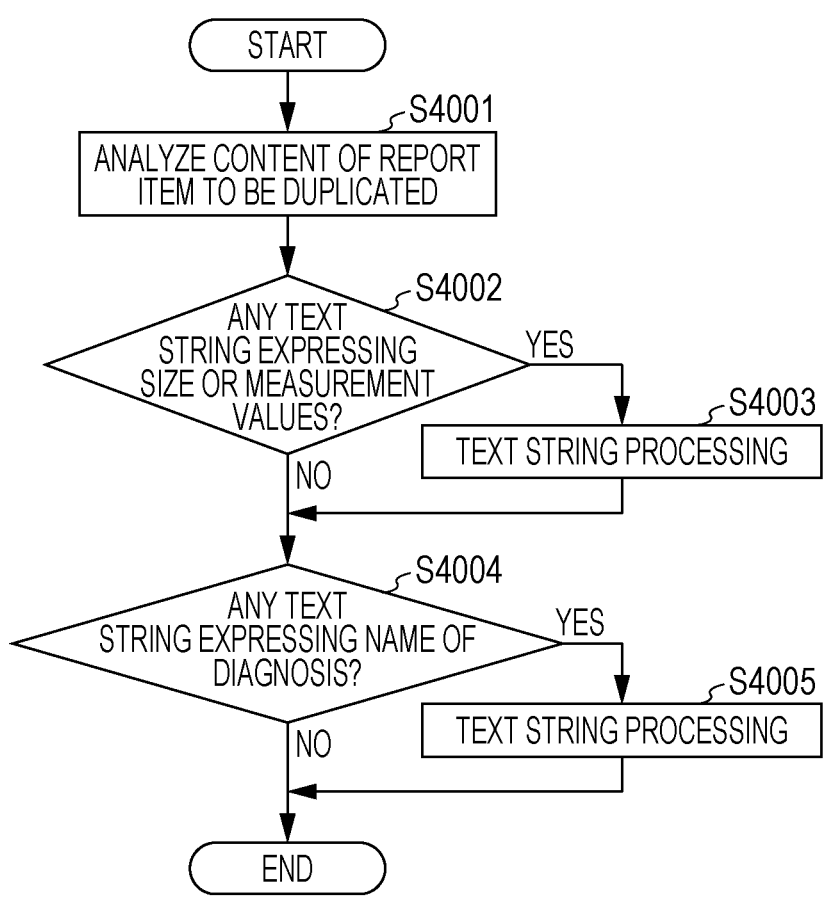
FIG. 40 is a flowchart illustrating an example of processing according to a fourth embodiment.

FIG. 40 is a flowchart illustrating an example of processing for identifying a description in which change can occur, and displaying an input frame for the user to perform input, at the time of duplicating from a past report into a current report. In step S4001, the report item content editing unit 103 analyzes the content of the report items to be duplicated that have been identified by the duplication range deciding unit 110. For example, there are cases that text strings expressing the size or measurement values of a lesion, which are objective facts about the lesion, are included in report items containing information of findings. Also, there are cases that text strings expressing the name of the diagnosis are included in report items containing information of diagnosis.

In step S4002, the report item content editing unit 103 determines, based on the results of the analysis performed in S4001, whether there is a text string including sizes or measurement values relating to the lesion. If sizes or measurement values are determined to be included, the flow advances to step S4003. If sizes or measurement values are determined not to be included, the flow advances to step S4004.

In step S4003, if there is a text string included in the report item to be duplicated expressing lesion size, measurement values, or diagnosis name, the report item content editing unit 103 preforms text string processing so that the text string is not duplicated in the current report. In step S4003, the report item content editing unit 103 performs text string processing to provide input frames for input for text strings suitable for the content of the current report, at positions of the sizes and measurement values of the lesion in the report item of the past report identified to be in the duplication range. The report item creating unit 102 creates the report item in the current repot. The report display control unit 109 displays the item subjected to text string processing by the report item content editing unit 103 on the display unit.

In step S4004, the report item content editing unit 103 determines, based on the results of the analysis performed in S4001 whether there is a text string expressing a diagnosis name. If a text string including a diagnosis name is determined to be included, the flow advances to step S4005. If a text string including a diagnosis name is not included, the flow illustrated in FIG. 40 ends.

In step S4005, the report item content editing unit 103 performs text string processing to provide an input frame for input for text string suitable for the content of the current report at the position of the name of the diagnosis in the report item of the past report identified to be in the duplication range. The report item creating unit 102 creates the report item in the current report. The report display control unit 109 displays the item subjected to text string processing by the report item content editing unit 103 on the display unit.

In S8061 in FIG. 11, medical dictionaries and language processing, etc., are used to automatically extract text strings representing sizes and measurement values of the lesion, and the name of the diagnosis, from the free language to be duplicated, replaces theses with blank input spaces, and thereupon performs duplication processing. A user can set sizes and measurement values of lesions, and names of diagnoses, which are attributes of which change can occur, as predetermined attributes. The sizes and measurement values of the lesion, and the name of the diagnosis, that were true at the time of creating the past report, may not be the same as the point of creating the current report. Accordingly, the user can be supported so as to not overlook text strings that can change. The processing of the determination in step S4002 and the determination in step S4004 can be performed at the same time, and in this case, the text string processing of steps S4004 and S4005 can be performed at the same time. Further, processing of steps S4004 and S4005 can be performed before the processing of steps S4002 and S4003 can be performed.

Figure 41A:
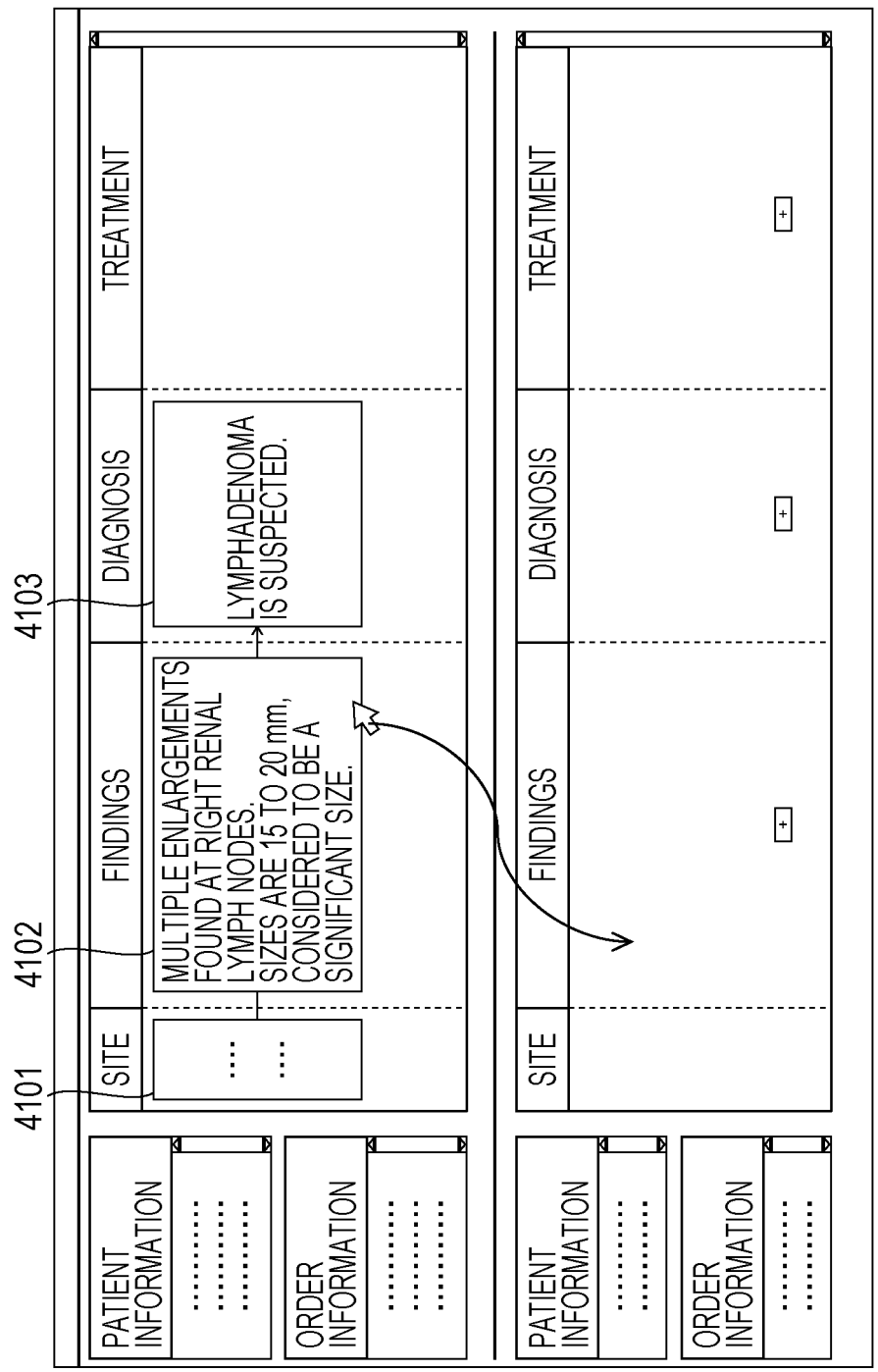

FIGS. 41A and 41B illustrate an example of display on the display unit in the processing of FIG. 40. An example will be described where the duplication range deciding unit 110 has identified a site item 4101, a findings item 4102, and a diagnosis item 4103. The findings item 4102 includes a description regarding size, which is "SIZES ARE 15 TO 20 mm". As a result of the processing in FIG. 40, the findings item 4105 duplicated in the current report has a text string 4107 subjected to text processing so as to read "SIZES ARE  TO  mm" (the asterisks "*" representing blank spaces for input). The item 4103 also includes the diagnosis name "LYMPHADENOMA". As a result of the processing in FIG. 40, the diagnosis item 4106 duplicated in the current report has a text string 4108 subjected to text processing so as to read "*****".

After duplicating, a user manually inputs a text string suitable for the current report in the blank input spaces. Information including attributes such as the size of the lesion can be measurement values measured based on images to be diagnosed. For example, in a case where a node is found in a chest X-ray image or CT image, diagnosis can be performed in accordance in the way in which the size has changed in comparison with past images. That is, information including attributes such as the size of a lesion in a past report can have the description changed in the current report.

In another example, information including attributes such as progress or the degree of progression of the lesion may have changed from the point of having created the past report. Examples of information including such attributes include, but are not limited to, expressions such as "progression" and "cured", and stage classification. In still yet another example, information including attributes such as volume of body organs may also have changed from the point of having created the past report. An example of information including such attributes is lung capacity. Change in lung capacity can be watched as a sign of a certain disease, such as diffuse lung disorder. In a case of observing change over a course of time, there is a possibility that the description of information including attributes such as body organ volume can change. Even if the change is not being watched, it can be suggested to the user as a sign. The user can set information that tends to be overlooked so as to be displayed in this way.

The user can set beforehand what sort of text string should not be duplicated in items duplicated in the current report in the present embodiment. For example, information relating to the size of lesions, information relating to the progression of lesions and information relating to the volume of body organs are set as predetermined attributes. The report display control unit 109 displays items including information including the predetermined attributes in a manner distinguished from other items. Examples of forms of displaying in a manner distinguished from other items include, besides the above-described replacing of the text string with blank spaces, changing the color or font of information including the predetermined attributes from other description, highlighting with a marker, etc. Alternatively, a screen can be displayed for the user to select whether to input change to the description of the information including the predetermined attributes or to use the description in the old report without change.

In another example, a description of information including predetermined attributes can be automatically replaced with a text string suitable for the current report by the system. Further, the report display control unit 109 displays items including predetermined attributes in a manner distinguished from the other items at the time of duplicating the current report, regardless of whether the information including the predetermined attributes is to be replaced with blank spaces or other text strings. The user can confirm the items displayed in a manner distinguished from the other items, and change the description of items including predetermined attributes as necessary.

The report display control unit 109 also displays, on the editing screen of the report, an icon for inputting an instruction to complete creating of the report. In a case where there is an operation input to complete creating the current report being edited, the report display control unit 109 displays a dialogue box indicating a warning. Thus, a user can easily confirm descriptions where changes can occur, thereby reducing overlooking making changes.

A description has been provided in the above example regarding processing to prevent duplication of just a range within a description in an item identified as being within the duplication range. However, the present embodiment is not limited to the above description, and an arrangement can be made where none of the report items identified as being in the duplication range are duplicated, and only the logical structure of the report items is duplicated. That is, new blank input frames and association information are duplicated in the current report.

In S8061 in FIG. 11, the report item creating unit 102 duplicates, in the current report, just the input frames of the report items identified as being in the duplication range in S805. When duplicating, just the types of the items are set to be the same as the duplication range identified in S805, the item IDs are assigned new numbers so as to be unique in the item table 701, and an ID corresponding to the current report is used for the report ID. Regardless of the contents of the original items, nothing is described in the contents of the items here.

In S8062, the association information creating unit 104 duplicates all association information to be duplicated that has been decided in S805, which the association information saving unit 105 then saves in the association table 702. When duplicating, association IDs are assigned new numbers so as to be unique in the association table 702, and the report item ID1 and report item ID2 are replaced with item IDs newly assigned at the time of having being duplicated. Although description has been made above where all contents in the report items to be duplicated are replaced with blanks and then duplication processing is performed, an arrangement can be made where part of the report items to be duplicated are replaced with blanks and then duplication processing is performed. The contents of items including particular information can be replaced with blanks and then duplicated, by performing settings beforehand.

Fifth Embodiment

An example of identifying a duplication range by processing different from the first embodiment through fourth embodiment will be described in a fifth embodiment. The specific processing in S805 in FIG. 8 is what differs from the above-described embodiments. A description will be provided with reference to FIGS. 9 through 10B, 14, 15, and 39.

Figure 9:
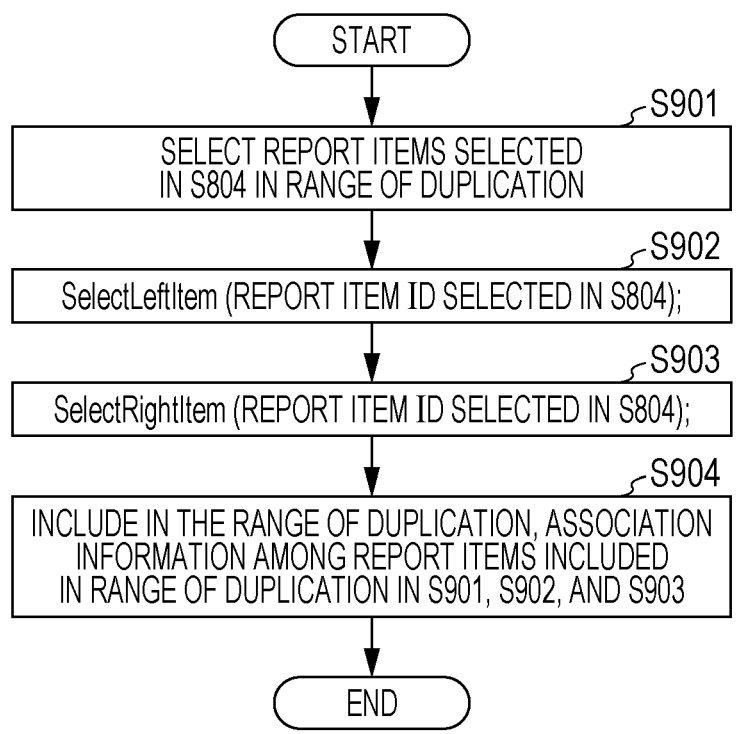
FIG. 9 is a diagram illustrating an example of procedures for processing at a duplication range deciding unit.

FIG. 9 shows a flowchart of duplication range deciding processing according to the present embodiment. This processing identifies items including association information with an item first specified, i.e., identifies items directly associated with specified items. Further, items that are associated with each of the items directly associated with specified items are also identified. However, items in a logical relationship with an item directly associated with a specified item but not associated with the specified item are not identified. An example of items identified by the duplication range deciding processing according to the present embodiment will be described with reference to FIG. 39.

Figure 39:
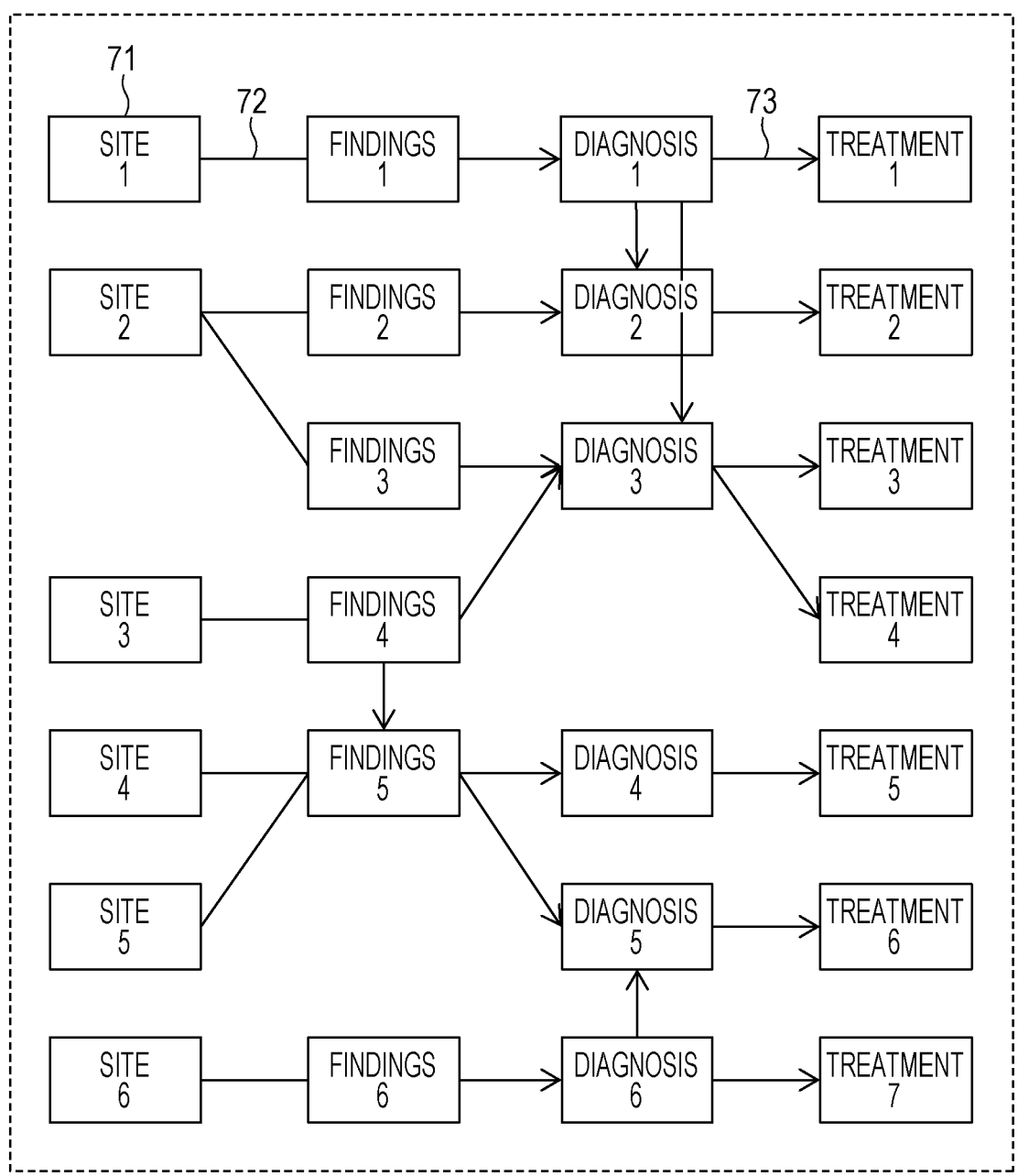
FIG. 39 is a diagram illustrating an example of processing relating to duplication according to a fifth embodiment.

In S804 in FIG. 8, in a case where the site 4 illustrated in FIG. 39 is selected, the site 4, findings 5, diagnosis 4, treatment 5, diagnosis 5, treatment 6, and the five sets of association information among these report items, are identified as the duplication range. The items site 3 and findings 4 that are indirectly associated with the site 4 that is the specified item are unrelated with the site 4 in the logical association of findings being derived from the information of the site, a diagnosis being derived from information of the findings, and a treatment being derived from the diagnosis.

Accordingly, all or part of items directly or indirectly associated with the specified item are identified in the duplication range deciding processing according to the present embodiment.

Figure 10A:
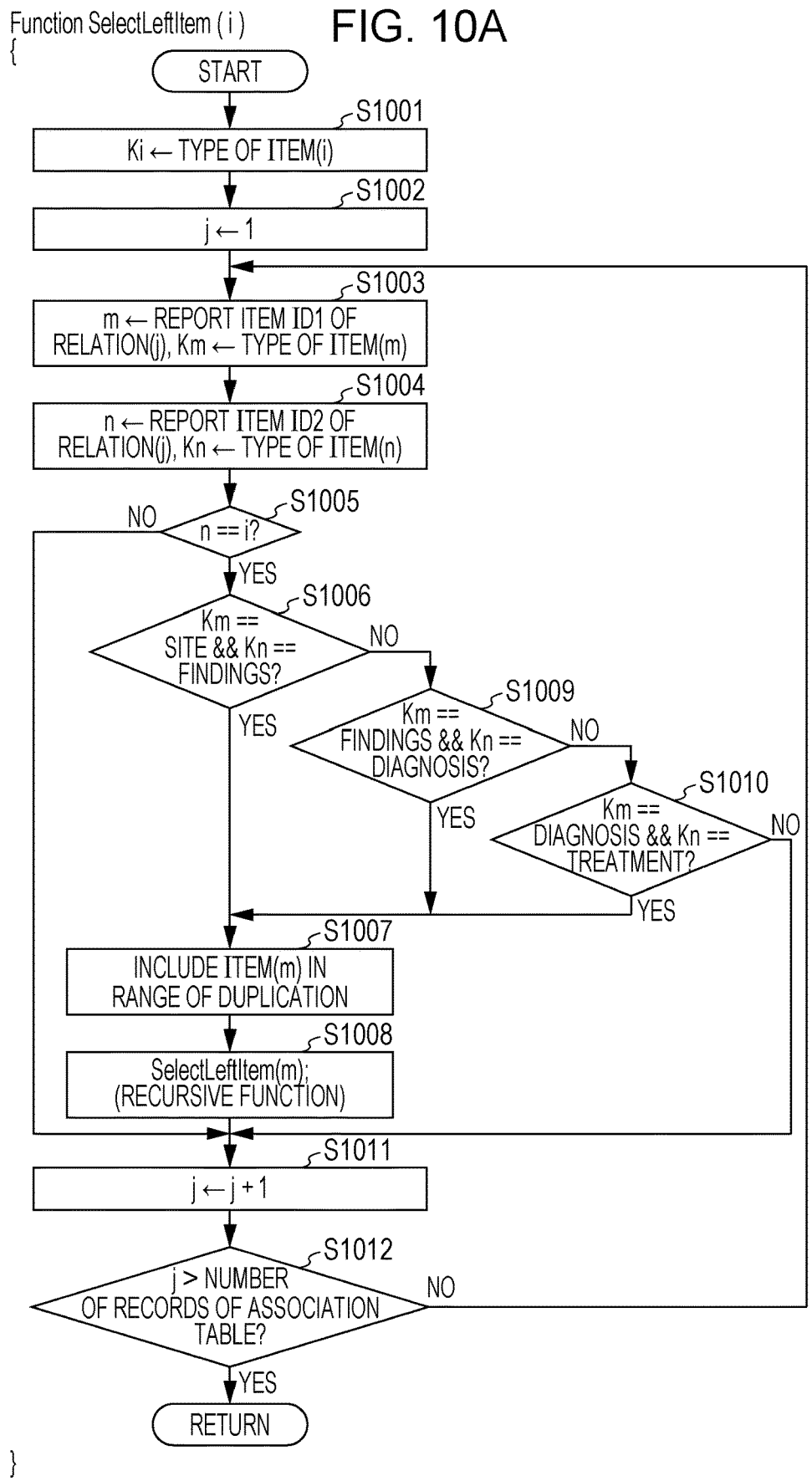
FIGS. 10A and 10B are diagrams illustrating an example of procedures for processing to expand the range of items in a past report to be duplicated.

In S901, the report items selected in S804 are identified as the duplication range. In S902, a function SelectLeftItem illustrated in FIG. 10A is executed using the report ID of a report item included in the duplication range in S901 as an argument. The function SelectLeftItem identifies the argument associated with the item serving as the argument at the upstream side in the logical association described above. The processing of the function SelectLeftItem will be described as exemplified in FIG. 10A. A report item of which the report ID is x can be referenced by function ITEM(x). In a case where the value of x is blank (null), no ITEM(x) exists, in which case the type of ITEM(x) is defined as being "no type". Also, the association information of which the association ID is x can be referenced by a function RELATION(x).

In S1001, the type of ITEM(i) is substituted into the variable Ki. Note that the variable i is an argument of the function SelectLeftItem, and is the value of the report ID. 1 is substituted into the variable j in S1002. In S1003, the report item ID1 of RELATION(j) is substituted into the variable m, and further, the type of ITEM(m) is substituted into the variable Km. In S1004, the report item ID2 of RELATION(j) is substituted into the variable n, and further, the type of ITEM(n) is substituted into the variable Kn. In S1005, the value of variable n and variable i are compared. If these are the same, the flow advances to S1006, and if different, advances to S1011.

In S1006, determination is made regarding whether the type Km of the report item of which the item ID is m is site, and also the type Kn of the report item of which the item ID is n is findings. If the determination value is true, the flow advances to S1007, and if the determination value is false, the flow advances to S1009.

In S1009, determination is made regarding whether the type Km of the report item of which the item ID is m is findings, and also the type Kn of the report item of which the item ID is n is diagnosis. If the determination value is true, the flow advances to S1007, and if the determination value is false, the flow advances to S1010.

In S1010, determination is made regarding whether the type Km of the report item of which the item ID is m is diagnosis, and also the type Kn of the report item of which the item ID is n is treatment. If the determination value is true, the flow advances to S1007, and if the determination value is false, the flow advances to S1011.

In S1007, ITEM(m) is included in the duplication range, and the flow advances to S1008. In S1008, the function SelectLeftItem is executed with m, which is the item ID value, as an argument. That is, the function SelectLeftItem is recursively called up. In S1011, the variable j is incremented. In S1012, determination is made regarding whether the value of variable j is larger than the number of records in the function table. In a case where the determination result in S1012 is false, the flow returns to S1003 and the above processing is repeated. In a case where the determination result in S1012 is true, the function SelectLeftItem ends. That is, the function SelectLeftItem identifies only items that are associated with a particular item and also are upstream in the logical association.

Site items associated with findings items, findings items associated with diagnosis items, and diagnosis items associated with treatment items, are identified. From another perspective, the function SelectLeftItem performs first processing to identify items associated with a particular item in the reverse direction from the forward order of site, findings, diagnosis, and treatment. Items associated with items identified by the first processing, are identified by the first processing.

Figure 10B:
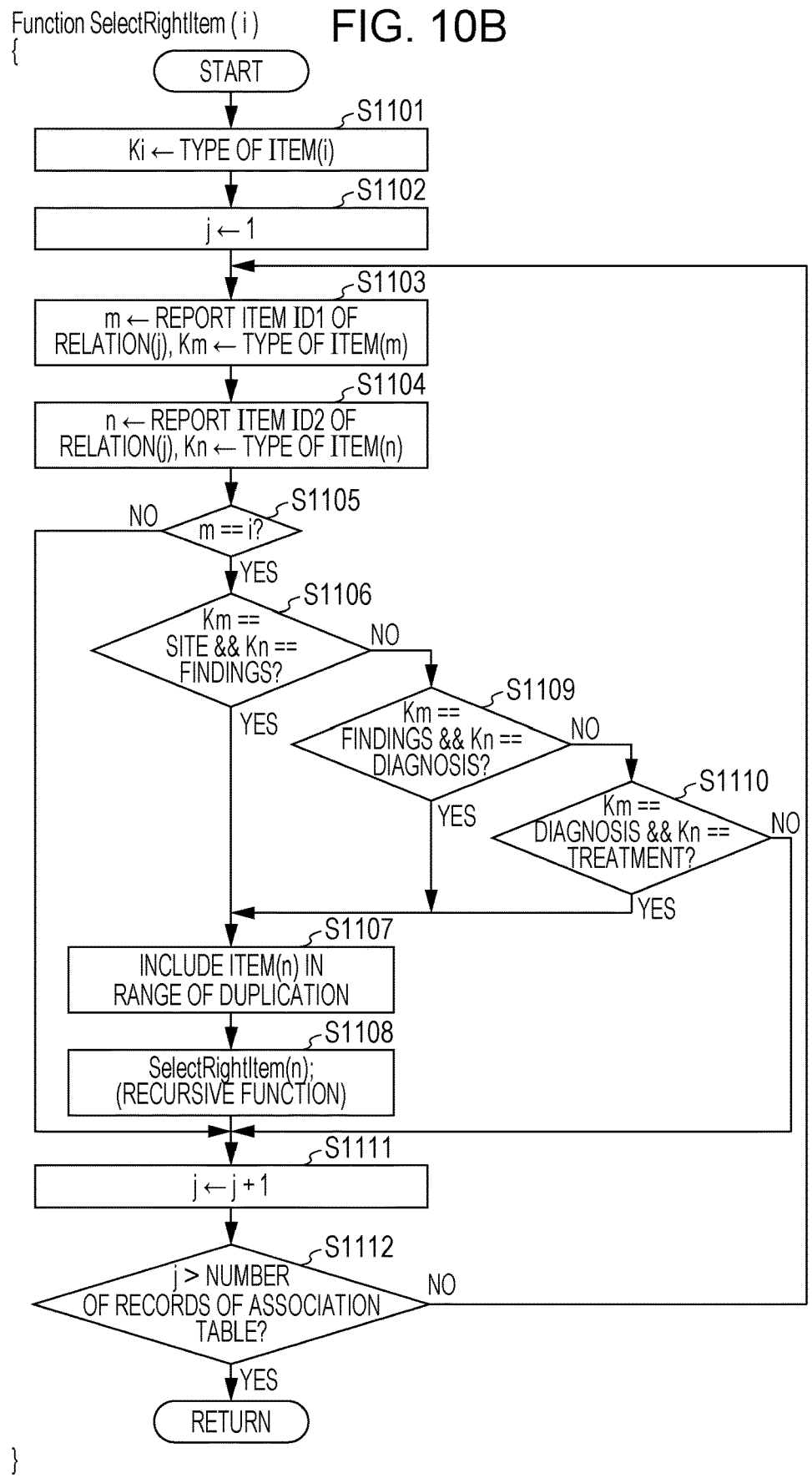

Returning to FIG. 9, in S903, a function SelectRightItem illustrated in FIG. 10B is executed using the report ID of a report item included in the duplication range in S901 as an argument. The function SelectRightItem identifies the argument associated with the item serving as the argument at the downstream side in the logical association described above. The processing of the function SelectRightItem will be described as exemplified in FIG. 10B.

In S1101, the type of ITEM(i) is substituted into the variable Ki. The variable i is an argument of the function SelectRightItem, and is the value of the report ID. 1 is substituted into the variable j in S1102. In S1103, the report item ID1 of RELATION(j) is substituted into the variable m, and further, the type of ITEM(m) is substituted into the variable Km. In S1104, the report item ID2 of RELATION(j) is substituted into the variable n, and further, the type of ITEM(n) is substituted into the variable Kn. In S1105, the value of variable n and variable i are compared. If these are the same, the flow advances to S1106, and if different, advances to S1111.

In S1106, determination is made regarding whether the type Km of the report item of which the item ID is m is site, and also the type Kn of the report item of which the item ID is n is findings. If the determination value is true, the flow advances to S1107, and if the determination value is false, the flow advances to S1109.

In S1109, determination is made regarding whether the type Km of the report item of which the item ID is m is findings, and also the type Kn of the report item of which the item ID is n is diagnosis. If the determination value is true, the flow advances to S1107, and if the determination value is false, the flow advances to S1110.

In S1110, determination is made regarding whether the type Km of the report item of which the item ID is m is diagnosis, and also the type Kn of the report item of which the item ID is n is treatment. If the determination value is true, the flow advances to S1107, and if the determination value is false, the flow advances to S1111.

In S1107, ITEM(n) is included in the duplication range, and the flow advances to S1108. In S1108, the function SelectRightItem is executed with m, which is the item ID value, as an argument. That is, the function SelectRightItem is recursively called up. In S1111, the variable j is incremented. In S1112, determination is made regarding whether the value of variable j is larger than the number of records in the function table. In a case where the determination result in S1112 is false, the flow returns to S1103 and the above processing is repeated. In a case where the determination result in S1112 is true, the function SelectRightItem ends. That is, the function SelectRightItem identifies only items that are associated with a particular item and also are downstream in the logical association.

Treatment items associated with diagnosis items, diagnosis items associated with findings items, and findings items associated with site items, are identified. From another perspective, the function SelectRightItem performs second processing to identify items associated with a particular item in the direction of the forward order of site, findings, diagnosis, and treatment. Items associated with items identified by the second processing, are identified by the second processing.

All association information saved in the association table 702 in FIG. 4B is subject to the processing with the function SelectLeftItem and function SelectRightItem illustrated in FIGS. 10A and 10B. The processing of S1003 through S1008 and S1103 through S1108 are performed on all association information. However, an arrangement can be made in actual implementation where the object of such processing is narrowed down beforehand, from the perspective of processing speed. For example, the association information in the association table 702 is narrowed down to association information belonging to past reports regarding which the report item ID1 and report item ID2 have both been selected in S804. The processing of S1003 through S1008 and S1103 through S1108 can then be performed regarding just the narrowed-down association information. Alternatively, a graph structure can be used such as described in the first embodiment.

Returning to FIG. 9, the association information among report items identified as the duplication range by the processing in S901 through S903 is included in the duplication range in S904. Specifically, association information where report items falling under report item ID1 and report item ID2 that are both included in the duplication range are extracted from all records in the association table 702, and set as the duplication range.

Items identified by the duplication range deciding unit 110 described above will be described with reference to FIG. 39. In S804 in FIG. 8, in a case where the site 4 in FIG. 39 has been selected for example, the duplication range is as the duplication range is the site 4, findings 5, diagnosis 4, treatment 5, diagnosis 5, treatment 6, and the five association information among these report items. In a case where the user has selected the two of diagnosis 5 and findings 6, the site 4, site 5, findings 5, diagnosis 5, and treatment 6 are identified as the duplication range, in accordance with the diagnosis 5 having been specified. In accordance with the findings 6 having been specified, the site 6, findings 6, diagnosis 6, and treatment 7 are identified as the duplication range. Eight association information including the causal association between the diagnosis 5 and diagnosis 6 are also included as association information of these report items.

According to the duplication range deciding processing of the present embodiment, not all report items directly or indirectly associated with the report items selected in S804 are set as the duplication range, unlike the processing of duplication range deciding described in the first embodiment. The duplication range can be decided by restricting to items necessary to understand the report item selected in S804, and report items that need the report item selected in S804 for understanding, and deciding the duplication range through upstream and downstream association. Report items in an adversarial association with report items in the duplication range have been excluded from the duplication range in the duplication range deciding processing exemplified in the present embodiment. An arrangement can be made in actual implementation where report items in adversarial association are included in the duplication range as appropriate, under some sort of judgment standard.

The following is a description of a method to make editing work by the user after having performed duplication processing more efficient in a case of having identified and duplicated a part of items associated with a specified item. Efficiency can be realized by using association information among report items. For example, at the time of displaying the report items duplicated by the association information presenting unit 111 on the screen, the report display control unit 109 provides a display suggesting that there are items associated with the specified item that have not been duplicated. The items associated with identified items but not duplicated can be extracted by referencing the duplicate association table 703 and association table 702.

Figure 14:
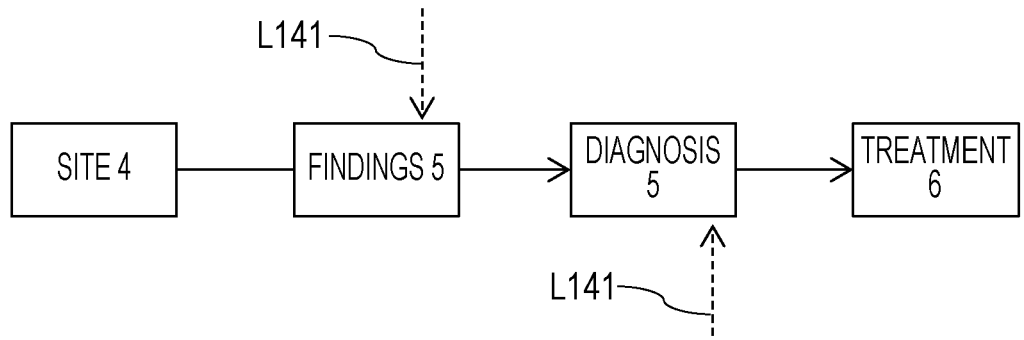
FIG. 14 is a diagram illustrating an example of a screen display in a case where there is a causal association among items that are not an object of duplication in an original past report.

FIG. 14 is a conceptual diagram illustrating the content of the report creating area 134 in a case where the site 4 in a past report has been specified and the site 4, findings 5, diagnosis 5, and treatment 6 have been duplicated in the current report, as exemplarily illustrated in FIG. 39. There are causal associations between the findings 4 and findings 5, and between the diagnosis 5 and diagnosis 6, in the past report exemplarily illustrated in FIG. 39. Marks are displayed indicating that there was a causal association such as the dotted arrow L141 in FIG. 14 serving as a display suggesting the existence of the findings 5 that is an item associated with the findings 4 but not duplicated.

After duplicating the site 4, findings 5, diagnosis 5, and treatment 6, if the radiogram interpretation physician decides to also duplicate the diagnosis 6 that is a basis for the diagnosis 5, this can be done by performing operation input of double-clicking on the dotted arrow L141 associating the diagnosis 6 with the diagnosis 5. That is, the site 6, findings 6, diagnosis 6, and treatment 7 are duplicated in the current report. In a case of having duplicated the site 6, findings 6, diagnosis 6, and treatment 7 by this operation, a causal association is automatically applied to the duplicated diagnosis 5 and diagnosis 6.

Figure 15:
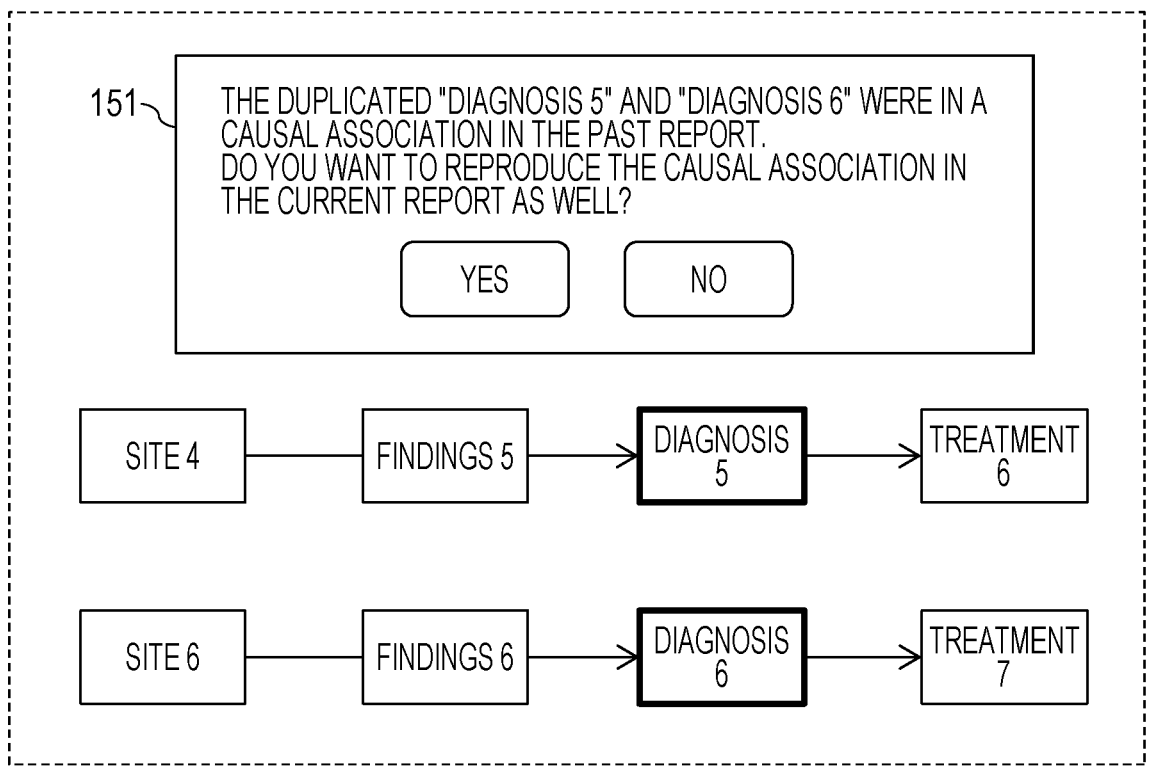
FIG. 15 is a diagram illustrating an example of a screen display for confirming whether or not to apply a causal association to duplication items which have had a causal association in an original past report.

Another input support method using the duplicate association table 703 that can be provided is to preset items each duplicated separately from past reports such that any associations in the past reports can be understood. For example, a case will be assumed where there is a past report such as in FIG. 39, selecting the site 4 has duplicated the site 4, site 5, diagnosis 5, and treatment 6, and thereafter selection of the site 6 has duplicated the site 6, findings 6, diagnosis 6, and treatment 7. Now, the diagnosis 5 and diagnosis 6 are in a causal association in the past report, so the probability of the diagnosis 5 and diagnosis 6 being associated in the current report is high. Accordingly, a message 151 illustrated in FIG. 15 is displayed by the association information presenting unit 111, and a causal association can be applied between the diagnosis 5 and diagnosis 6 by the radiogram interpretation physician pressing the "Yes" button. Thus, overlooking applying of associations can be prevented.

Sixth Embodiment

A sixth embodiment of the present invention will be described. In the present embodiment, the duplication range deciding unit 110 identifies, based on the type of specified item, part of the items directly or indirectly associated with a specified item as being in the duplication range.

For example, the range of duplication is identified as being from the site up through the report item specified in S804 in FIG. 8 out of the logical association of the flow of site, findings, diagnosis, and treatment. That is, items upstream from the specified item in the above logical association are identified. Specifically, the duplication range deciding unit 110 does not perform the processing of S903 in FIG. 9 but performs the processing of S901, S902, and S904, whereby such items are identified.

A description will be provided regarding where the duplication range deciding unit 110 identifies the duplication range a case where a report item of the type diagnosis has been specified. There are cases in radiogram interpretation reports where a diagnosis made based on certain findings serves as the basis for diagnosis according to different findings. It is also important to present on what basis the diagnosis was reached when the radiogram interpretation physician presents a diagnosis to the ordering party. Accordingly, in the present embodiment the duplication range deciding unit 110 performs processing where, in a case where a report item of the type diagnosis is selected in S804, a different report item serving as the basis for the specified report item is included in the duplication range.

Specifically, the duplication range deciding unit 110 references the association table 702 H, and performs processing using the function SelectLeftItem in S902 on the other report items serving as a basis for the selected diagnosis report item. The report items of treatment associated with the other diagnosis report items do not have to be included. So the processing using the function SelectRightItem in S903 is not performed. Next, the duplication range in a case where a report item of the type treatment has been selected will be described.

Descriptions that can be associated with almost any sort of diagnosis content, such as "CT imaging from another angle requested" or "please further evaluate" may have been described. Accordingly, in a case where the user has selected a diagnosis item in S804, the contents of report items included in the information of site, findings, and diagnosis, associated with this diagnosis report item, are not duplicated in the current report, only the contents of the treatment are duplicated in the current report.

In a case where the type of report item specified in S804 is treatment, only the selected report item is identified. Specifically, the processing using the function SelectLeftItem in S902 is not executed, and the duplication range is identified by performing S901, the processing using the function SelectRightItem in S903, and S904, are performed, thereby identifying the duplication range. In a case where the type of report item selected in S804 is site or findings, the duplication range deciding method according to the first embodiment is used as described in the first embodiment.

According to the above processing, in a case where findings 2 is specified in the past report in FIG. 39 for example, site 2, findings 2, diagnosis 2, and treatment 2 are identified as the duplication range. In a case where findings 2 is specified in the past report in FIG. 39, the diagnosis 1, findings 1, and site 1 are identified as the duplication range, in addition to the site 2, findings 2, diagnosis 2, and treatment 2. If treatment 2 is selected in the past report in FIG. 39, just the treatment 2 is selected as the duplication range.

Seventh Embodiment

A seventh embodiment according to the present invention will be described. In the present embodiment, the duplication range deciding unit 110 identifies a part of items directly or indirectly associated with a specified item as the duplication range, based on the object of the order for creation of the current report, which is the duplicate. The present embodiment also applies processing of replacing a soft copy of a medical image at the original with a soft copy of a medical image at the duplicate, as described in the second embodiment. That is, in a case where the type of the duplicated in S8061 is site, and the content thereof is a soft copy of a medical image, the medical image is replaces with a corresponding medical image currently imaged, and then the duplication processing is performed. Objects of the order for creation of a radiogram interpretation report metastasis detection, include evaluation of effectiveness of treatment, further evaluation, benign/malignant diagnosis (screening), follow-up, and so forth. Description will be made with reference to FIGS. 16A and 17B.

Figure 16A:
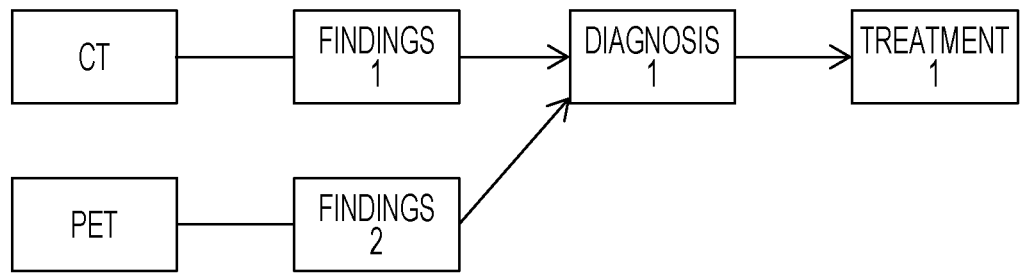
FIGS. 16A and 16B are diagrams illustrating examples of an original past report in a case where the object of order for a report being newly created is a benign/malignant diagnosis or a metastasis search.
Figure 16B:
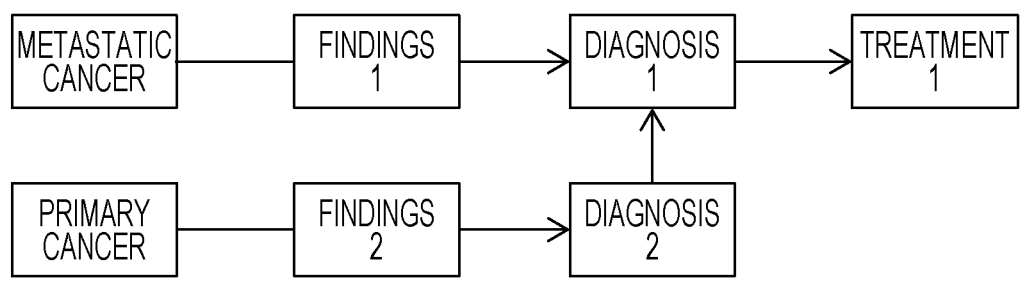

First, the duplication range in a case where the object of the order for the current report is metastasis detection or benign/malignant diagnosis. The object of metastasis detection is to detect metastasis of a tumor. The object of benign/malignant diagnosis is to determine whether a tumor is benign or malignant. There are cases in radiogram interpretation aimed at metastasis detection or benign/malignant diagnosis where diagnosis is made based on findings derived from CT images and PET images. With regard to metastasis detection, there are cases where description relating to the primary cancer that is the cause of the metastasis is also described along with a causal association, in addition to description relating to the discovered metastasis. Accordingly, in a case where the object of the order for the current report is metastasis detection or benign/malignant diagnosis, one or the other of a CT image and PET image is identified as being in the duplication range, the other image that is associated is also included in the duplication range. In the same way, in a case where one or the other of the primary cancer and the metastasis is identified as being in the duplication range, the other item is also included in the duplication range. FIG. 16A illustrates the content of a past report, displayed in the past report items and association information display area 147 when creating the current report of which the object of the order is benign/malignant diagnosis. For example in a case of selecting the CT image in FIG. 16A in S804, the CT, findings 1, diagnosis 1, and treatment 1 are included in the duplication range, by S901, S902, and S903 in FIG. 9. In a case where there is a report item derived from a PET image that is also an item including association information with a CT image or one of the images derived from the CT image, the duplication range deciding unit 110 identifies the PET image and the items derived from the PET image as being within the duplication range. In FIG. 16A, the items of PET and findings 2 are also included in the duplication range. FIG. 16B illustrates the content of a past report, displayed in the past report items and association information display area 147 when creating the current report of which the object of the order is metastasis detection. For example in a case of selecting the metastasis cancer image in FIG. 16B in S804, the metastasis cancer, findings 1, diagnosis 1, and treatment 1 are included in the duplication range, by S901, S902, and S903 in FIG. 9. In a case where there is a report item derived from the primary cancer that is also an item including association information with one of the findings 1, diagnosis 1, and treatment 1 derived from metastasis cancer and primary cancer, the item of the primary cancer and the report items derived from the item of primary cancer are identified as being within the duplication range. In FIG. 16B, the items of primary cancer, findings 2, and diagnosis 2 are included in the duplication range.

Although an example of using both CT and PET for diagnosis has been described above, the present embodiment is not restricted to this. Sets of types of examination images that are often used at the same time can be set beforehand, such as metastasis detection and benign/malignant diagnosis, and the above processing carried out.

Figure 17A:
FIGS. 17A and 17B are diagrams for describing processing relating to duplication according to a seventh embodiment.
Figure 17B:
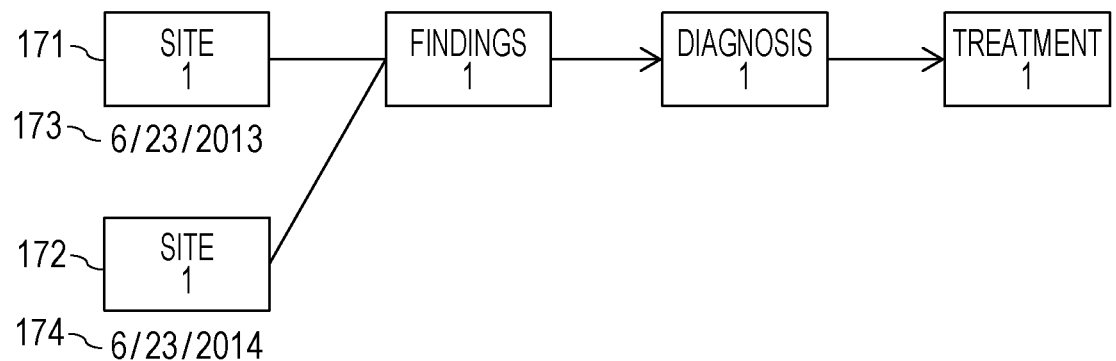

Next, description will be made regarding the duplication range in a case where the object of the order for the current report is follow-up or evaluation of effectiveness of treatment. Both follow-up and evaluation of effectiveness of treatment compare the state of the site at the point of a previous examination with the state of the site at the point of the current examination. Accordingly, the current report can contain medical images acquired from the current inspection and medical images of past examinations (in the past report) to serve as an object of comparison. In a case where the object of the order for the current report is follow-up or evaluation of effectiveness of treatment, and an image of a past report has been identified as being in the duplication range, the duplication range deciding unit 110 first acquires information of the examination where the image in the past report was obtained. The report item creating unit 102 then acquires the image of the current inspection based on the information of the examination. The report display control unit 109 displays the image in the past report and the image from the current inspection in tandem in the editing screen of the current port. Displaying the image in the past report and the corresponding image of the current report in tandem enables the ordering physician to easily compare these images. FIG. 17A is a conceptual diagram of the content of a past report displayed in the past report items and association information display area 147. FIG. 17B illustrates the results of duplication in the current report in a case where the object of the order for the current report is follow-up or evaluation of effectiveness of treatment, and a report item 170 has been specified in S804. A report item 171 is a soft copy of the medical image showing the same content as the report item 170. A report item 172 is a soft copy of a medical image acquired in the current inspection, corresponding to the site of the report item 170. The report item 172 is created by way of the processing of S131, S132, and S133 in FIG. 13. Attaching the soft copy of the previously acquired medical image and the soft copy of the currently acquired medical image, in tandem, allows the radiogram interpretation physician to omit the operation of attaching the currently acquired medical image. Note that the date at which the medical image was acquired can be automatically displayed such as indicated by reference numerals 173 and 174, so that which attached medical image is past and which is current can be easily discerned.

Eighth Embodiment

An eighth embodiment will be described. In the present embodiment, the duplication range deciding unit 110 identifies a part of items directly or indirectly associated with a specified item as being in the duplication range, in accordance with a state of description of the current report which is the duplicate, or content which conceivably will be described therein at a later point. The present embodiment also applies processing of replacing a soft copy of a medical image at the original with a soft copy of a medical image at the duplicate, as described in the second embodiment. That is, in a case where the type of the duplicated in S8061 is site, and the content thereof is a soft copy of a medical image, the medical image is replaces with a corresponding medical image currently imaged, and then the duplication processing is performed. Description will be made with reference to FIGS. 18A through 20.

FIGS. 18A and 18B illustrate an example of the present embodiment. FIG. 18A is the content of a past report displayed in the past report items and association information display area 147. FIG. 18B is the current report being edited in the report creating area 134. A report item 180 is a soft copy of a past image, and a report item 181 is a soft copy of the current image corresponding thereto. The report item 180 and the report item 181 are associated as illustrated in table 71f in FIG. 12. The findings 2 is associated with the report item in report item 181. Assumption will be made that a user has selected the report item 180 in S804 in such a state. In the present embodiment, site 1 and findings 2 have already been described in the duplicate report, the duplication range is set to just diagnosis 1 and treatment 1. FIGS. 18C1 and 18C2 are both examples of the contents of the report creating area 134 after the duplication processing. The diagnosis 1 and treatment 1, that are the object of duplication, are automatically associated with the findings 2 associated with the report item 181 corresponding to the report item 180, as illustrated in FIG. 18C1. Alternatively, the duplication range us set to findings 1, diagnosis 1, and treatment 1, and the findings 1, diagnosis 1, and treatment 1, that are contained in the duplication range are merged with the findings 2 associated with the report item 181 corresponding to the report item 180. Although an example has been described here regarding a case where a report item with the type of site has been selected as the object of duplication, duplication processing can be performed based on the same idea in cases where report items of other types are selected as the object of duplication.

Figure 19A:
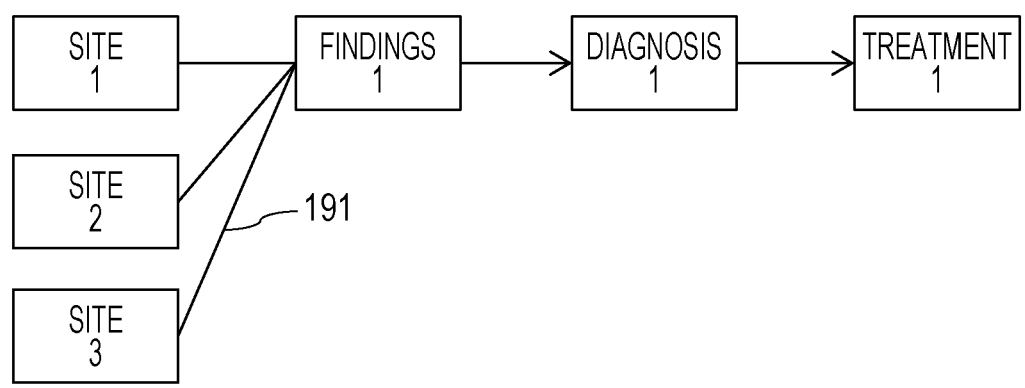
FIGS. 19A and 19B are second diagrams for describing processing relating to duplication according to the eighth embodiment.
Figure 19B:
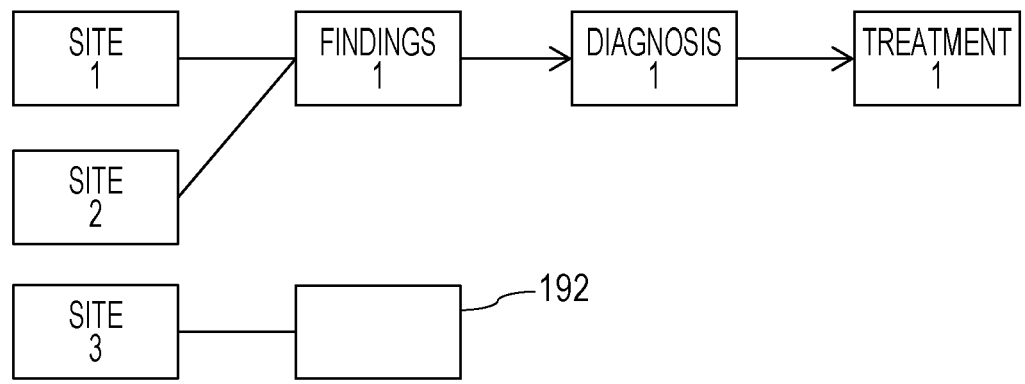
Figure 20:
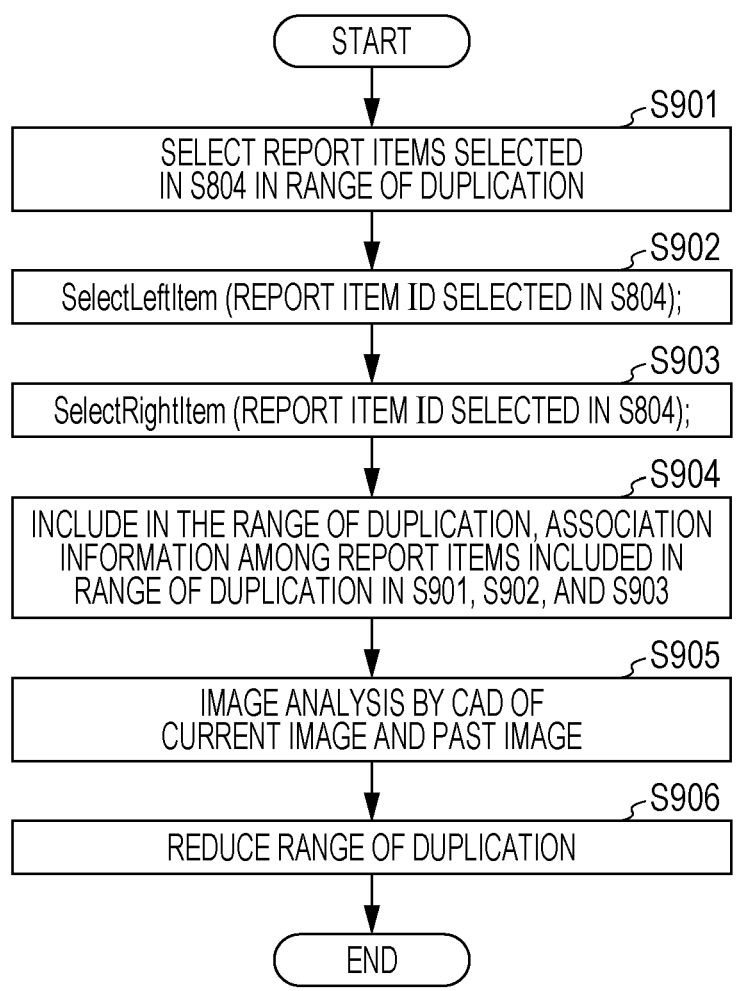
FIG. 20 is a diagram illustrating an example of procedures for processing of a duplication range deciding unit according to the eighth embodiment.

FIGS. 19A and 19B illustrate a second example of the present embodiment. FIG. 19A illustrates the content of a past report displayed in the past report items and association information display area 147. FIG. 19B illustrates the contents of the current report being edited in the report creating area 134, and is an example of a result of specifying findings 1 in FIG. 19A and including duplicated the specified duplication range. FIG. 20 is a diagram illustrating the duplication range deciding flow by the duplication range deciding unit 110 in the second example of the present embodiment. S901 through S904 are the same as in FIG. 9, with S905 and S906 having been added. For example, assumption will be made that the course of progress of multiple sites is the object of radiogram interpretation, for follow-up or the like. This example will assume that a collective description had been made in findings 1 to the effect that there is "no change at any" regarding site 1, site 2, and site 3 in the first follow-up observation, as illustrated in FIG. 19A, and that the current report is being created regarding a second follow-up observation. Upon findings 1 in FIG. 19A being specified in S804, the site 1, site 2, site 3, findings 1, diagnosis 1, treatment 1, and the association information between these in FIG. 19A, are identified as the duplication range, by the processing of S901 through S904. In S905, image analysis by computer assisted diagnosis (CAD) is performed regarding the past images of site 1, site 2, and site 3, that are soft copies of past images, and current images corresponding to these. Assumption will be made that as a result of image analysis, no change between the past images and current images is observed for site 1 and site 2, for example, but that the situation of the lesion at site 3 has markedly deteriorated. In such a state, if the site 3 is duplicated in the current report, the possibility that the associated content will not be "no change at any" as with findings 2 is high. Accordingly, operation is performed in S906, such that objects that have been found in S905 to be objects that should not maintain the same association information as in the past report, are not identified as being in the duplication range. In the above example, association information 191 that is the association between site 3 and findings 1 in FIG. 19A is not identified as being in the duplication range. The report item of site 3 still remains an object of duplication. If the duplication objects decided in the duplication range deciding flow in FIG. 20 are duplicated in the current report, the results will be as in FIG. 19B, for example. The site 1, site 2, findings 1, diagnosis 1, treatment 1, and the association information therebetween in FIG. 19B have been duplicated based on the site 1, site 2, findings 1, diagnosis 1, treatment 1, and association information therebetween, in FIG. 19A, by the processing of S806 according to the first embodiment. Site 3 in FIG. 19B also is the site 3 in FIG. 19A that has been duplicated by the processing of S806 according to the first embodiment. On the other hand, report item 192 and association information between the report item 192 and the site 3 are automatically created after S806. Note that the report item 192 is in a state where the column "content" is unregistered in the item table 701, i.e., the report item input frame 135 is blank. The radiogram interpretation physician describes findings regarding the site 3 in the report item 192, and adds diagnosis and treatment as necessary. The work of the physician performing operation after the duplication can be reduced by adjusting the duplication range beforehand in accordance with the content to be described in the current report after duplication, in the same way as in the second example in the present embodiment. Although an example has been described here where unnecessary association information is eliminated, the present embodiment is not restricted to elimination of association information, and report items can be eliminated as necessary. Although description has been made in the above example regarding adjusting the duplication range by deleting unnecessary duplication items, adjustment can be made by adding necessary duplication items.

Ninth Embodiment

A ninth embodiment will be described. An example will be described in the present embodiment regarding an example of having an evaluation unit to give evaluations to each report item, and further the duplication range deciding unit 110 identifying a duplication range in accordance with the result is comparing the evaluation value of each item with a predetermined threshold value. Description will be made by exemplary illustration with reference to FIGS. 21 and 22.

Figure 21:
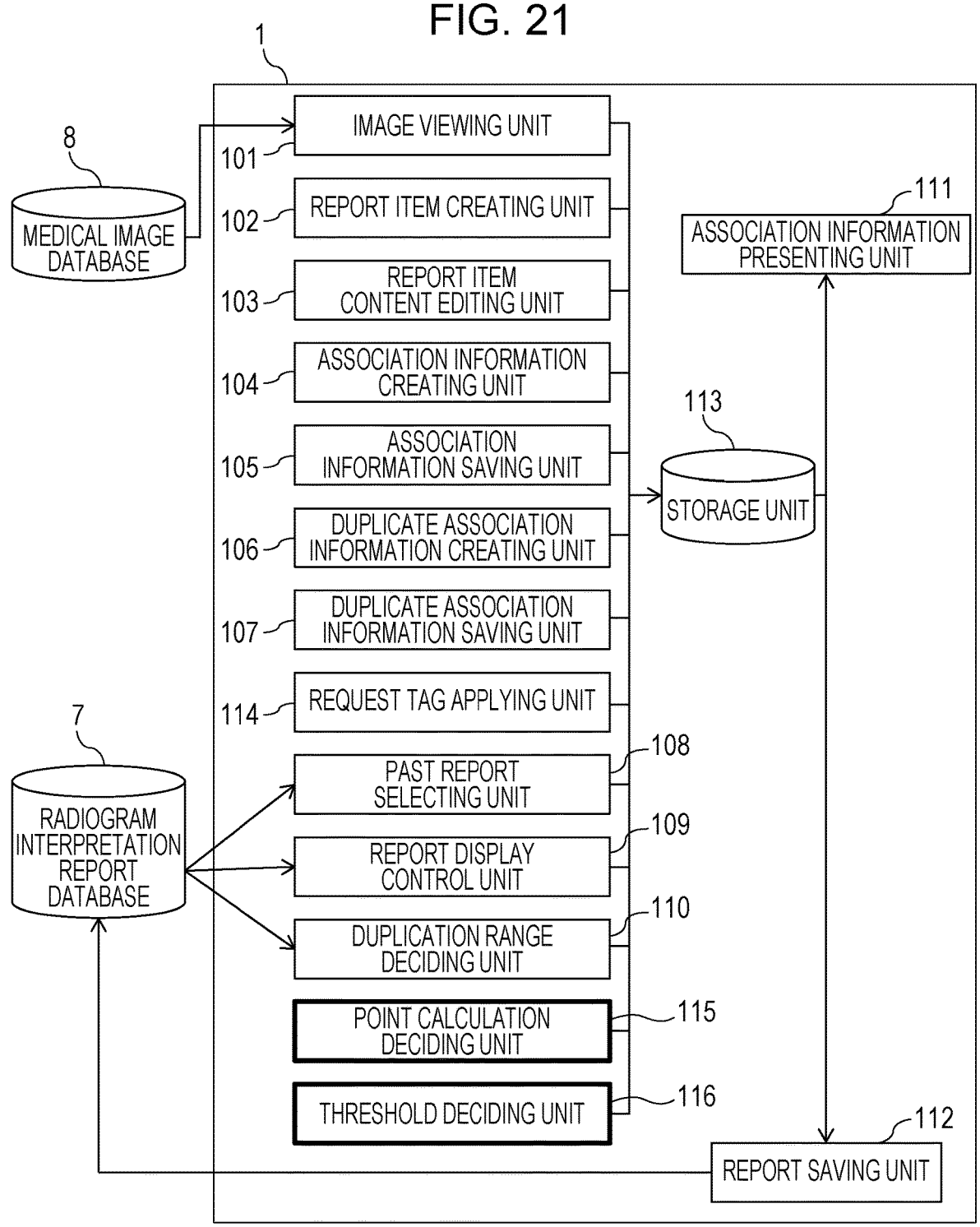
FIG. 21 is a diagram illustrating an example of functions of a medical report creating apparatus according to a ninth embodiment.
Figure 22:
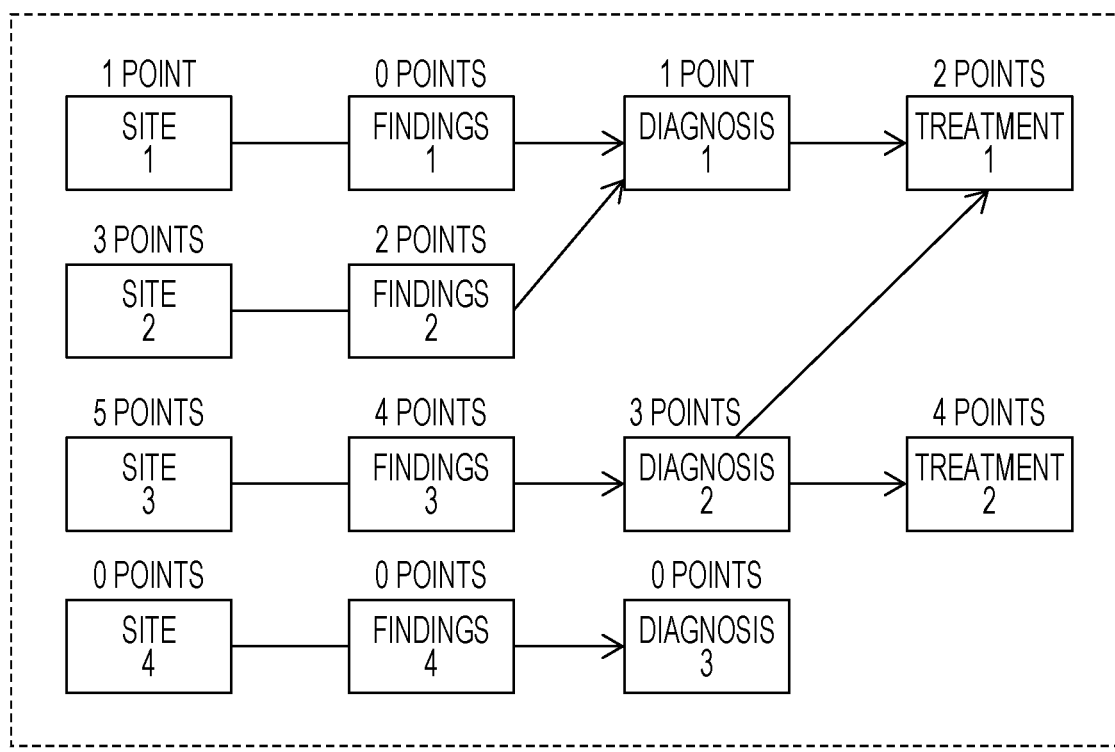
FIG. 22 is a diagram illustrating an example of content of a past report, in a state where values have been allocated to items by a point calculation deciding unit according to the ninth embodiment.

FIG. 21 is a functional block diagram for describing primary functions of the medical report creating apparatus 1 according to the present embodiment. The functional blocks 101 through 112 illustrated in FIG. 21 are the same as in FIG. 5. In S805, a point calculation deciding unit 115 acquires evaluation values of the item specified in S804 and of the items directly or indirectly associated with the item specified in S804. A threshold deciding unit 116 decides a threshold value, that is a value to compare the evaluation values given by the point calculation deciding unit 115 with, at the time of the duplication range deciding unit 110 determining whether or not to identify each item as being in the duplication range. In S805, the duplication range deciding unit 110 in the present embodiment compares the evaluation values given by the point calculation deciding unit 115 with the threshold value, and identifies items having an evaluation value less than the threshold value, for example, as being in the duplication range. FIG. 22 illustrates the content of a past report displayed in the past report items and association information display area 147. Points given to each item by the point calculation deciding unit 115, a case where the item specified in S804 is findings 1, are shown. In the example in FIG. 22, the evaluation values of items directly associated to the item specified in S804 are small, and the more indirect the association, the larger the evaluation value is; however, the evaluation value acquisition method is not restricted to this. In a case where the threshold value decided by the threshold deciding unit 116 is 2, the duplication range deciding unit 110 identifies the site 1, findings 1, and diagnosis 1 to be items that are the object of duplication. In a case where the threshold value decided by the threshold deciding unit 116 is 3, the duplication range deciding unit 110 identifies the site 1, findings 1, diagnosis 1, treatment 1, and findings 2, to be items that are the object of duplication.

Examples of the threshold deciding unit 116 deciding the threshold value will be described. In a first example, the threshold value is decided in accordance with the object of the order, which has been described in the seventh embodiment. In a case where the object of the order for the current report is metastasis detection or benign/malignant diagnosis, diagnosis can be performed based on both findings of CT and PET. A situation will be considered where, for example, the item selected in S804 is site, the content thereof is a soft copy of a medical image, and the medical image is a CT image. In this case, if there is an image associated with a PET image used for diagnosis along with the selected CT medical image in the past report items and association information display area 147, the magnitude of the threshold value is expanded so that this item is included in the duplication range. In both follow-up and evaluation of effectiveness of treatment, the site at the point of the previous examination and the state of the site in the current examination are often compared. Accordingly, the magnitude of the threshold value is expanded so that at least one of sites directly or indirectly associated with the item selected in S804 is included in the duplication range.

In the second example, the threshold value is decided in accordion with the type of lesion, site, or modality, or type of combination thereof. In this case, in addition to the functional blocks listed in FIG. 21, there also is provided a distinguishing unit that distinguishes the type of lesion, site, or modality, or type of combination thereof, described in the contents of the item specified in S804. For example, in a case where there are words relating to a lesion necessitating complicated study in the contents of an item specified in S804, study is often made in the report based on information made up of a great number of items. Accordingly, in a case where are words relating to a lesion necessitating complicated study, the threshold value is set larger, in order to identify a greater number of items as being in the duplication range, as compared to otherwise.

Tenth Embodiment

A tenth embodiment will be described. In the present embodiment, processing to allocate evaluation values to the items by the point calculation deciding unit 115, and processing to compare the evaluation values of each item with the threshold value decided by the threshold deciding unit 116, are sequentially executed at each item. The items to be included in the duplication range are decided sequentially in accordance with the comparison results thereof. Description will be made by exemplary illustration with reference to FIGS. 23 through 25.

Figure 23:
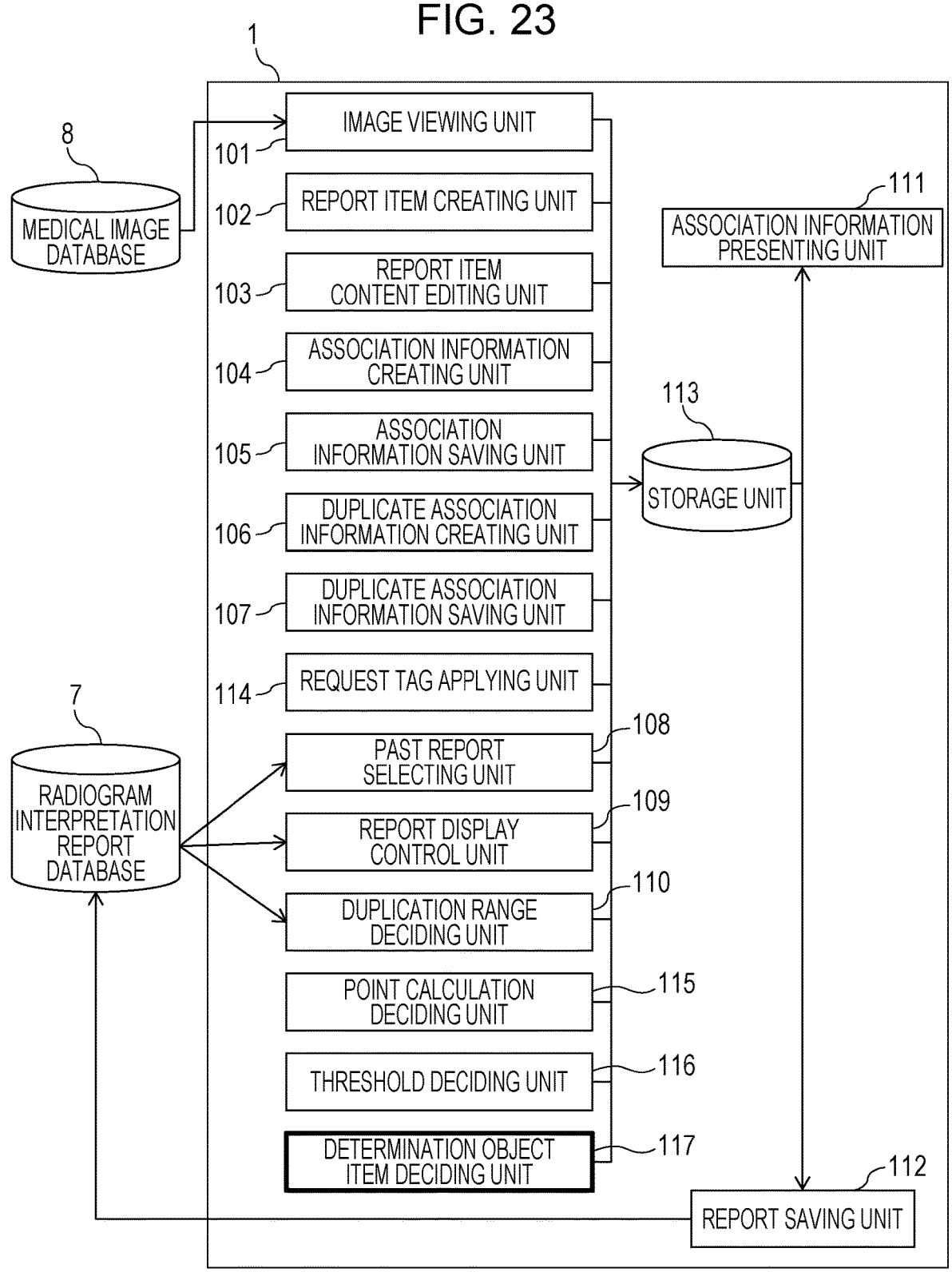
FIG. 23 is a diagram illustrating an example of functions of a medical report creating apparatus according to a tenth embodiment.
Figure 24A:
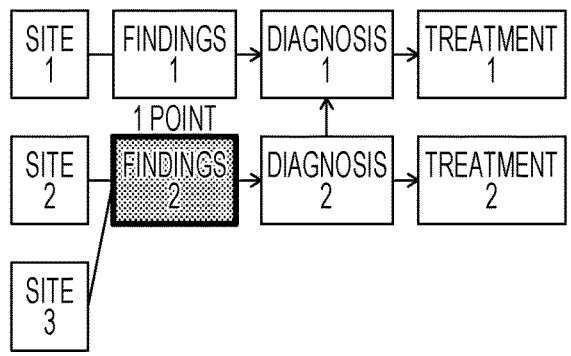
FIGS. 24A through 24H are examples of diagrams for describing an operation flow by a duplication range deciding unit in the tenth embodiment.
Figure 24B:
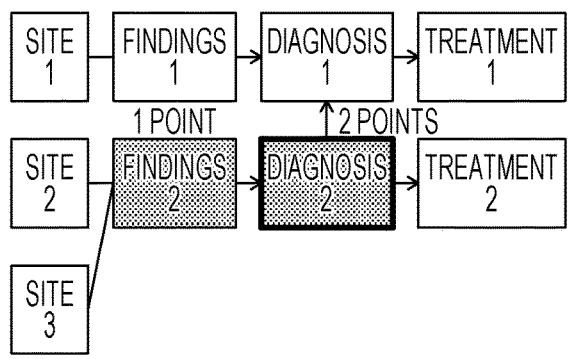
Figure 24C:
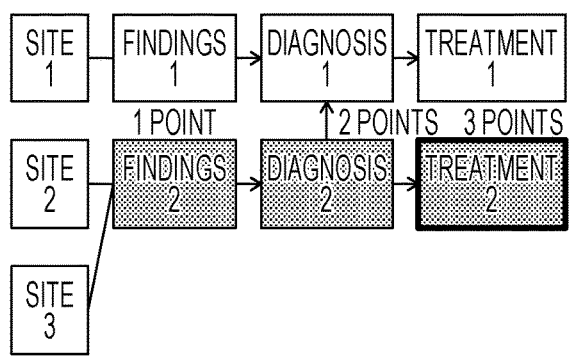
Figure 24D:
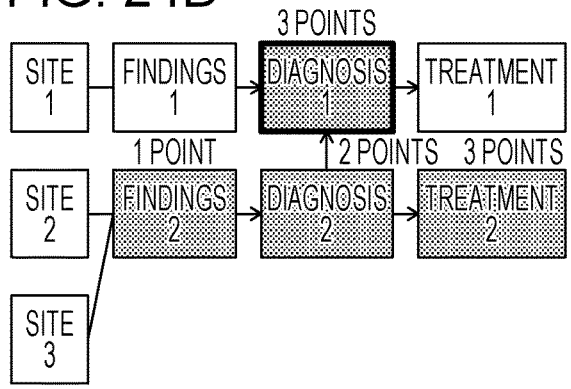
Figure 24E:
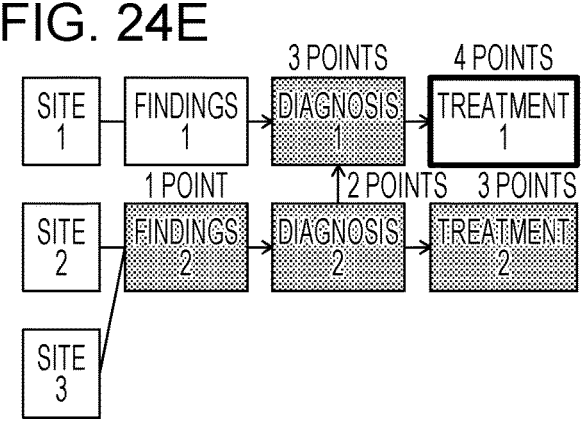
Figure 24F:
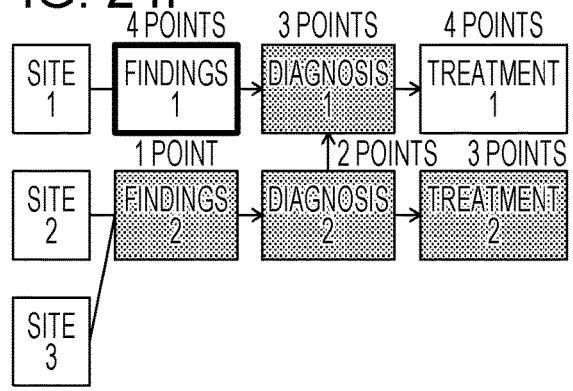
Figure 24G:
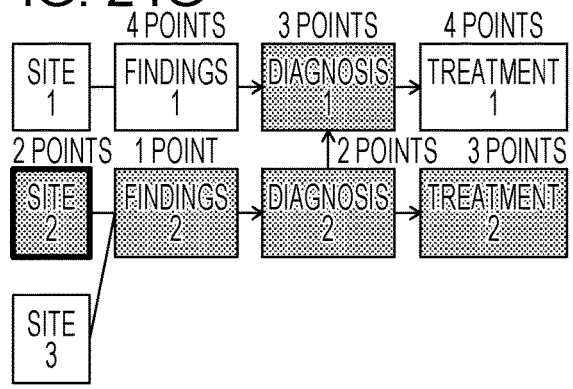
Figure 24H:
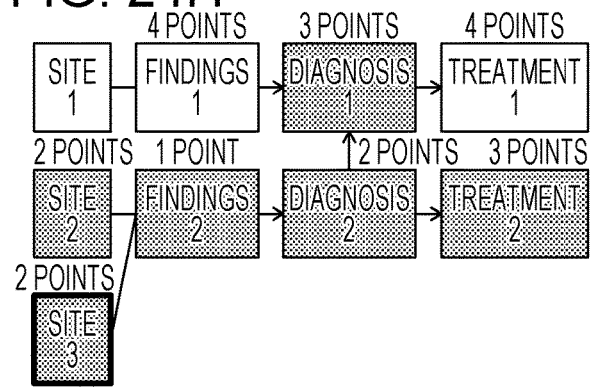
Figure 25:
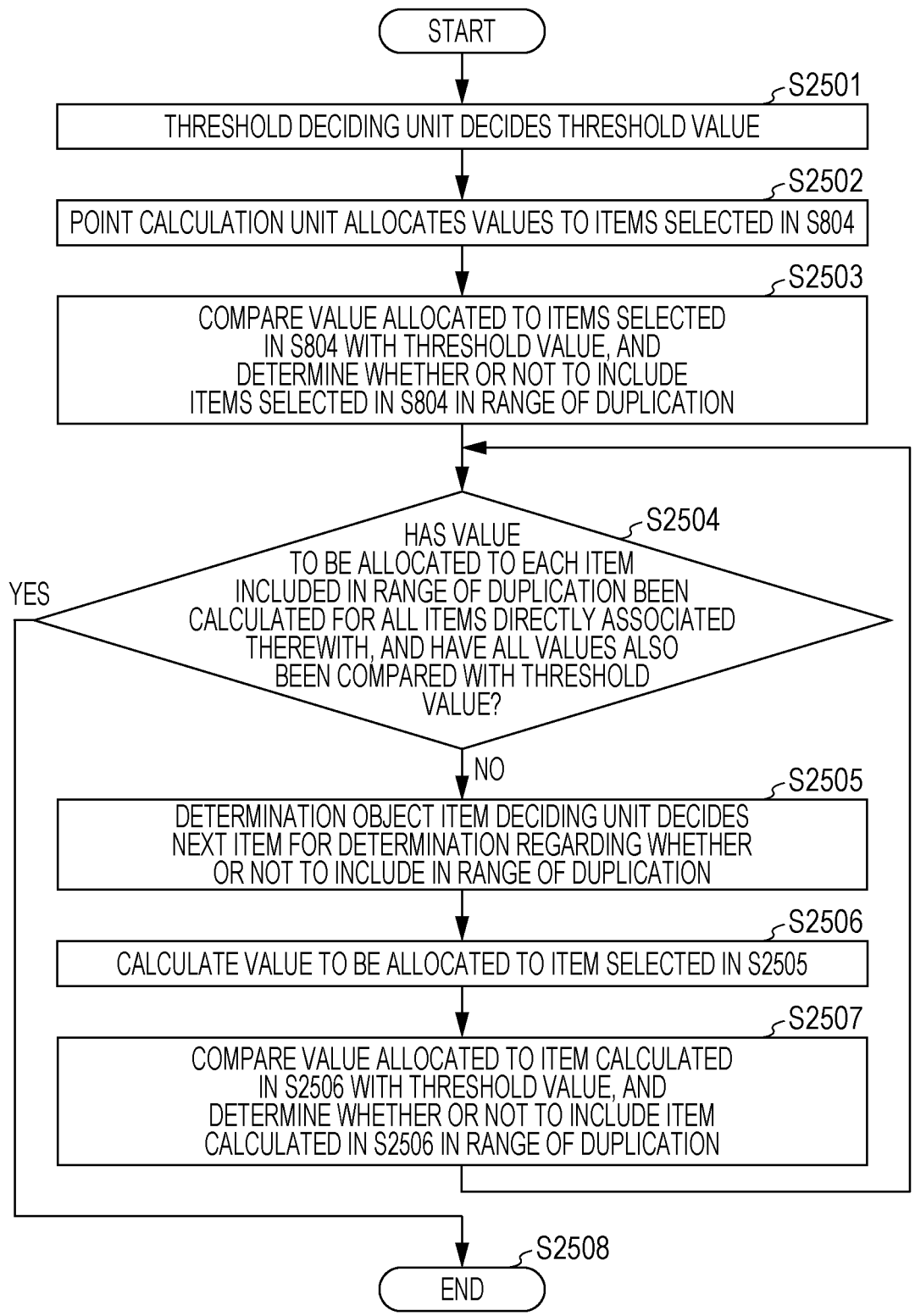
FIG. 25 is a diagram illustrating an example of an operation flow by the duplication range deciding unit in the tenth embodiment.

FIG. 23 is a functional block diagram for describing primary functions of the medical report creating apparatus 1 according to the present embodiment. The functional blocks 101 through 116 are the same as in FIG. 21. The point calculation deciding unit 115 according to the present embodiment acquires an evaluation value for each item, based on the evaluation value of an item directly associated with that item. A determination object item deciding unit 117 is allocated evaluation values by the point calculation deciding unit 115, and decides items to be compared with the threshold value. The flow of processing by the duplication range deciding unit 110 will be exemplarily illustrated with reference to FIG. 25. The contents of the past report items and association information display area 147 are illustrated in FIGS. 24A through 24H. As an example here, the point calculation deciding unit 115 acquires the evaluation value of each item as a value obtained by adding 1 to the evaluation value of an item directly associated with that item. In S2501 in FIG. 25, The threshold deciding unit 116 decides the threshold value. In this example, the threshold value is set to 4. In S2502, the point calculation deciding unit 115 allocates a value to the item specified in S804. If the item specified in S804 is the item of findings 2 illustrated in FIG. 24A, for example, 1 point is allocated to the findings 2. In S2503, the evaluation value of the item specified in S804 is compared with the threshold value, and determination is made regarding whether or not to identify the item specified in S804 as being in the duplication range. The 1 point allocated to the findings 2 in FIG. 24A is smaller than the threshold value 4, so the duplication range deciding unit 110 identifies the findings 2 as being in the duplication range. Note that in FIGS. 24A through 24H, the items having heavy border lines are items of which the evaluation value has been compared with the threshold value, and the gray items have been identified as belonging to the duplication range. In S2504, determination is made regarding whether acquisition of evaluation value, and comparison of evaluation value and threshold value, has been performed for all items directly associated for each item identified as being in the duplication range. In a case where this has been performed for all items, the flow advances to S2508, and the flow ends. IF this has not been performed for all items, the flow advances to S2505. In the case of FIG. 24A, neither acquisition of evaluation values by the point calculation deciding unit 115 for the site 2, site 3, and diagnosis 2 directly associated with the findings 2, nor comparison of the evaluation value and threshold value, have been completed, so the flow advances to S2505. In S2505, the determination object item deciding unit 117 decides an item for determination next regarding whether or not to identify as being in the duplication range. The determination object item deciding unit 117 selects an item directly associated with an item identified as being in the duplication range, to which an evaluation value has not been allocated and comparison with the threshold value has not been performed. In FIG. 24A, one of the site 2, site 3, and diagnosis 2 is selected by the determination object item deciding unit 117. A case where the diagnosis 2 has been selected will be considered here. In S2506, the evaluation value of the items selected by the determination object item deciding unit 117 in S2505 is acquired by the point calculation deciding unit 115. In the present embodiment, the evaluation value of the diagnosis 2 is obtained by adding 1 to the 1 point allocated to the findings 2, so the evaluation value is 2, as illustrated in FIG. 24B. In S2507, the value acquired in S2506 is compared with the threshold value, and determination is made regarding whether or not to include the item selected in S2505 in the duplication range. The value 2 allocated to the diagnosis 2 in FIG. 24B is smaller than the threshold value 4, so the diagnosis 2 is identified as being in the duplication range. After the processing in S2507, the flow returns to S2504 and the above-described processing is repeatedly executed. In FIG. 24C, an evaluation value of 3 is acquired for the item of treatment 2, and since this is smaller than the threshold value 4, the treatment 2 is identified as being in the duplication range. In FIG. 24D, an evaluation value of 3 is acquired for the item of diagnosis 1, and since this is smaller than the threshold value 4, the diagnosis 1 is identified as being in the duplication range. In FIG. 24E, an evaluation value of 4 is acquired for the item of treatment 1, and since this is not smaller than the threshold value 4, the treatment 1 is not identified as being in the duplication range. In FIG. 24F, an evaluation value of 4 is acquired for the item of findings 1, and since this is not smaller than the threshold value 4, the findings 1 is not identified as being in the duplication range. Note that the findings 1 is not included in the duplication range, and accordingly the site 1 is not selected by the determination object item deciding unit 117 in S2505. In FIG. 24G, an evaluation value of 2 is acquired for the item of site 2, and since this is smaller than the threshold value 4, the site 2 is identified as being in the duplication range. In FIG. 24H, an evaluation value of 2 is acquired for the item of site 3, and since this is smaller than the threshold value 4, the site 3 is identified as being in the duplication range. At this point, acquisition of evaluation value and comparison of evaluation value and threshold value has ended for each of the items identified as being in the duplication range and all items directly associated therewith. Thus, the duplication range deciding unit 110 identifies that the findings 2, diagnosis 2, treatment 2, diagnosis 1, site 2, and site 3 are the object of duplication.

Although description has been made in the above example described with reference to FIGS. 24A through 24H that the value to be allocated to the items is the value allocated to an item directly associated therewith plus 1, but the value can be otherwise acquired. For example, the value to be added can be decided in accordance with the type of the item specified in S804. Alternatively, the value to be added can be changed as appropriate in accordance with the type of association between the item that the point calculation deciding unit 115 allocates a value and the item directly associated therewith. Further, the threshold deciding unit 116 can decide the threshold value in various ways, as described with regard to the ninth embodiment.

Eleventh Embodiment

Figure 26:
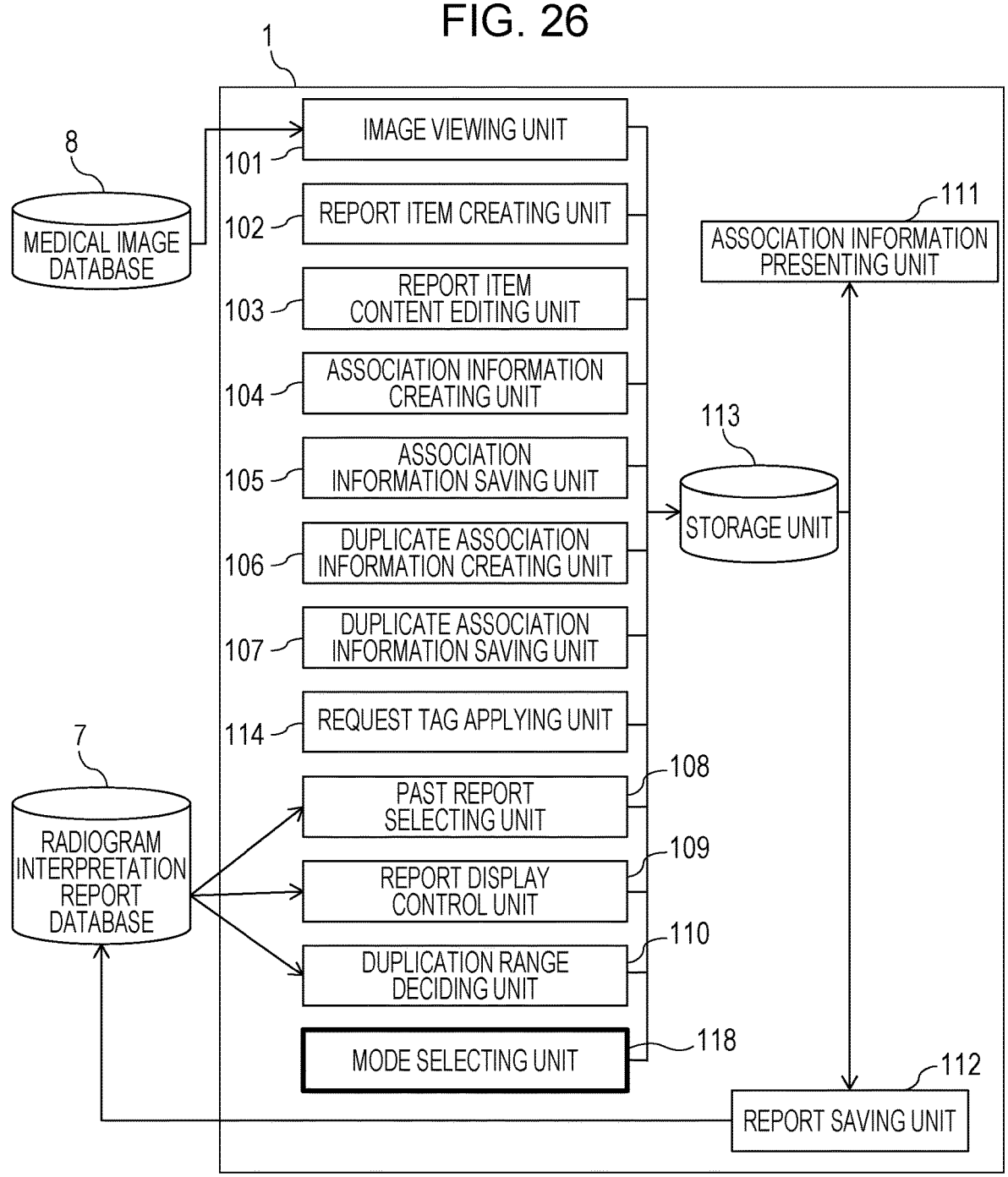
FIG. 26 is a diagram illustrating an example of functions of a medical report creating apparatus according to an eleventh embodiment.

An eleventh embodiment will be described. In the present embodiment, the duplication range deciding unit 110 can select the technique for identifying the duplication range. FIG. 26 is a functional block diagram for describing primary functions of the medical report creating apparatus 1 according to the present embodiment. The configuration is the same as that exemplarily illustrated in FIG. 7, to which a mode selecting unit 118 has been added. The mode selecting unit 118 provides a way for the duplication range deciding unit 110 to select which method to follow to identify the duplication range.

Examples of deciding methods that the duplication range follows include the following.

(1) A method of manually selecting items that the radiogram interpretation physician wants to duplicate, one at a time, with the duplication range deciding unit 110 viewing just the selected items as being the duplication range.

(2) The method according to the first embodiment, where the items selected by the radiogram interpretation physician and all other items directly or indirectly associated therewith are acquired as the duplication range.

(3) The method according to the fifth embodiment, where the items selected by the radiogram interpretation physician and part of the other items directly or indirectly associated therewith are acquired as the duplication range.

(4) The method according to the sixth embodiment, where duplication range is decided based on the type of items selected by the radiogram interpretation physician.

(5) The method according to the seventh embodiment, where duplication range is decided based on the object of the order at the duplicate.

(6) The method according to the eighth embodiment, where duplication range is decided based on the state of description at the duplicate.

The mode selecting unit 118 operates at a timing earlier than S804 in FIG. 8, and displays a list of the operations of the duplication range deciding methods (1) through (6), for example. The radiogram interpretation physician implies which to select via the input device 11, thereby selecting which of the duplication range deciding methods to select. The duplication range is decided in S805 in FIG. 8 according to the selected duplication range deciding method.

A configuration can be made where the mode selecting unit 118 is added to the functions described in FIGS. 21 and 23, described in the ninth and tenth embodiments. In this case, the mode selecting unit 118 decides what sort of algorithm the point calculation deciding unit 115 and threshold deciding unit 116 operate according to.

Twelfth Embodiment

A twelfth embodiment will be described. In the present embodiment, the duplication range deciding unit 110 decides the duplication range based on the object of the order selected by the duplication range deciding unit 110 in a case where the object of the order described in a past report has been selected in S804 of FIG. 8 in the first embodiment. Description will be made with reference to exemplary illustrations in FIGS. 27 through 29.

Figure 27:
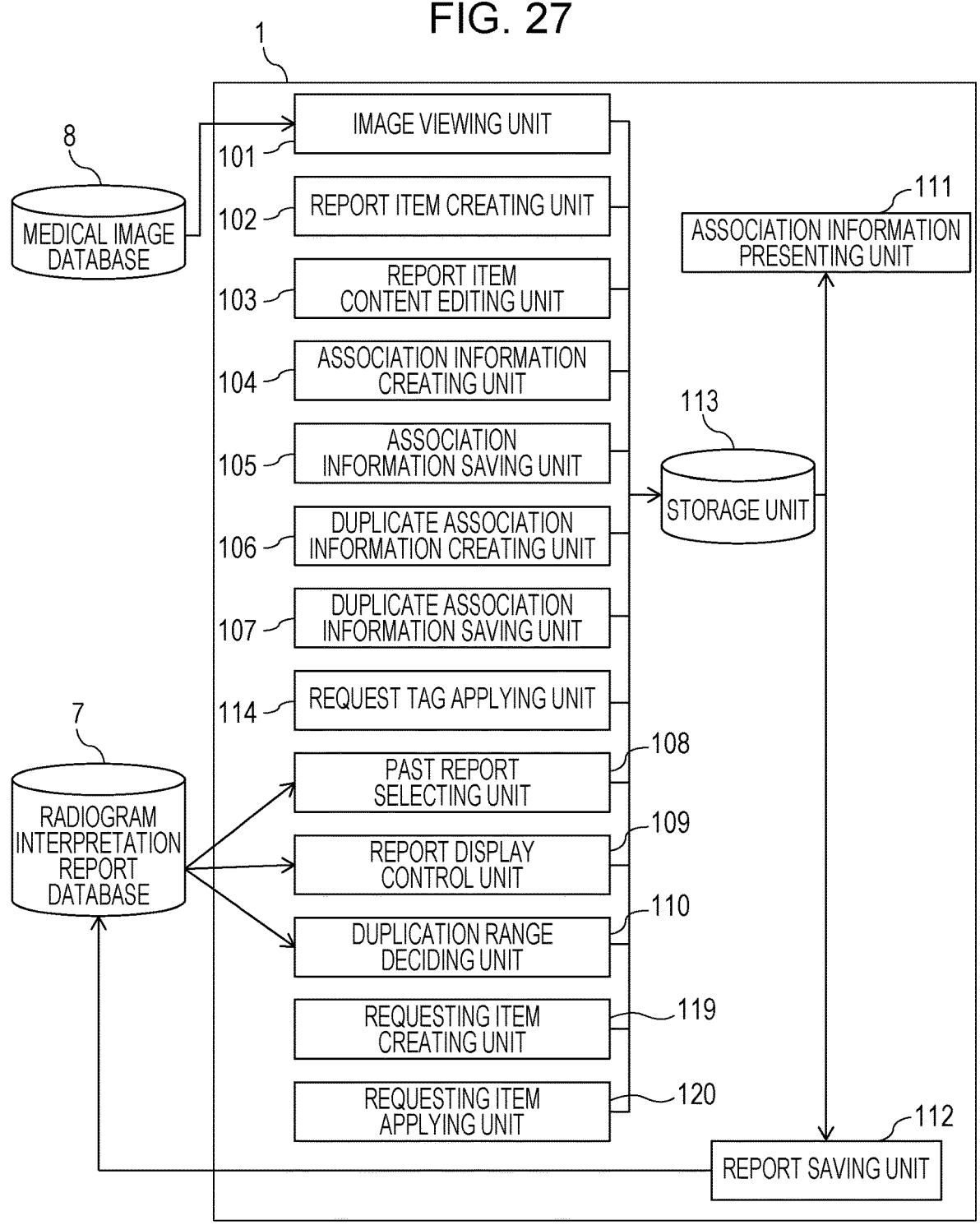
FIG. 27 is a diagram illustrating an example of functions of a medical report creating apparatus according to a twelfth embodiment.

FIG. 27 is a functional block diagram for describing primary functions of the medical report creating apparatus 1 according to the present embodiment. The configuration is the same as that illustrated in FIG. 5, to which a requesting item creating unit 119 and a requesting item applying unit 120 have been added. The requesting item creating unit 119 crates the requesting object relating to the radiogram interpretation task conveyed from the ordering physician to the radiogram interpretation physician, as an item making up order information (hereinafter referred to as "requesting item") described in the report. Further, the requesting item creating unit 119 automatically gives the created requesting item an ID for unique identification, and saves this in a requesting table 2801 illustrated in FIG. 28A. Multiple requesting items can be described in a single report, in which case multiple requesting item records are created within the requesting table 2801. The contents of the requesting table 2801 are saved in the storage unit 113. The requesting item applying unit 120 tags report items associated with the requesting item described in the requesting table 2801, so as to associate. For example, a requesting ID column is added to the item table 701, and the ID of the corresponding requesting item is saves as a requesting ID column value in the record of each report item, as illustrated in FIG. 28B. The degree of certainty column and request tag column in the item table 701 are omitted from illustration in FIG. 28B. Deciding of the requesting item and report items associated therewith can be made by user operation input, or can be automatically decided by analyzing the contents of the requesting item and report item by language analysis.

The following is a description of a duplication range deciding method by the duplication range deciding unit 110 according to the present embodiment. In the present embodiment, the duplication range is decided by the following method, at the time of a portion in a past report that is the requesting item being specified as an item of the past report, in S804. First, the item table illustrated in FIG. 28B is referenced, and a report item including the requesting ID in the requesting table 2801 in the requesting ID column in the item table, regarding the requesting item selected in S804, is identified. For example, a case will be assume where there are two requesting objects in the order information display area 146 in FIG. 29, which are the request (1) and request (2), and the user has dragged-and-dropped the request (2) to the report creating area 134. If the content of the request (2) is the requesting ID=1 in FIG. 28A, i.e., the request (2) is "CANCER OF LEFT KIDNEY, CONFIRMATION OF POSTOPERATIVE COURSE", report items of which the item ID in the item table in FIG. 28B correspond to 3 and 6 are extracted. In S805 in the present embodiment, these extracted report items are identified as the duplication range, as items specified in S804 in the first embodiment. Identifying of the duplication range is decided by a method according to any one of the methods described in the first through seventh embodiments.

While the requesting item creating unit 119, requesting item applying unit 120, requesting table 2801, and requesting ID column have been newly introduced and described in the present embodiment, the same processing as that described above can be carried out using the request tag applying unit 114 and the "request tag" column in the item table 701.

According to the duplication range deciding method of the present embodiment, radiogram interpretation contents relating to ordering objects described in past reports can be duplicated and used in a current report with simple operations, so the medical report can be efficiently created.

Modifications

In a structured report such as described in the first through twelfth embodiments, the report item content editing unit 103 can apply a template to the content of items created by the report item creating unit 102. The report display control unit 109 displays the descriptions of the template applied by the association information saving unit 105 on the display unit. That is, the report item content editing unit 103 functions as an estimating unit that estimates information to be described in items of the radiogram interpretation report being newly created, based on the contents of a past radiogram interpretation report. Also, the report display control unit 109 functions as a display control unit that displays descriptions estimated by the report display control unit 109 serving as the estimating unit, on the display unit. For example, the report item content editing unit 103 applies a template based on contents described in items in an original to items in the duplicate, at the time of report items in a past report being duplicated in the current report. A template can be applied to all items identified as the duplication range by the duplication range deciding unit 110, or the user can specify, from items identified as the duplication range, which items to apply a template to.

For example, assumption will be made that a findings item 4102 in a past report as illustrated in FIGS. 41A and 41B, stating that "MULTIPLE ENLARGEMENTS FOUND AT RIGHT RENAL LYMPH NODES. SIZES ARE 15 TO 20 mm, CONSIDERED TO BE A SIGNIFICANT SIZE." is to be duplicated into the current report. In a case where image diagnosis for follow-up is to be performed in the current report, a similar description is often made in the findings item in the current report. Accordingly, the report item content editing unit 103 edits the content of the item 4105 to read "MULTIPLE ENLARGEMENTS FOUND AT RIGHT RENAL LYMPH NODES. SIZES ARE  TO  mm, CONSIDERED TO BE A SIGNIFICANT SIZE." in the current report at the duplicate. The item at the duplicate where the template has been applied is displayed by the report display control unit 109 on the display unit. This is an example of application of a template to facilitate ease of the user inputting change in the size of the lesion of follow-up. Thus, the example described in the fourth embodiment is an example of a template when viewed from a different perspective.

Application of a template is not restricted to cases of follow-up. An arrangement can be made where the report item content editing unit 103 applies a template to make it easier for the radiogram interpretation physician to input items to be described, based on order information of the radiogram interpretation report, and the report display control unit 109 perform display on the display unit. For example, in a case where the request is regarding stage diagnosis of primary lung cancer, a template is applied that states "invasion to chest wall and major blood vessels ***." in the findings item correlated with a fluorodeoxyglucose (FDG)-PET image. Accordingly, the user can input descriptions matching the content of the request more easily. The report item content editing unit 103 can also apply a template to facilitate input of items for the radiogram interpretation physician to describe regarding items associated with an image, based on content such as conditions and order for taking the image, and the report display control unit 109 display on the display unit. Alternatively, the report item content editing unit 103 can apply a template to facilitate input of information to be described in items not yet input, and the report display control unit 109 display on the display unit. For example, a case will be assumed where a radiogram interpretation physician creates a findings item and diagnosis item associated with an FDG-PET image, and inputs a description regarding a bone in the findings item. The report item content editing unit 103 prepares a template stating "Metastasis to bone ***." for the diagnosis item associated with the findings. Further, items to which the report item content editing unit 103 applies templates is not restricted to report items created beforehand, and new items can be created by controlling the report item creating unit 102. For example, a case will be assumed where a description of "Metastasis to bone suspected." has been input to a diagnosis item associated with a FDG-PET image. The report item creating unit 102 creates a recommended item associated with this diagnosis item. The report item content editing unit 103 applies a template of "Consider taking biopsy." in the recommended item created by the report item creating unit 102. That is, the report item content editing unit 103 functions as a recommending unit that, based on information input to an item included in the radiogram interpretation report, recommends information described in an item associated with this item. The report item creating unit 102 also functions as a creating unit that creates report items based on information input to an item included in the radiogram interpretation report. The report display control unit 109 functions as a display control unit that displays, on the display unit, descriptions estimated by the report item content editing unit 103 serving as an estimating unit, and items created by the report item creating unit 102.

In the structured report described in the first through twelfth embodiments, in a case where a certain item is selected by the input device 11, the report display control unit 109 can display items associated with the selected item so as to be distinguishable from other items. Items associated with the selected item are not restricted to items contained in the same report as this item. In a case where this item has been duplicated from a past report, items associated with this item in the past report can be displayed highlighted along with the items included in the same report as this item. Also, in a case where this item has been duplicated into a newly-created item, items included in the duplicate report can also be displayed highlighted along with items included in the same report as this item. Accordingly, items associated with a certain item can be easily comprehended regarding items included in a report other than the report in which this item is included, which is useful in making comparison in time-series, for example. Associated items can include, in addition to the items of site, findings, diagnosis, and treatment, request tags of items indicating order information. Accordingly, the association with the contents of the order from the ordering physician can be easily comprehended.

In the structured report described in the first through twelfth embodiments, analysis using big data can be applied, and the results can be used.

Note that the apparatus according to the first through third embodiments is not restricted to supporting creating medical reports. The present invention can be used to support task of verifying contradicting hypotheses in various types of structure reports for logically describing the basis of analysis or study. Examples of information systems used in the office or the like can include systems for sharing information, such as accounting, product inventory management, document management and searching, and so forth. There also are more systems where individual operations, such as receiving payments, making payments, placing orders and back orders, delivery and like procedures, analysis of sales and so forth, are coordinated. There are cases where such information systems are used and reports or the like are created describing analyses and the results of studying measures, based on advanced knowledge and experience. Such reports and the like often include attached electronic data, digital photographs, and images. The bases for such analysis and study need to be logically described, to shown the validity of the results of the analysis and study of measures. The support for creating structured reports according to the present invention can be used to deal with such issues.

Thus, when using a part of items described in medical reports created in the past in a report being newly created, items to be referred to at the same time can be easily identified. Accordingly, the trouble of the user confirming medical reports created in the past can be reduced.

The present invention can be realized by processing where a program realizing one or more functions of the above-described embodiments is supplied to a system or apparatus via a network or storage medium, and one or more processors of a computer in the system or apparatus reading out and executing the program. The present invention can also be realized by a circuit realizing one or more functions (e.g., an application-specific integrated circuit (ASIC)).

The medical report creating apparatus according to the above embodiments can be realized as a standalone apparatus or can be an arrangement where multiple information processing apparatuses are combined to be mutually communicable and execute the above-described processing. The above processing can be executed by a shared server device or server group. It is sufficient for the multiple apparatuses embodying the medical report creating apparatus and medical report creating support system to communicate at a predetermined communication rate and do not need to be situated within the same facility or nation.

An arrangement where a software program realizing the functions of the above-described embodiments is supplied to a system or apparatus, and a computer of the system or apparatus reads out and executes the supplied program code is included in embodiments of the present invention.

Accordingly, the program code itself that is installed to a computer to realize the processing according to the embodiments on a computer also is an embodiment of the present invention. Further, an operating system (OS) or the like running on the computer can perform part or all of the actual processing based on instructions included in the program read out by the computer, and the functions of the above-described embodiments can be realized by that processing.

Arrangements where the above-described embodiments are combined as suitable are also included in the embodiments of the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While aspects of the present invention have been described with reference to exemplary embodiments, it is to be understood that the aspects of the invention are not limited to the disclosed exemplary embodiments. The scope of the following claims is to be accorded the broadest interpretation so as to encompass all such modifications and equivalent structures and functions.

This application claims the benefit of Japanese Patent Application No. 2015-152089, filed Jul. 31, 2015, Japanese Patent Application No. 2015-185268, filed Sep. 18, 2015, and Japanese Patent Application No. 2015-188193, filed Sep. 25, 2015, which are hereby incorporated by reference herein in their entirety.

What is claimed is:

1. An information processing apparatus comprising:
a memory storing a program; and
one or more processors which, by executing the program, function as:
a creating unit configured to create a medical report including a plurality of sets of information that are an object of diagnosis and association information indicating associations among a plurality of items included in the plurality of sets of information, wherein items in the plurality of items include images, information of findings, information of diagnosis, and information of treatment, wherein the association information describes respective associations between the images, the information of findings, the information of diagnosis, and the information of treatment, wherein the respective associations include one or more of correspondence associations, causal associations, and exclusive associations, and wherein the medical report is stored in one or more storage units;
a specification unit configured to specify one item, in response to receiving a user instruction from an input device that indicates the one item, out of a plurality of items included in a plurality of sets of information included in a first medical report stored in the one or more storage units, wherein the first medical report includes respective association information;
an identifying unit configured to identify, based on the association information included in the first medical report, at least one associated item, of the plurality of items included in the first medical report, associated with the one item specified by the specification unit in response to specification by the specification unit;
a duplication processing unit configured to duplicate the one item specified by the specification unit and the at least one associated item identified by the identifying unit in a second medical report in response to identifying by the identifying unit, wherein the second medical report includes respective association information, and wherein the second medical report is stored in the one or more storage units; and
a display control unit configured to display the second medical report, including items duplicated by the duplication processing unit and the respective association information of the second medical report, for interpretation or diagnosis and to change a display layout of the second medical report between a first layout that shows associations defined by association information of the second report and a second layout that does not show the associations defined by the association information of the second report.

2. The information processing apparatus according to claim 1,
wherein the display control unit displays information including predetermined attributes included in the at least one item identified by the identifying unit and information not including the predetermined attributes in a distinguishable manner.

3. The information processing apparatus according to claim 2, wherein the predetermined attributes include at least one of information relating to size of a lesion that is the object of diagnosis, information relating to volume of a body organ that is the object of diagnosis, information relating to degree of progression of a lesion that is the object of diagnosis, or stage classification that is the object of diagnosis.

4. The information processing apparatus according to claim 2, wherein the display control unit further displays an icon performing operation input indicating that creation of the medical report has been completed, and wherein the display control unit displays a warning in a case where operation input is performed to the icon without information having the predetermined attributes having been changed.

5. The information processing apparatus according to claim 1, further comprising:

an image acquisition unit configured to, in a case where an image included in the first medical report has been identified by the identifying unit, acquire information of an examination where the identified image was acquired, and acquire an image of the object of diagnosis acquired of a region corresponding to the identified image based on the information of the examination.

6. The information processing apparatus according to claim 5,
wherein, in a case where creation of the medical report has been ordered for follow-up of the object of diagnosis and an image of the first medical report is included in the at least one item identified by the identifying unit, the image acquisition unit acquires the image based on the information of the examination in which the image in the first medical report was acquired and on the order, and
wherein the display control unit displays the image identified by the identifying unit and the image acquired by the image acquisition unit in tandem for editing the medical report.

7. The information processing apparatus according to claim 5, wherein, in a case where an image included in the first medical report is identified by the identifying unit and an image of the object of diagnosis corresponding to the identified image can be acquired, the display control unit displays, in a screen for editing the medical report, the identified image and the image acquired by the image acquisition unit, in accordance with operation input as to the image that is the object of diagnosis corresponding to the identified image, and
wherein, in a case where an image included in the first medical report is identified by the identifying unit but an image of the object of diagnosis corresponding to the identified image cannot be acquired, the display control unit displays, in a screen for editing the medical report, an item associated with the at least one item identified by the identifying unit as an item for displaying an image.

8. The information processing apparatus according to claim 1, wherein the at least one associated item includes a plurality of associated items, and
wherein the identifying unit is configured to identify the plurality of associated items of the plurality of items included in the first medical report further based on a duplication range.

9. The information processing apparatus according to claim 1, wherein, in a case where the specification unit has specified information for ordering creating of the first medical report based on receipt of user operation, the identifying unit identifies an item included in the first medical report that corresponds to the information for ordering.

10. The information processing apparatus according to claim 1, wherein, in a case where the identified image and an image acquired in response to a same order as the identified image are included in the first medical report, the identifying unit identifies the identified image and the acquired image as the identified image.

11. The information processing apparatus according to claim 1, wherein the identifying unit performs first processing to identify an item associated with a particular item in a reverse order different from a forward order of site, findings, diagnosis, and treatment information and second processing to identify an item associated with a particular item in a direction of the forward order,
identifies, by the first processing, an item associated with an item identified by the first processing, and
identifies, by the second processing, an item associated with an item identified by the second processing.

12. The information processing apparatus according to claim 1, wherein the identifying unit performs first processing to identify an item associated with a particular item in a reverse order different from a forward order of site, findings, diagnosis, and treatment information, and wherein, in a case where an item of any one of a site item, a findings item, or a diagnosis item is specified by the specification unit, the identifying unit performs the first processing regarding a specified item, and identifies, by the first processing, an item associated with an item identified by the first processing.

13. The information processing apparatus according to claim 1, further comprising:
an evaluating unit configured to evaluate, based on the association information, an intensity of association for each of items associated with a certain item,
wherein the identifying unit identifies items where an evaluation value provided by the evaluation unit is within a predetermined range.

14. The information processing apparatus according to claim 1, wherein the identifying unit identifies information including predetermined attributes included in an item specified by the specification unit, and
wherein the display control unit displays, in a screen for editing the medical report, information including the predetermined attributes identified by the identifying unit and information not having the predetermined attributes included in the item specified by the specification unit in a distinguishable manner.

15. The information processing apparatus according to claim 14, wherein the identifying unit identifies of the plurality of items at least two items that are items included in diagnosis information regarding the object of diagnosis and that are in an exclusive association.

16. An information processing method comprising:
specifying one item, in response to receiving a user instruction from an input device that indicates the one item, out of a plurality of items included in a plurality of sets of information included in a first medical report stored in one or more storage units of an electronic medical record system, wherein items in the plurality of items include images, information of findings, information of diagnosis, and information of treatment, wherein the first medical report includes respective association information, wherein the association information describes respective associations between the images, the information of findings, the information of diagnosis, and the information of treatment, and wherein the respective associations include one or more of correspondence associations, causal associations, and exclusive associations;
identifying, based the respective association information included in the first medical report, at least one associated item, of the plurality of items included in the first medical report, associated with the one item specified by the specifying, in response to the specifying;
duplicating, in response to the specifying, the specified one item and the identified at least one associated item in a second medical report, wherein the second medical report includes respective association information, and wherein the second medical report is stored in the one or more storage units; and
displaying the second medical report, including the duplicated specified one item and the duplicated identified at least one associated item and the respective association information of the second medical report, for interpretation or diagnosis.

17. An information processing system comprising:
an electronic medical record database;
one or more memories storing a program; and
one or more processors which, by executing the program, cause the information processing system to:
create a first medical report including a plurality of sets of information and respective association information indicating associations among a plurality of items included in the plurality of sets of information and to store the first medical report in the electronic medical record database, wherein items in the plurality of items include images, information of findings, information of diagnosis, and information of treatment, and wherein the association information describes respective associations between the images, the information of findings, the information of diagnosis, and the information of treatment;
obtain a user instruction from an input device that indicates one item, out of a plurality of items included in a plurality of sets of information included in a second medical report stored in the electronic medical record database, wherein the second medical report includes respective association information;
in response to receiving the user instruction,
identify, based on the association information included in the second medical report, at least one associated item, of the plurality of items included in the second medical report, associated with the one item, and
copy the one item and the at least one associated item from the second medical report stored in the electronic medical record database to the first medical report stored in the electronic medical record database; and
display the first medical report including the one item and the at least one associated item.

* * * * *